(12) United States Patent
Gomtsyan et al.

(10) Patent No.: US 8,350,083 B2
(45) Date of Patent: Jan. 8, 2013

(54) ANTAGONISTS OF THE TRPV1 RECEPTOR AND USES THEREOF

(75) Inventors: Arthur R. Gomtsyan, Vernon Hills, IL (US); Robert G. Schmidt, Waukegan, IL (US); Jerome F. Daanen, Racine, WI (US); Erol K. Bayburt, Gurnee, IL (US); Chih-hung Lee, Vernon Hills, IL (US); Steven P. Latshaw, Round Lake Beach, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 13/249,010

(22) Filed: Sep. 29, 2011

(65) Prior Publication Data

US 2012/0022103 A1 Jan. 26, 2012

Related U.S. Application Data

(63) Continuation of application No. 11/954,875, filed on Dec. 12, 2007, now Pat. No. 8,030,504.

(60) Provisional application No. 60/875,890, filed on Dec. 20, 2006.

(51) Int. Cl.
C07C 275/00 (2006.01)
C07D 215/44 (2006.01)

(52) U.S. Cl. .................................. 564/47; 546/160

(58) Field of Classification Search .............. 564/47; 546/160
See application file for complete search history.

(56) References Cited

U.S. PATENT DOCUMENTS

| | | | |
|---|---|---|---|
| 3,647,819 A | 3/1972 | Kirchner | |
| 3,647,910 A | 3/1972 | Jones et al. | |
| 3,711,610 A | 1/1973 | Kirchner | |
| 3,814,711 A | 6/1974 | Eloy et al. | |
| 4,958,026 A | 9/1990 | Schoellkopf et al. | |
| 5,362,878 A | 11/1994 | Chang et al. | |
| 5,444,038 A | 8/1995 | James et al. | |
| 5,646,140 A | 7/1997 | Sugg et al. | |
| 5,656,634 A | 8/1997 | Chang et al. | |
| 5,760,246 A | 6/1998 | Biller et al. | |
| 6,001,860 A | 12/1999 | Hamanaka | |
| 6,291,476 B1 | 9/2001 | Kordik et al. | |
| 6,472,414 B1 | 10/2002 | Biller et al. | |
| 6,511,998 B2 | 1/2003 | Kordik et al. | |
| 6,555,539 B2 | 4/2003 | Reich et al. | |
| 6,858,577 B1 | 2/2005 | Zhang et al. | |
| 6,933,311 B2 | 8/2005 | Lee et al. | |
| 2004/0015784 A1 | 1/2004 | Chidlovskii | |
| 2004/0157849 A1 | 8/2004 | Lee et al. | |
| 2005/0119304 A1 | 6/2005 | Yura et al. | |

FOREIGN PATENT DOCUMENTS

| | | |
|---|---|---|
| EP | 418071 A2 | 3/1991 |
| EP | 587180 A2 | 3/1994 |
| EP | 591830 A1 | 4/1994 |
| EP | 609960 A1 | 8/1994 |
| EP | 1256574 A1 | 11/2002 |
| EP | 1403255 A1 | 3/2004 |
| FR | 1344579 A | 11/1963 |
| GB | 2020280 A | 11/1979 |
| JP | 4178362 A2 | 6/1992 |
| WO | WO9113874 A1 | 9/1991 |
| WO | WO9726240 A1 | 7/1997 |
| WO | WO9850347 A1 | 11/1998 |
| WO | WO0047577 A1 | 8/2000 |
| WO | WO0050387 A1 | 8/2000 |
| WO | WO0208221 A2 | 1/2002 |
| WO | WO03014064 A1 | 2/2003 |
| WO | WO03022809 A2 | 3/2003 |
| WO | WO03051274 A3 | 6/2003 |
| WO | WO03051275 A3 | 6/2003 |
| WO | WO03055484 A1 | 7/2003 |
| WO | WO03055648 A1 | 7/2003 |
| WO | WO03055848 A2 | 7/2003 |
| WO | WO03070247 A1 | 8/2003 |
| WO | WO03080578 A1 | 10/2003 |
| WO | WO03095420 A1 | 11/2003 |
| WO | WO03097586 A1 | 11/2003 |
| WO | WO2004052845 A1 | 6/2004 |
| WO | WO2004052846 A1 | 6/2004 |
| WO | WO2005002551 A3 | 1/2005 |
| WO | WO2005040100 A1 | 5/2005 |
| WO | WO2006094627 A3 | 9/2006 |

OTHER PUBLICATIONS

Greene, T.W., et al., Protective Groups in Organic Synthesis, 3rd Edition, John Wiley and Sons, Inc., 1999, Table of Contents.

Adams E.P., et al., "Dialkylaminoalkylquinolines," Journal of Chemical Society, 1957, pp. 3066-3071.

Berge, S. M. et al., "Pharmaceutical Salts," Journal of Pharmaceutical Sciences, 1977, vol. 66 (1), pp. 1-19.

(Continued)

*Primary Examiner* — Nizal Chandrakumar

(57) ABSTRACT

The present application is directed to compounds that are TRPV1 antagonists and have formula (I)

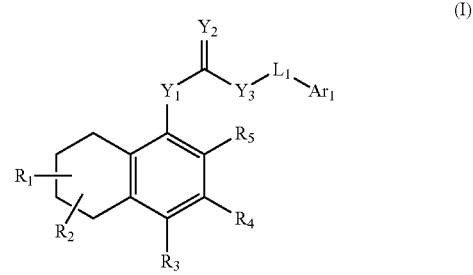

(I)

wherein variables $Ar_1$, $L_1$, $R_1$, $R_2$, $R_3$, $R_4$, $R_5$, $Y_1$, $Y_2$, and $Y_3$, are as defined in the description, which are useful for treating disorders caused by or exacerbated by vanilloid receptor activity.

16 Claims, No Drawings

OTHER PUBLICATIONS

Cannon J.G., et al., "Synthesis of N-alkyl Derivatives of 4- (2'-aminoethyl)Indole," Journal of Heterocyclic Chemistry, 1982, vol. 19, pp. 1195-1199.

Caterina, M. J. et al., "Impaired Nociception and Pain Sensation in Mice Lacking the Capsaicin Receptor," Science, 2000, vol. 288, pp. 306-313.

Caterina, M. J. et al., "The Capsaicin Receptor: A Heat-Activated Ion Channel in the Pain Pathway," Nature, 1997, vol. 389 (6653), pp. 816-824.

Caterina, M. J. et al., "The Vanilloid Receptor: A Molecular Gateway to the Pain Pathway," Annual Review of Neuroscience, 2001, vol. 24, pp. 487-517.

Collier, H.O. et al., "The Abdominal Constriction Response and its Suppression by Analgesic Drugs in the Mouse," British Journal of Pharmacology and Chemotherapy, 1968, vol. 32 (2), pp. 295-310.

Craig J.J., et al., "Derivatives of Aminoisoquinolines," Journal of the American Chemical Society, 1942, vol. 64, pp. 783-784.

Cross, L.C. et al., "IUPAC Commission on Nomenclature of Organic Chemistry: Rules for the Nomenclature of Organic Chemistry, Section E: Stereochemistry," Pure and Applied Chemistry, 1976, vol. 45, pp. 13-30.

Davies,, "Indazole Derivatives: The synthesis of various amino- and hydroxy-indazoles and derived sulphonic acids," J.Chem.Soc, 1955, 2412-2423.

Davis, J. B. et al., "Vanilloid Receptor-1 is Essential for Inflammatory Thermal Hyperalgesia," Nature, 2000, vol. 405 (6783), pp. 183-187.

Endo Y., et al., "Molecular Requirements for Epigenetic Modulators Synthesis of Active Fragments of Teleocidins and Lyngbyatoxin," Chemical and Pharmaceutical Bulletin, 1982, vol. 30 (9), pp. 3457-3460.

Fieser L.F., et al., "A Comparison of Heterocyclic Systems with Benzene VI Quinines of the Quinoline and Isoquinoline Series," Journal of the American Chemical Society, 1935, vol. 57, pp. 1840-1844.

Forbes I.T., et al., "N- (1-methyl-5-indolyl)-N'- (3-pyridyl)Urea Hydrochloride: the First Selective 5-HTsub1c Receptor Antagonist," Journal of Medicinal Chemistry, 1993, vol. 36 (8), pp. 1104-1107.

Fowler, C.J., "Intravesical Treatment of Overactive Bladder," Urology, 2000, vol. 55, pp. 60-64.

Gall R., et al., "On a Few Derivatives of Heterocyclic Carbonic Acids IV Metal Ions and Biological Action, 36th Report," Helvetica Chimica Acta, 1955, vol. 38 (171), pp. 1421-1423.

Giencke A., et al., "Desmethyl (trifluormethyl)actinomycine," Liebigs Ann Chem, 1990, vol. 6, pp. 569-579.

Hayes, P. et al., "Cloning and Functional Expression of a Human Orthologue of Rat Vanilloid Receptor-1," Pain, 2000, vol. 88, pp. 205-215.

Higuchi et al., "Bioreversible Carriers in Drug Design ,A.C.S. Symposium Series," Pro-drugs as Novel Delivery Systems, 1987, vol. 14, Edward B. Roche, American Pharmaceutical Association and Pergamon Press.

Higuchi T., et al., eds., Pro-drugs as Novels Delivery Systems, vol. 14, ACS Symposium Series, 1975, Table of Contents.

Honma T., et al., "Structure-Based Generation of a New Class of Potent Cdk4 Inhibitors: New de Novo Design Strategy and Library Design," Journal of Medicinal Chemistry, 2001, vol. 44, pp. 4615-4627.

International Search Report for Application No. PCT/US07/087163, mailed on Jul. 21, 2008, 7 pages.

International Search Report for Application No. PCT/US2003/0004187, mailed on Jul. 2, 2003, 7 pages.

International Search Report for Application No. PCT/US2004/0018590, mailed on Sep. 30, 2004, 3 pages.

International Search Report for Application No. PCT/US2004/025109, mailed on Dec. 9, 2004, 6 pages.

Kawasaki T., et al., "A New Approach to 4-(2-aminoethyl)Indoles Via Claisen Ortho-Amide Rearrangement of 3-Hydroxy-2-Methoxyindolines," Journal of the Chemical Society, Chemical Communications, 1990, vol. 10, pp. 781-782.

Kumar P., et al., "Antiparasitic Agents: Part XV—Synthesis of 2-Substituted 1(3)H-Imidazo[4,5-function]lsoquinolines as Anthelmintic Agents," Indian Journal of Chemistry, 1992, vol. 31B, pp. 177-182.

Landsiedel M.D., et al., "Structure Activity Relationship of Homochiral 7-Substituted 1-Aminoindans as 5-HT1A Receptor Ligands, XP002296522," Archie Der Pharmazie, 1998, vol. 331, pp. 59-71.

Lichtenthaler F.W., et al., "Nucleosides 44 Benzo-Separated Pyrazolopyrimidines: Expeditions Synthesis of [3,4-g] and [3,4-h]-linked Pyrazoloquinazolinones," Tetrahedron Letters, 1981, vol. 22 (44), pp. 4397-4400.

Lila C., et al., "Large Scale Preparation of Protected 4-Aminomethylbenzamidine Application to the Synthesis of the Thrombin Inhibitor, Melagatran," Synthetic Communications, 1998, vol. 28, pp. 4419-4429.

Mooney P.D., et al., "Potential Antitumor Agens, 10 Synthesis and Biochemical Properties of 5-N-Alkylamino-,N,N-Dialkylamino-, and N-Alkylacetamido-1Fformylisoquinoline Thiosemicarbazones," Journal of Medicinal Chemistry, 1974, vol. 17 (11), pp. 1145-1150.

Mukkala V.M., et al., "124. New Heteroaromatic Complexing Agents and Luminescence of Their Europium(III) and Terbium(III) Chelates," Helvetica Chimica Acta, 1992, vol. 75, pp. 1621-1632.

Naruto S., et al., "Photo-Induced Friedel-Crafts Reactions IV> Indoleacetic Acids," Chemical and Pharmaceutical Bulletin, 1972, vol. 20 (10), pp. 2163-2171.

Nolano, M. et al., "Topical Capsaicin in Humans: Parallel Loss of Epidermal Nerve Fibers and Pain Sensation," Pain, 1999, vol. 81, pp. 135-145.

Nunn A.J., et al., "Semmler-Wolf Aromatization and Abnormal Beckmann and Schmidt Reactions of 3-Alkyl-4Oxo-1-phenyl-4,5,6,7,-tetrahydroindazoles and their oximes in polyphosphoric acid," Journal Chemical Society, 1973, vol. 1 (22), pp. 2697-2703.

Pircio, A. W. et al., "A New Method for the Evaluation of Analgesic Activity Using Adjuvant-Induced Arthritis in the Rat," European Journal of Pharmacology, 1975, vol. 31 (2), pp. 207-215.

Poste G. et al., "Lipid Vesicles as Carriers for Introducing Biologically Active Materials into Cells," Methods in Cell Biology, 1976, vol. 14, pp. 33-71.

Prijs B., et al., "171 On a few derivatives of heterocyclic carbonic acids IV Metal ions and Biological Action, 36th report," Helvetica Chimica Acta, 1955, pp. 1421-1423 with English Translation.

Prijs B., et al., "9 On a Few Derivatives of Heterocyclic Carbonic Acids I. Metal ions and Biological Action, 16th report," Helvetica Chimica Acta, 1954, vol. 37, pp. 90-94 with English Translation.

Roche E.B., ed., Bioreversible Carries in Drug Design Theory and Application, Pergamon Press, 1987, Table of Contents.

Roe A., et al., "The Preparation of Heterocyclic Fluorine Compounds by the Schiemann Reaction III Some Monofluoroisoquinolines," Journal of the American Chemical Society, 1951, vol. 73, pp. 687-689.

Sato K., et al., "Construction of optically pure tryptophans from serine derived aziridine-2-carboxylates," Tetrahedro Letters, 1989, vol. 30 (31), pp. 4073-4076.

Sterling J., et al., "Novel Dual Inhibitors of AChE and MAO Derived from Hydroxy Aminoindan and Phenethylamine as Potential Treatment for Alzheimers Disease," Journal of Medicinal Chemistry, 2002, vol. 45 (24), pp. 5260-5279.

Taurins A., et al., "Thiazoloisoquinolines IV the Synthesis and Spectra of Thiazolo[4,5-h]- and Thiazolo[5,4-f]isoquinolines the Ultraviolet and Proton Magnetic Resonance Spectra of some Substitute Isoquinolines," Canadian Journal of Chemistry, 1971, vol. 49 (24), pp. 4054-4064.

Thummel R.P., et al., "Polyaza Cavity-Shaped Molecules Annelated Derivatives of 2-(2-Pyridyl)-1,8-naphthyridine and 2,2-Bi-1,8-naphthyridine," Journal of Organic Chemistry, 1984, vol. 49, pp. 2208-2212.

Warpehoski M.A., et al., "Stereoelectronic Factors Influencing the Biological Activity and DNA Interaction of Synthetic Antitumor Agents Modeled on Cc-1065 ," Journal of Medicianl Chemistry, 1988, vol. 31 (3), pp. 590-603.

Wolff, Mandred E., "Burger's Medicinal Chemistry and Drug Discovery," Principles and Practice, 1995, 975-977, 5th Ed, vol. 1, John Wiley & Sons.

Zhao R., et al., "A Concise Synthesis of the Pyrroloquinoline Nucleus of the Makaluvamine Alkaloids," Synthetic Communications, 1997, vol. 27 (12), pp. 2103-2110.

ANTAGONISTS OF THE TRPV1 RECEPTOR AND USES THEREOF

CROSS-REFERENCE TO RELATED APPLICATIONS

This is a continuation application of U.S. patent application Ser. No. 11/954,875, filed on Dec. 12, 2007, which claims priority to U.S. Provisional Patent Application No. 60/875,890, filed on Dec. 20, 2006, the contents of all of which are hereby incorporated by reference.

FIELD AND BACKGROUND

The present application relates to compounds of formula (I), which are useful for treating disorders caused by or exacerbated by vanilloid receptor activity. The present application also includes pharmaceutical compositions containing compounds of formula (I) and methods for treating pain, bladder overactivity, and urinary incontinence using said compounds and said pharmaceutical compositions.

Nociceptors are primary sensory afferent (C and Aδ fibers) neurons that are activated by a wide variety of noxious stimuli including chemical, mechanical, thermal, and proton (pH<6) modalities. The lipophillic vanilloid, capsaicin, activates primary sensory fibers via a specific cell surface capsaicin receptor, cloned as the transient receptor potential vanilloid-1 (TRPV1). The intradermal administration of capsaicin is characterized by an initial burning or hot sensation followed by a prolonged period of analgesia. The analgesic component of TRPV1 receptor activation is thought to be mediated by a capsaicin-induced desensitization of the primary sensory afferent terminal. Thus, the long lasting anti-nociceptive effects of capsaicin has prompted the clinical use of capsaicin analogs as analgesic agents. Further, capsazepine, a capsaicin receptor antagonist can reduce inflammation-induced hyperalgesia in animal models. TRPV1 receptors are also localized on sensory afferents, which innervate the bladder. Capsaicin or resiniferatoxin has been shown to ameliorate incontinence symptoms upon injection into the bladder.

The TRPV1 receptor has been called a "polymodal detector" of noxious stimuli since it can be activated in several ways. The receptor channel is activated by capsaicin and other vanilloids and thus is classified as a ligand-gated ion channel. TRPV1 receptor activation by capsaicin can be blocked by the competitive TRPV1 receptor antagonist, capsazepine. The channel can also be activated by protons. Under mildly acidic conditions (pH 6-7), the affinity of capsaicin for the receptor is increased, whereas at pH<6, direct activation of the channel occurs. In addition, when membrane temperature reaches 43° C., the channel is opened. Thus heat can directly gate the channel in the absence of ligand. The capsaicin analog, capsazepine, which is a competitive antagonist of capsaicin, blocks activation of the channel in response to capsaicin, acid, or heat.

The channel is a nonspecific cation conductor. Both extracellular sodium and calcium enter through the channel pore, resulting in cell membrane depolarization. This depolarization increases neuronal excitability, leading to action potential firing and transmission of a noxious nerve impulse to the spinal cord. In addition, depolarization of the peripheral terminal can lead to release of inflammatory peptides such as, but not limited to, substance P and CGRP, leading to enhanced peripheral sensitization of tissue.

Recently, two groups have reported the generation of a "knock-out" mouse lacking the TRPV1 receptor. Electrophysiological studies of sensory neurons (dorsal root ganglia) from these animals revealed a marked absence of responses evoked by noxious stimuli including capsaicin, heat, and reduced pH. These animals did not display any overt signs of behavioral impairment and showed no differences in responses to acute non-noxious thermal and mechanical stimulation relative to wild-type mice. The TRPV1 (−/−) mice also did not show reduced sensitivity to nerve injury-induced mechanical or thermal nociception. However, the TRPV1 knock-out mice were insensitive to the noxious effects of intradermal capsaicin, exposure to intense heat (50-55° C.), and failed to develop thermal hyperalgesia following the intradermal administration of carrageenan.

The compounds of the present application are novel TRPV1 antagonists and have utility in treating pain, inflammatory hyperalgesia, ostheoarthritic pain, chronic lower pain, migraine, bladder overactivity, and urinary incontinence.

SUMMARY

The present application is directed to compounds of formula (I)

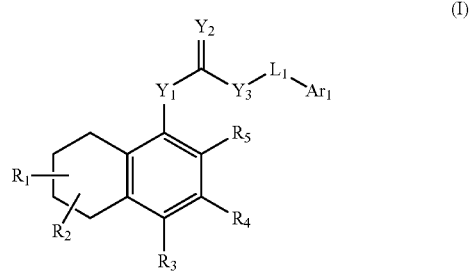

or a pharmaceutically acceptable salt or prodrug thereof, wherein $L_1$ is a bond, alkylene, or cycloalkyl;

$Y_1$ is —N($R_b$)— or —C($R_{8a}R_{8b}$)—;

$Y_2$ is =O, =S or =N—CN;

$Y_3$ is —N($R_e$)—;

$Ar_1$ is aryl or heteroaryl when $L_1$ is cycloalkyl; or $Ar_1$ is a monocyclic heterocycle fused to an aryl or a monocyclic heterocycle fused to a monocyclic heteroaryl when $L_1$ is a bond or alkylene;

wherein each $Ar_1$ is optionally substituted with 1, 2, 3, 4, or 5 substituents as represented by $R_w$, two $R_w$ that are attached to the same carbon atom of the monocyclic heterocycle, together with the carbon atom to which they are attached, optionally form a monocyclic cycloalkyl ring wherein said monocyclic cycloalkyl ring is optionally substituted with 1, 2, or 3 substituents selected from the group consisting of oxo, alkyl, and haloalkyl;

$R_1$ is hydrogen, hydroxy or alkoxy;

$R_w$, $R_2$, $R_3$, $R_4$, and $R_5$, are each independently hydrogen, alkenyl, alkoxy, alkoxyalkoxy, alkoxyalkyl, alkoxycarbonyl, alkoxycarbonylalkyl, alkyl, alkylcarbonyl, alkyl carbonyl alkyl, alkylcarbonyloxy, alkylthio, alkynyl, carboxy, carboxyalkyl, cyano, cyanoalkyl, cycloalkyl, cycloalkylalkyl, formyl, formylalkyl, haloalkoxy, haloalkyl, haloalkylthio, halogen, hydroxy, hydroxyalkyl, nitro, $R_eOS(O)_2$—, $R_fR_gN$—, ($R_fR_gN$)alkyl, ($R_jR_kN$)carbonyl, ($R_jR_kN$)carbonylalkyl or ($R_jR_kN$)sulfonyl;

$R_{8a}$ is hydrogen or alkyl;

$R_{8b}$ is hydrogen or alkyl; or $R_{8a}$ and $R_{8b}$ taken together with the carbon atoms to which they are attached, form a 3-6 membered cycloalkyl ring;

$R_b$ and $R_c$ are each independently hydrogen or alkyl;

$R_e$ is alkyl, haloalkyl, aryl, or arylalkyl;

$R_f$ and $R_g$, at each occurrence, are each independently hydrogen, alkenyl, alkoxyalkyl, alkoxycarbonyl, alkoxycarbonylalkyl, alkyl, alkylcarbonyl, alkylcarbonylalkyl, arylalkyl, arylcarbonyl, carboxyalkyl, cycloalkylalkyl, haloalkyl, heteroarylalkyl, or heteroarylcarbonyl; or $R_f$ and $R_g$ taken together with the nitrogen atom to which they are attached form a heterocyclic ring; and $R_j$ and $R_k$, at each occurrence, are each independently hydrogen, alkenyl, alkoxyalkyl, alkoxycarbonylalkyl, alkyl, alkylcarbonylalkyl, carboxyalkyl, cycloalkylalkyl, haloalkyl, or hydroxyalkyl.

The inventions further relates to a pharmaceutical composition comprising a compound of formula (I) or a pharmaceutically acceptable salt or solvate thereof, and one or more pharmaceutically acceptable carriers, alone or in combination with one or more nonsteroidal anti-inflammatory drug (NSAID).

The application is also directed to a method for inhibiting the TRPV1 receptor in mammals using compounds of formula (I).

The application also provides a method of treating disorders, wherein the disorder is pain, especially, inflammatory hyperalgesia, ostheoarthritic pain, chronic lower pain, allodynia, migraine. Methods of controlling pain and treating bladder overactivity and urinary incontinence are also disclosed.

Yet further, the invention provides the use of a compound of formula (I), or a pharmaceutically acceptable salt thereof, in the manufacture of a medicament for the treatment of disease or disorders as defined herein below, alone or in combination with one or more nonsteroidal anti-inflammatory drug (NSAID).

It is to be understood that both the foregoing general description and the following detailed description are exemplary, but are not restrictive, of the invention.

DETAILED DESCRIPTION

Compounds

Compounds of formula (I) are disclosed in this invention,

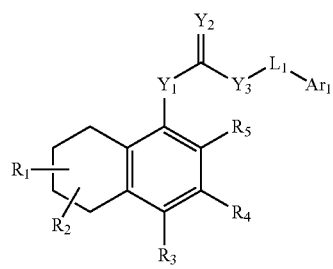

(I)

wherein $Ar_1$, $L_1$, $R_1$, $R_2$, $R_3$, $R_4$, $R_5$, $Y_1$, $Y_2$, and $Y_3$, are defined above in the Summary of the Invention and below in the Detailed Description. Preferably, compounds of the invention are TRPV1 antagonists. Further, compositions comprising such compounds and methods for treating conditions and disorders using such compounds and compositions are also disclosed.

In various embodiments, the present invention provides at least one variable that occurs more than one time in any substituent or in the compound of the invention or any other formulae herein. Definition of a variable on each occurrence is independent of its definition at another occurrence. Further, combinations of substituents are permissible only if such combinations result in stable compounds. Stable compounds are compounds, which can be isolated from a reaction mixture.

Compounds of the application can have the formula (I) as described above. More particularly, compounds of formula (I) can include, but are not limited to compounds wherein $Y_1$ is —N($R_b$)— or —C($R_{8a}R_{8b}$)—, $Y_3$ is —N($R_e$)—, and $Y_2$ is either =O, =S or =N—CN. Preferred compounds are those in which $Y_1$ is —N($R_b$)—, $Y_2$ is O, and $Y_3$ is —N($R_c$)—. The compounds of the present application include compounds wherein $Y_1$ is —N($R_b$)—, $Y_2$ is O, and $Y_3$ is —N($R_c$)—, and $L_1$ is a 4-7 membered cycloalkyl ring. More particularly, $L_1$ is cyclopentyl or cyclohexyl. Compounds of the present application include compounds wherein $Y_1$ is —N($R_b$)—, $Y_2$ is O, and $Y_3$ is —N($R_c$)—, $L_1$ is cyclopentyl or cyclohexyl, and $Ar_1$ is optionally substituted aryl, preferably optionally substituted phenyl. Compounds of the present invention also include those in which $Y_1$ is —N($R_b$)—, $Y_2$ is O, and $Y_3$ is —N($R_c$)—, and $L_1$ is a 4-7 membered cycloalkyl ring, and $Ar_1$ is optionally substituted heteroaryl. The present application includes compounds in which $Y_1$ is —N($R_b$)—, $Y_2$ is O, and $Y_3$ is —N($R_c$)— and $L_1$ is a bond. Compounds included in this group may include those in which $Ar_1$ is a monocyclic heterocycle fused to a phenyl, but also may include those in which $Ar_1$ is a monocyclic heterocycle fused to a bicyclic aryl. Preferred compounds are those in which $Y_1$ is —N($R_b$)—, $Y_2$ is O, and $Y_3$ is —N($R_e$)—, $L_1$ is a bond, $Ar_1$ is 3,4-dihydro-2H-chromen-3-yl, $R_1$ is hydroxy; and $R_2$ is hydrogen. Other preferred compounds are those in which $Y_1$ is —N($R_b$)—, $Y_2$ is O, and $Y_3$ is —N($R_e$)—, $L_1$ is a bond, $Ar_1$ is 3,4-dihydro-2H-chromen-4-yl, $R_1$ is hydroxy; and $R_2$ is hydrogen. Other preferred compounds include those wherein $Y_1$ is —N($R_b$)—, $Y_2$ is O, and $Y_3$ is —N($R_c$)—, $L_1$ is a bond, $Ar_1$ is a monocyclic heterocycle fused to a bicyclic aryl, $R_1$ is hydroxy, and $R_2$ is hydrogen. For example, compounds of the invention include those wherein $Y_1$ is —N($R_b$)—, $Y_2$ is O, and $Y_3$ is —N($R_c$)—, $L_1$ is a bond, $Ar_1$ is 3,4,7,8,9,10-hexahydro-2H-benzo[h]chromen-4-yl, $R_1$ is hydroxy, and $R_2$ is hydrogen. Among the compounds of the present application are those in which $Y_1$ is —N($R_b$)—, $Y_2$ is O, and $Y_3$ is —N($R_e$)—, $L_1$ is a bond, $Ar_1$ is a monocyclic heterocycle fused to a phenyl, (for example, $Ar_1$ is 1,2,3,4-tetrahydro-quinolin-4-yl), $R_1$ is hydroxy, and $R_2$ is hydrogen. Also included are compounds wherein $Y_1$ is —N($R_b$)—, $Y_2$ is O, and $Y_3$ is —N($R_c$)—, $L_1$ is a bond, $Ar_1$ is a monocyclic heterocycle fused to a phenyl, (for example, $Ar_1$ is 1,2,3,4-tetrahydro-quinolin-3-yl), $R_1$ is hydroxy, and $R_2$ is hydrogen. The compounds of the present application also include compounds wherein $Y_1$ is —N($R_b$)—, $Y_2$ is O, and $Y_3$ is —N($R_e$)—, and $L_1$ is alkylene. Within this group of compound are included those in which $Y_1$ is —N($R_b$)—, $Y_2$ is O, and $Y_3$ is —N($R_c$)—, $L_1$ is alkylene (for example, $L_1$ is $CH_2$), $Ar_1$ is a monocyclic heterocycle fused to a phenyl, (for example, $Ar_1$ is 3,4-dihydro 2H-chromen-2-yl, 3,4-dihydro-2H-chromen-3-yl, or 3,4-dihydro-2H-chromen-4-yl), $R_1$ is hydroxy; and $R_2$ is hydrogen. Also included in the group are those in which $Y_1$ is —N($R_b$)—, $Y_2$ is O, and $Y_3$ is —N($R_c$)—, $L_1$ is alkylene (for example, $L_1$ is $CH_2$), and $Ar_1$ is 1,2,3,4-tetrahydro-quinolin-2-yl, 1,2,3,4-tetrahydro-quinolin-3-yl, or 1,2,3,4-tetrahydro-quinolin-4-yl, $R_1$ is hydroxy; and $R_2$ is hydrogen. Other included compounds are those in which $Y_1$ is —N($R_b$)—, $Y_2$ is O, and $Y_3$ is —N($R_c$)—, $L_1$ is alkylenyl or a bond, and $Ar_1$ is a monocyclic heteroaryl.

Specific embodiments contemplated as part of the application include, but are not limited to compounds of formula (I), or salts or prodrugs thereof, for example:

N-(7-hydroxy-5,6,7,8-tetrahydronaphthalen-1-yl)-N'-{(3R)-3-[4-(trifluoromethyl)phenyl]cyclohexyl}urea;

N-{(3S)-3-[4-(dimethylamino)phenyl]cyclopentyl-}-N'-(7-hydroxy-5,6,7,8-tetrahydronaphthalen-1-yl)urea;

N-3,4-dihydro-2H-chromen-3-yl-N'-(7-hydroxy-5,6,7,8-tetrahydronaphthalen-1-yl)urea;

N-(8-tert-butyl-3,4-dihydro-2H-chromen-3-yl)-N'-(7-hydroxy-5,6,7,8-tetrahydronaphthalen-1-yl)urea;

N-(7-hydroxy-5,6,7,8-tetrahydronaphthalen-1-yl)-N'-(7-methoxy-3,4-dihydro-2H-chromen-3-yl)urea;

N-(6-chloro-3,4-dihydro-2H-chromen-3-yl)-N'-(7-hydroxy-5,6,7,8-tetrahydronaphthalen-1-yl)urea;

N-(8-tert-butyl-3,4-dihydro-2H-chromen-4-yl)-N'-(7-hydroxy-5,6,7,8-tetrahydronaphthalen-1-yl)urea;

N-3,4,7,8,9,10-hexahydro-2H-benzo[h]chromen-4-yl-N'-(7-hydroxy-5,6,7,8-tetrahydronaphthalen-1-yl)urea;

N-(7-hydroxy-5,6,7,8-tetrahydronaphthalen-1-yl)-N'-(6-methyl-3,4-dihydro-2H-chromen-4-yl)urea;

N-[(4R)-3,4-dihydro-2H-chromen-4-yl]-N'-(7-hydroxy-5,6,7,8-tetrahydronaphthalen-1-yl)urea;

N-[(4S)-3,4-dihydro-2H-chromen-4-yl]-N'-(7-hydroxy-5,6,7,8-tetrahydronaphthalen-1-yl)urea;

N-(3,4-dihydro-2H-chromen-2-ylmethyl)-N'-(7-hydroxy-5,6,7,8-tetrahydronaphthalen-1-yl)urea;

N-[(7-ethoxy-3,4-dihydro-2H-chromen-2-yl)methyl]-N'-(7-hydroxy-5,6,7,8-tetrahydronaphthalen-1-yl)urea;

N-(7-hydroxy-5,6,7,8-tetrahydronaphthalen-1-yl)-N'-[(6-methyl-3,4-dihydro-2H-chromen-2-yl)methyl]urea;

N-(7-hydroxy-5,6,7,8-tetrahydronaphthalen-1-yl)-N'-[(8-isopropyl-3,4-dihydro-2H-chromen-2-yl)methyl]urea;

N-(8-tert-butyl-1-methyl-1,2,3,4-tetrahydroquinolin-4-yl)-N'-(7-hydroxy-5,6,7,8-tetrahydronaphthalen-1-yl)urea;

N-(1-benzyl-1,2,3,4-tetrahydroquinolin-3-yl)-N'-(7-hydroxy-5,6,7,8-tetrahydronaphthalen-1-yl)urea;

N-[1-benzyl-7-(trifluoromethyl)-1,2,3,4-tetrahydroquinolin-3-yl]-N'-(7-hydroxy-5,6,7,8-tetrahydronaphthalen-1-yl)urea;

N-(7-hydroxy-5,6,7,8-tetrahydronaphthalen-1-yl)-N'-(1-methyl-1,2,3,4-tetrahydroquinolin-4-yl)urea;

N-(7-hydroxy-5,6,7,8-tetrahydronaphthalen-1-yl)-N'-[1-methyl-7-(trifluoromethyl)-1,2,3,4-tetrahydroquinolin-4-yl]urea;

N-(1-benzyl-1,2,3,4-tetrahydroquinolin-3-yl)-N'-(7-hydroxy-5,6,7,8-tetrahydronaphthalen-1-yl)urea;

N-[1-benzyl-7-(trifluoromethyl)-1,2,3,4-tetrahydroquinolin-3-yl]-N'-(7-hydroxy-5,6,7,8-tetrahydronaphthalen-1-yl)urea;

N-(7-hydroxy-5,6,7,8-tetrahydronaphthalen-1-yl)-N'-(1-methyl-1,2,3,4-tetrahydroquinolin-3-yl)urea;

N-(7-hydroxy-5,6,7,8-tetrahydronaphthalen-1-yl)-N'-[1-methyl-7-(trifluoromethyl)-1,2,3,4-tetrahydroquinolin-3-yl]urea;

N-[(1-benzyl-1,2,3,4-tetrahydroquinolin-2-yl)methyl]-N'-(7-hydroxy-5,6,7,8-tetrahydronaphthalen-1-yl)urea;

N-{[1-benzyl-7-(trifluoromethyl)-1,2,3,4-tetrahydroquinolin-2-yl]methyl}-N'-(7-hydroxy-5,6,7,8-tetrahydronaphthalen-1-yl)urea;

N-(7-hydroxy-5,6,7,8-tetrahydronaphthalen-1-yl)-N'-{[1-methyl-7-(trifluoromethyl)-1,2,3,4-tetrahydroquinolin-2-yl]methyl}urea;

N-(7-hydroxy-5,6,7,8-tetrahydronaphthalen-1-yl)-N'-{(3R)-3-[4-(trifluoromethyl)phenyl]cyclohexyl}urea; and N-{(3S)-3-[4-(dimethylamino)phenyl]cyclopentyl}-N'-(7-hydroxy-5,6,7,8-tetrahydronaphthalen-1-yl)urea.

Definition Of Terms

All patents, patent applications, and literature references cited in the specification are herein incorporated by reference in their entirety. In the case of inconsistencies, the present disclosure, including definitions, will prevail.

As used throughout this specification and the appended claims, the following terms have the following meanings:

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein, means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkyl" as used herein, means an alkoxy group, as defined herein, appended to the parent molecular moiety through an alkylene group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkyl" as used herein, means an alkoxycarbonyl group, as defined herein, appended to the parent molecular moiety through an alkylene group, as defined herein. Representative examples of alkoxycarbonylalkyl include, but are not limited to, 3-methoxycarbonylpropyl, 4-ethoxycarbonylbutyl, and 2-tert-butoxycarbonylethyl.

The term "alkyl" as used herein, means a straight or branched chain saturated hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonylalkyl" as used herein, means an alkylcarbonyl group, as defined herein, appended to the parent molecular moiety through an alkylene group, as defined herein. Representative examples of alkylcarbonylalkyl include, but are not limited to, 2-oxopropyl, 3,3-dimethyl-2-oxopropyl, 3-oxobutyl, and 3-oxopentyl.

The term "alkylcarbonyloxy" as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylthio" as used herein, means an alkyl group, as defined herein, appended to the parent molecular moiety through a sulfur atom. Representative examples of alkylthio include, but are not limited, methylthio, ethylthio, tert-butylthio, and hexylthio.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl," as used herein, means phenyl, a bicyclic aryl or a tricyclic aryl. The bicyclic aryl is naphthyl, or a phenyl fused to a monocyclic cycloalkyl, or a phenyl fused to a monocyclic cycloalkenyl. The bicyclic aryl of the present application are attached to the parent molecular moiety through any available carbon atom contained within the bicyclic aryl group. Representative examples of the bicyclic aryl include, but are not limited to, dihydroindenyl, indenyl, naphthyl, dihydronaphthalenyl, and 1,2,3,4-tetrahydronaphthalenyl. The tricyclic aryl is a bicyclic aryl fused to a monocyclic cycloalkyl, or a bicyclic aryl fused to a monocyclic cycloalkenyl, or a bicyclic aryl fused to a phenyl. The tricyclic aryl is attached to the parent molecular moiety through any substitutable carbon atom contained within the tricyclic aryl. Representative examples of tricyclic aryls include, but are not limited to, anthracene, phenanthrene, dihydroanthracenyl, fluorenyl, and tetrahydrophenanthrenyl.

The aryl groups of this application are optionally substituted with 1, 2, 3, 4, or 5 substituents independently selected from alkenyl, alkoxy, alkoxyalkoxy, alkoxyalkoxyalkyl, alkoxyalkyl, alkoxycarbonyl, alkoxycarbonylalkyl, alkyl, alkylcarbonyl, alkylcarbonylalkyl, alkylcarbonyloxy, alkylsulfinyl, alkylsulfinylalkyl, alkylsulfonyl, alkylsulfonylalkyl, alkylthio, alkylthioalkyl, alkynyl, arylalkyl, carboxy, carboxyalkyl, cyano, cyanoalkyl, formyl, formylalkyl, halogen, haloalkyl, haloalkoxy, hydroxy, hydroxyalkyl, mercapto, nitro, oxo, —$NZ_1Z_2$ and ($NZ_3Z_4$)carbonyl, unless stated otherwise; and wherein the aryl moiety of the arylalkyl is optionally substituted with 1, 2, 3, 4, or 5 substituents selected from the group consisting of alkyl, haloalkyl, alkoxy, haloalkoxy, and halogen.

The term "arylalkyl" as used herein, means an aryl group, as defined herein, appended to the parent molecular moiety through an alkylene group, as defined herein. Representative examples of arylalkyl include, but are not limited to, benzyl, 2-phenylethyl, 3-phenylpropyl, and 2-naphth-2-ylethyl.

The term "arylcarbonyl," as used herein, means a aryl group appended to the parent molecular moiety through a carbonyl group, as defined herein.

The term "azido" as used herein, means a —$N_3$ group.

The term "carbonyl" as used herein, means a —C(O)— group.

The term "carboxy" as used herein, means a —$CO_2H$ group.

The term "carboxyalkyl" as used herein, means a carboxy group, as defined herein, appended to the parent molecular moiety through an alkylene group, as defined herein. Representative examples of carboxyalkyl include, but are not limited to, carboxymethyl, 2-carboxyethyl, and 3-carboxypropyl.

The term "cyano" as used herein, means a —CN group.

The term "cyanoalkyl" as used herein, means a cyano group, as defined herein, appended to the parent molecular moiety through an alkylene group, as defined herein. Representative examples of cyanoalkyl include, but are not limited to, cyanomethyl, 2-cyanoethyl, and 3-cyanopropyl.

The term "cycloalkenyl" as used herein, means a monocyclic or bicyclic ring system containing from 3 to 10 carbons and containing at least one carbon-carbon double bond. Representative examples of monocyclic ring systems include, but are not limited to, 2-cyclohexen-1-yl, 3-cyclohexen-1-yl, 2,4-cyclohexadien-1-yl and 3-cyclopenten-1-yl. Bicyclic ring systems are exemplified by a monocyclic cycloalkenyl ring fused to a monocyclic cycloalkyl ring, or a monocyclic cycloalkenyl ring fused to a monocyclic cycloalkenyl ring. The bicyclic cycloalkenyl groups of the present application are appended to the parent molecular moiety through any substitutable carbon atom within the group. Representative examples of bicyclic cycloalkenyls include, but are not limited to 4,5-dihydro-benzo[1,2,5]oxadiazole, 3a,4,5,6,7,7a-hexahydro-1H-indenyl, 1,2,3,4,5,6-hexahydro-pentalenyl and 1,2,3,4,4a,5,6,8a-octahydro-pentalenyl.

The term "cycloalkyl" as used herein, means a monocyclic or bicyclic cycloalkyls. Monocyclic cycloalkyls are exemplified by saturated cyclic hydrocarbon groups containing from 3 to 8 carbon atoms in the rings. Examples of monocyclic cycloalkyls include cyclopropyl, cyclobutyl, cyclopentyl, cyclohexyl, cycloheptyl, and cyclooctyl. Bicyclic cycloalkyl groups of the present application are exemplified by a monocyclic cycloalkyl fused to a monocyclic cycloalkyl. The bicyclic cycloalkyl groups of the present application are appended to the parent molecular moiety through any substitutable carbon atom within the groups. Representative examples of bicyclic cycloalkyls include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane.

The cycloalkenyl and the cycloalkyl groups of the present application are optionally substituted with 1, 2, 3, 4, or 5 substituents selected from the group consisting of alkenyl, alkoxy, alkoxyalkoxy, alkoxyalkyl, alkoxycarbonyl, alkoxysulfonyl, alkyl, alkylcarbonyl, alkylcarbonyloxy, alkylsulfonyl, alkylthio, alkylthioalkyl, alkynyl, carboxy, cyano, formyl, haloalkoxy, haloalkyl, halogen, hydroxy, hydroxyalkyl, mercapto, oxo, —$NZ_1Z_2$ or ($NZ_3Z_4$)carbonyl, unless stated otherwise.

The term "cycloalkylalkyl," as used herein, means a cycloalkyl group appended to the parent molecular moiety through an alkylene group, as defined herein.

The term "formyl" as used herein, means a —C(O)H group.

The term "formylalkyl" as used herein, means a formyl group, as defined herein, appended to the parent molecular moiety through an alkylene group, as defined herein.

The term "halo" or "halogen" as used herein, means —Cl, —Br, —I or —F.

The term "haloalkoxy" as used herein, means an alkoxy group, as defined herein, in which one, two, three, four, five or six hydrogen atoms are replaced by halogen. Representative examples of haloalkoxy include, but are not limited to, trifluoromethoxy, difluoromethoxy, 2,2,2-trifluoroethoxy, and 2,2-difluoroethoxy.

The term "haloalkyl" as used herein, means at least one halogen, as defined herein, appended to the parent molecular moiety through an alkylene group, as defined herein. Representative examples of haloalkyl include, but are not limited to, chloromethyl, 2-fluoroethyl, trifluoromethyl, pentafluoroethyl, and 2-chloro-3-fluoropentyl.

The term "haloalkylthio" as used herein, means an alkyl group, as defined herein, appended to the parent molecular moiety through a sulfur atom.

The term "heteroaryl," as used herein, means a monocyclic heteroaryl or a bicyclic heteroaryl. The monocyclic heteroaryl is a 5 or 6 membered ring containing at least one heteroatom independently selected from the group consisting of O, N, and S. The 5 membered ring contains two double bonds and may contain one, two, three or four heteroatoms. The 6 membered ring contains three double bonds and may contain one, two, three or four heteroatoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, or a monocyclic heteroaryl fused to a monocyclic cycloalkyl, or monocyclic heteroaryl fused to a monocyclic cycloalkenyl, or monocyclic heteroaryl fused to a monocyclic heteroaryl, or monocyclic heteroaryl fused to a monocyclic heterocycle. The bicyclic heteroaryl groups of the present application are appended to the parent molecular moiety through any substitutable carbon atom within the groups. Representative examples of bicyclic heteroaryls include, but are not limited to, benzofuranyl, benzoxadiazolyl, 1,3-benzothiazolyl, benzimidazolyl, benzodioxolyl, benzothiophenyl, chromenyl, cinnolinyl, furopyridine, indolyl, indazolyl, isoindolyl, isoquinolinyl, naphthyridinyl, oxazolopyridine, quinolinyl, thienopyridine and thienopyridinyl.

The heteroaryl groups of the present application are optionally substituted with 1, 2, 3, 4, or 5 substituents independently selected from the group consisting of alkenyl, alkoxy, alkoxyalkoxy, alkoxyalkyl, alkoxycarbonyl, alkoxycarbonylalkyl, alkoxysulfonyl, alkyl, alkyl carbonyl, alkyl carbonyl alkyl, alkylcarbonyloxy, alkylthio, alkylthioalkyl, alkynyl, arylalkyl, carboxy, carboxyalkyl, cyano, cyanoalkyl, formyl, haloalkoxy, haloalkyl, halogen, hydroxy, hydroxyalkyl, mercapto, nitro, oxo, —$NZ_1Z_2$ or ($NZ_3Z_4$)carbonyl, unless stated otherwise, and wherein the aryl moiety of the arylalkyl is optionally substituted with 1, 2, 3, 4, or 5 substituents selected from the group consisting of alkyl, haloalkyl, alkoxy, haloalkoxy, and halogen; unless otherwise stated. Heteroaryl groups of the present application that are substituted with hydroxyl groups may be present as tautomers. The heteroaryl rings of the present application encompass all tautomers including non-aromatic tautomers.

The term "heteroarylalkyl," as used herein, means a heteroaryl group appended to the parent molecular moiety through an alkylene group, as defined herein.

The term "heteroarylcarbonyl," as used herein, means a heteroaryl group appended to the parent molecular moiety through a carbonyl group, as defined herein.

The term "monocyclic heterocycle" or "monocyclic heterocyclic" as used herein, is a 3, 4, 5, 6 or 7 membered ring containing at least one heteroatom independently selected from the group consisting of O, N and S. The 3 or 4 membered ring contains 1 heteroatom selected from the group consisting of O, N and S. The 5 membered ring contains zero or one double bond and one or two heteroatoms selected from the group consisting of O, N and S. The 6 or 7 membered ring contains zero, one or two double bonds and one or two heteroatoms selected from the group consisting of O, N and S. The monocyclic heterocycle is connected to the parent molecular moiety through any substitutable carbon atom within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydro-2H-pyran, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl.

The term "hydroxy" as used herein, means an —OH group.

The term "hydroxyalkyl" as used herein, means at least one hydroxy group, as defined herein, is appended to the parent molecular moiety through an alkylene group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "hydroxy-protecting group" or "O-protecting group" means a substituent that protects hydroxyl groups against undesirable reactions during synthetic procedures. Examples of hydroxy-protecting groups include, but are not limited to, substituted methyl ethers, for example, methoxymethyl, benzyloxymethyl, 2-methoxyethoxymethyl, 2-(trimethylsilyl)-ethoxymethyl, benzyl, and triphenylmethyl, tetrahydropyranyl ethers, substituted ethyl ethers, for example, 2,2,2-trichloroethyl and t-butyl, silyl ethers, for example, trimethylsilyl, t-butyldimethylsilyl and t-butyldiphenylsilyl, cyclic acetals and ketals, for example, methylene acetal, acetonide and benzylidene acetal, cyclic ortho esters, for example, methoxymethylene, cyclic carbonates, and cyclic boronates. Commonly used hydroxy-protecting groups are disclosed in T. W. Greene and P. G. M. Wuts, Protective Groups in Organic Synthesis, 3rd edition, John Wiley & Sons, New York (1999).

The term "mercapto" as used herein, means a —SH group.

The term "nitrogen protecting group" as used herein, means those groups intended to protect an amino group against undesirable reactions during synthetic procedures. Preferred nitrogen protecting groups are acetyl, benzoyl, benzyl, benzyloxycarbonyl (Cbz), formyl, phenyl sulfonyl, tert-butoxycarbonyl (Boc), tert-butyl acetyl, trifluoroacetyl, and triphenylmethyl (trityl).

The term "nitro" as used herein, means a —$NO_2$ group.

The term "$NZ_1Z_2$" as used herein, means two groups, $Z_1$ and $Z_2$, which are appended to the parent molecular moiety through a nitrogen atom. $Z_1$ and $Z_2$ are each independently hydrogen, alkyl, alkoxyalkyl, alkylcarbonyl, or formyl. In certain instances within the present invention, $Z_1$ and $Z_2$ taken together with the nitrogen atom to which they are attached form a monocyclic heterocycle wherein said monocyclic heterocycle is optionally substituted with 1, 2, 3, or 4 substituents selected from the group consisting of alkyl, haloalkyl, and oxo. Representative examples of $NZ_1Z_2$ include, but are not limited to, amino, methylamino, acetylamino, acetylmethylamino, phenylamino, benzylamino, azetidinyl, pyrrolidinyl and piperidinyl.

The term "$NZ_3Z_4$" as used herein, means two groups, $Z_3$ and $Z_4$, which are appended to the parent molecular moiety through a nitrogen atom. $Z_3$ and $Z_4$ are each independently hydrogen, alkyl, or haloalkyl. Representative examples of $NZ_3Z_4$ include, but are not limited to, amino, methylamino, phenylamino and benzylamino.

The term "(NZ₃Z₄)carbonyl" as used herein, means a NZ₃Z₄ group, as defined herein, appended to the parent molecular moiety through a carbonyl group, as defined herein. Representative examples of (NZ₃Z₄)carbonyl include, but are not limited to, aminocarbonyl, (methylamino)carbonyl, (dimethylamino)carbonyl, and (ethylmethylamino)carbonyl.

The term "oxo" as used herein, means a =O moiety.

The term "sulfinyl" as used herein, means a —S(O)— group.

The term "sulfonyl" as used herein, means a —SO₂— group.

The term "tautomer" as used herein means a proton shift from one atom of a compound to another atom of the same compound wherein two or more structurally distinct compounds are in equilibrium with each other.

Compounds of the present application may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30. The present application contemplates various stereoisomers and mixtures thereof and these are specifically included within the scope of this application. Stereoisomers include enantiomers and diastereomers, and mixtures of enantiomers or diastereomers. Individual stereoisomers of compounds of the present application may be prepared synthetically from commercially available starting materials that contain asymmetric or chiral centers or by preparation of racemic mixtures followed by resolution which is well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Compounds of the formula (I) contain at least 2 stereogenic centers. Two sterogenic centers contained within the compounds of the present application are contained within $L_1$ which is defined as cycloalkyl. The stereogenic carbon atoms of the cycloalkyl ring influence the absolute and relative stereoconfigurations of the compounds of the present application. The binding properties of TRPV1 antagonists of the present application are directly influenced by the absolute and relative stereoconfiguration of the stereocenters contained within the cycloalkyl ring.

The compounds and processes of the present application will be better understood by reference to the following Examples, which are intended as an illustration of and not a limitation upon the scope of the application. Further, all citations herein are incorporated by reference.

Compounds of the application were named by ACD/ChemSketch version 5.01 (developed by Advanced Chemistry Development, Inc., Toronto, ON, Canada) or were given names consistent with ACD nomenclature. Alternatively, compounds were assigned names using ChemDraw Ultra 9.0 (or higher version) (Cambridgesoft). The practice of assigning names to chemical compounds from structures, and of assigning chemical structures from given chemical names is well known to those of ordinary skill in the art.

Preparation of Compounds

The compounds of this application can be prepared by a variety of synthetic procedures. Representative procedures are shown in, but are not limited to, Schemes 1-14.

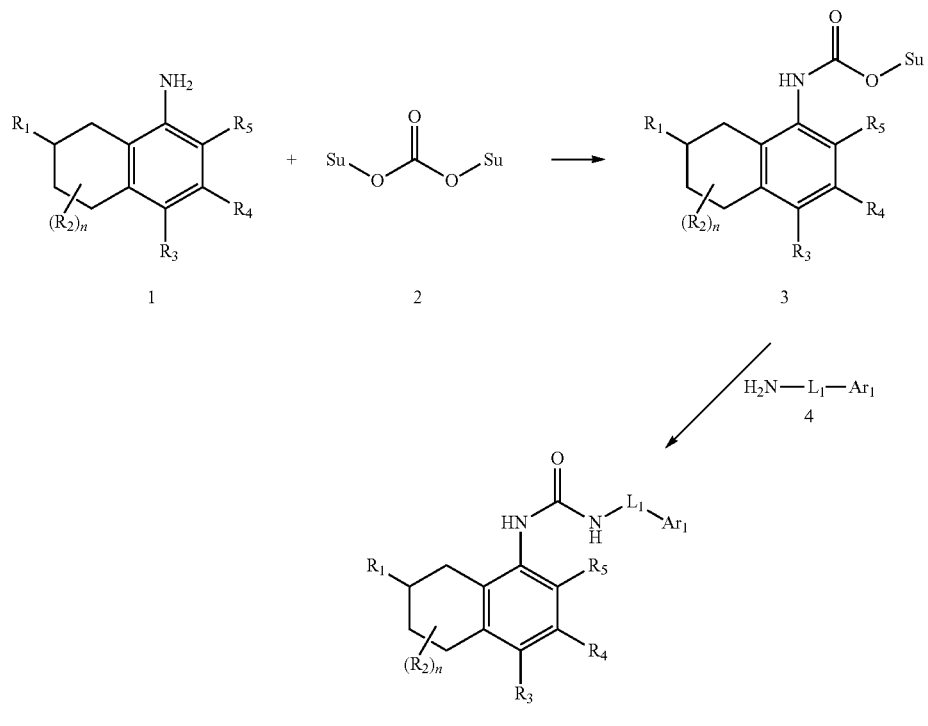

Scheme 1

As outlined in Scheme 1, compounds of formula 5, wherein $Ar_1$, $L_1$, $R_1$, $R_2$, $R_3$, $R_4$, $R_5$ and n are defined in formula (I), which are representative of compounds of the present application, may be prepared accordingly. Compounds of formula 1, wherein $R_1$, $R_2$, $R_3$, $R_4$, $R_5$ and n are defined in formula (I) which may be obtained from commercial sources or may be prepared according to procedures known in the literature or through methods known to one skilled in the art, when treated with compounds of formula 2 (N-N'-disuccuinimidyl carbonate), in a solvent such as but not limited to acetonitrile will provide compounds of formula 3. Compounds of formula 3 when treated with a compound of formula 4, wherein $L_1$ and $Ar_1$ are defined in formula (I) which may be obtained from commercial sources or may be prepared from known literature procedures or through methods known to one skilled in the art, in a solvent such as but not limited to acetonitrile or THF will provide compounds of formula 5.

Scheme 2

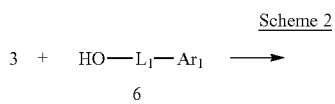

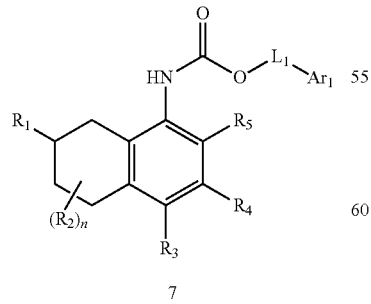

Alternatively, compounds of formula 3 described in Scheme 1, when treated with compounds of formula 6, wherein $L_1$ and $Ar_1$ are defined in formula (I) which may be obtained from commercial sources or may be prepared according to procedures known in the literature or may be prepared according to methods known to one skilled in the art, in the presence of a base such as but not limited to diisopropylethylamine or triethylamine in a solvent such as but not limited to acetonitrile or THF will provide compounds of formula 7 which are representative of compounds of the present application when $Y_3$ is —O—.

Scheme 3

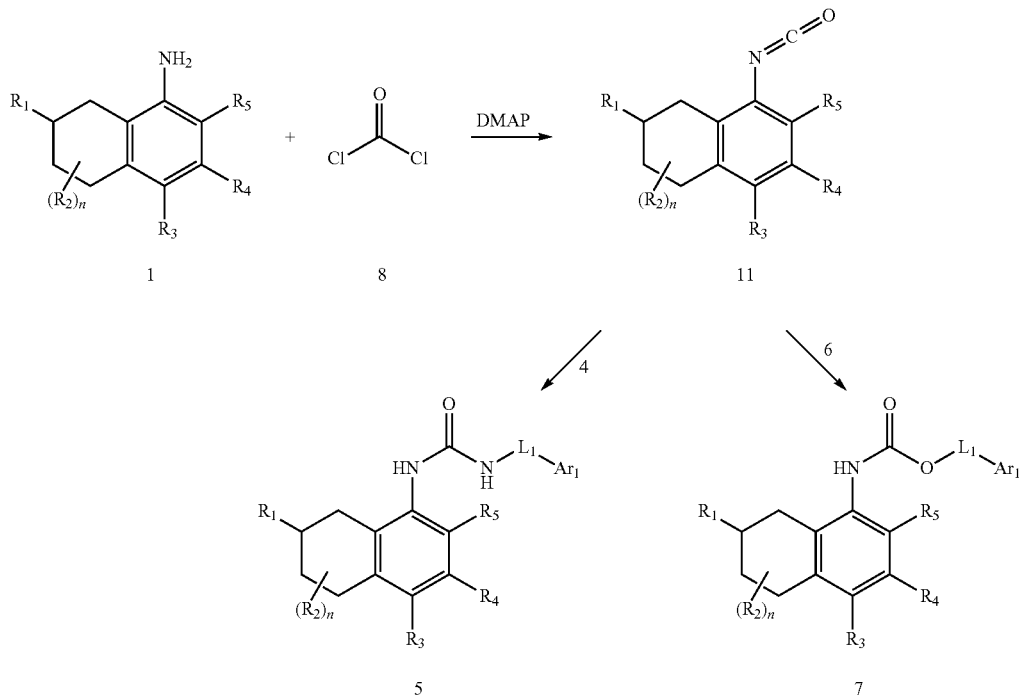

Alternatively when compounds of formula 1, wherein $R_1$, $R_2$, $R_3$, $R_4$, $R_5$, n, $L_1$ and $Ar_1$ are defined in formula (I), when treated with the compound of formula 8 (20% phosgene in toluene) in the presence of DMAP (>2 equivalents) in a solvent such as but not limited to dichloromethane, will provide compounds of formula 11. Compounds of formula 11 when treated with compounds of formula 4, which are described in Scheme 1, will provide compounds of formula 5 which are representative of compounds of formula (I) when $Y_3$ is —NH—. Alternatively, compounds of formula 11 when treated with compounds of formula 6, which are described in Scheme 2, will provide compounds of formula 7 which are representative of compounds of formula (I) when $Y_3$ is —O—.

Scheme 4

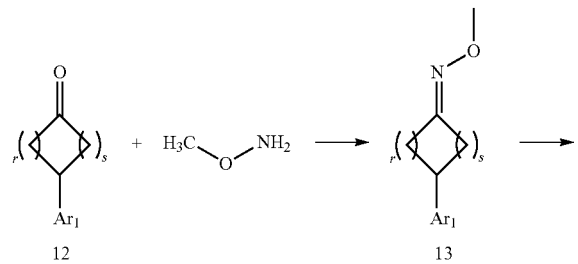

15
-continued

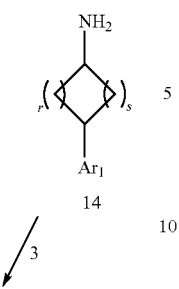

14

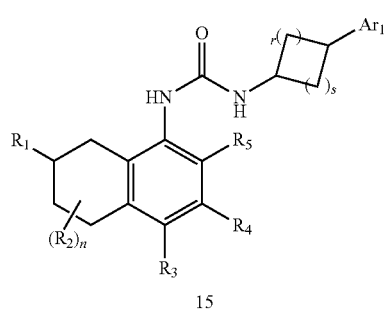

15

As outlined in Scheme 4, compounds of formula 12, wherein r is 1 or 2, s is 1, 2, 3 or 4 and $Ar_1$ is as defined in formula (I), when treated with O-methyl hydroxylamine hydrochloride in pyridine or a mixture ethanol and pyridine will provide compounds of formula 13. Compounds of formula 13 when treated with Raney Nickel or a palladium catalyst such as 5-10% palladium under a pressurized atmosphere of hydrogen in a solvent such as ethanol, will provide compounds of formula 14. Typical conditions for the transformation of compounds of formula 13 into compounds of formula 14 include shaking or stirring the mixture of compound of formula 13 and the Raney-Nickel or a palladium catalyst under 40-70 psi of hydrogen at ambient temperature for 1-4 hours followed by filtration of the catalyst. Compounds of formula 14 when treated with compounds of formula 3, described in Scheme 1, will provide compounds of formula 15 which are representative of compounds of the present application. Alternatively, compounds of formula 14 may be obtained through a reductive amination of compounds of formula 12 with benzylamine using sodium borohydride followed by treatment of the product with palladium on carbon or another benzyl reducing catalyst in the presence of hydrogen.

Scheme 5

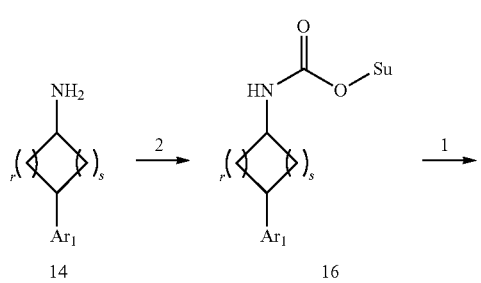

16
-continued

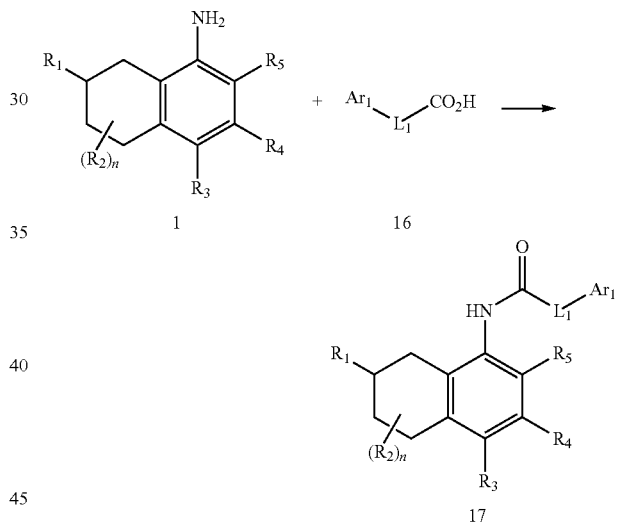

15

Alternatively compound of formula 14, wherein r is 1 or 2, s is 1, 2, 3 or 4 and $Ar_1$ is as defined in formula (I), when treated with the compound of formula 2 as defined in Scheme 1, will provide compounds of formula 16. Compounds of formula 16 when treated with compounds of formula 1, as defined in Scheme 1, will provide compounds of formula 15 which are representative of compounds of the present application.

Scheme 6

When compounds of formula 1, wherein $R_1$, $R_2$, $R_3$, $R_4$, $R_5$ and n are defined in formula (I), and compounds of formula 16, wherein $Ar_1$ and $L_1$ are defined in formula (I) are treated according to standard carboxylic acid amine coupling conditions known to one skilled in the art will provide compounds of formula 17 which are representative of compounds of the present application wherein $Y_3$ is a bond. Standard carboxylic acid amine coupling conditions include stirring the mixture of the carboxylic acid and the amine with a coupling reagent such as but not limited to 1-(3-dimethylaminopropyl)-3-ethylcarbodiimide hydrochloride (EDCI), 1,3-dicyclohexylcarbodiimide (DCC), bis(2-oxo-3-oxazolidinyl)phosphinic chloride (BOPCl), O-(7-azabenzotriazol-1-yl)-N,N,N',N'-tetramethyluronium hexafluorophosphate (HATU) or O-benzotriazol-1-yl-N,N,N',N'-tetramethyluronium tetrafluoroborate (TBTU) with or without an auxiliary reagent such as but not limited to 1-hydroxy-7-azabenzotriazole (HOAT) or 1-hydroxybenzotriazole hydrate (HOBT) in a solvent such as but not limited to dichloromethane.

Scheme 7

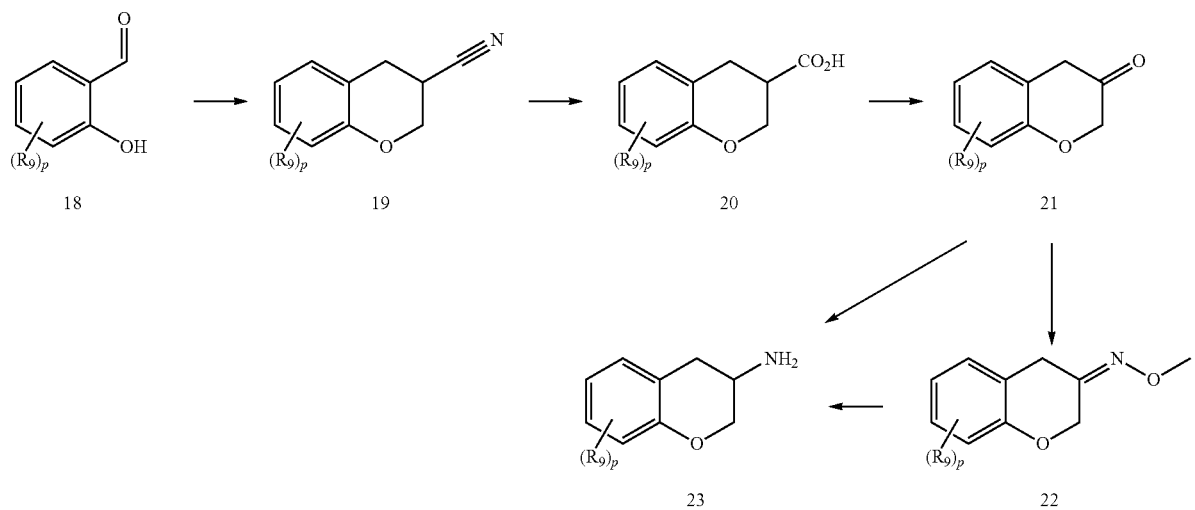

As outlined in Scheme 7, compounds of formula 23 which are representative of heterocycles $Ar_1$, may be prepared as outlined. Compounds of formula 18 wherein $R_9$ is alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkynyl, cycloalkyl, cycloalkylalkyl, haloalkoxy, haloalkyl or halogen, and p is 0, 1, 2 or 3 when treated with acrylonitrile and DABCO® under heated condition will provide compounds of formula 19. Compounds of formula 18 may be obtained from commercial sources or may be prepared according to procedures known to one skilled in the art. Compounds of formula 19 when treated with aqueous sodium hydroxide under heated conditions will provide compounds of formula 20. Compounds of formula 20 when heated in the presence of DPPA and triethylamine in toluene followed by heating in the presence of 6M hydrochloric acid will provide compounds of formula 21. Compounds of formula 21 when treated with O-methylhydroxylamine in pyridine or a mixture of pyridine and ethanol will provide compounds of formula 22. Compounds of formula 22 when treated with an atmosphere of hydrogen in the presence of Raney-nickel in a solvent such as methanol containing anhydrous ammonia gas will provide compounds of formula 23. Alternatively, compounds of formula 21 when treated with ammonium acetate followed by treatment with sodium cyanoborohydride in a solvent such as but not limited to THF will provide compounds of formula 23. In addition, the ketone of compound of formula 21, may be treated with benzyl amine followed by the addition of sodium cyanoborohydride will provide the benzyl protected amine. The benzyl protecting group may be removed by treatment with an atmosphere of hydrogen and a palladium catalyst such as 10% palladium on carbon in a solvent such as methanol with or without a catalytic amount of acetic acid to provide compounds of formula 23.

Scheme 8

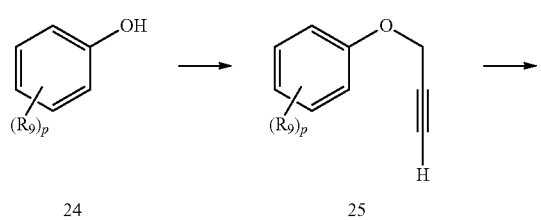

As outlined in Scheme 8, compounds of formula 28 which are representative of heterocycles $Ar_1$, may be prepared as outlined. Compounds of formula 24, wherein $R_9$ and p are as defined in Scheme 7 which are available from commercial sources or may be prepared according to methods known to one skilled in the art, when treated with 3-bromo-1-propyne and potassium carbonate in acetonitrile will provide compounds of formula 25. Compounds of formula 25 when treated with N-chlorosuccinimide and silver acetate in acetone under heated conditions will provide compounds of formula 26. Compounds of formula 26 when heated in a solvent such as but not limited to ethylene glycol will provide compounds of formula 27. Compounds of formula 27 when treated with O-methylhydroxylamine in pyridine or a mixture of pyridine and ethanol will provide the O-methyl oxime which when treated with an atmosphere of hydrogen in the presence of Raney-nickel in a solvent such as methanol containing anhydrous ammonia gas will provide compounds of formula 28. Alternatively, compounds of formula 27 when treated with ammonium acetate and sodium cyanoborohydride in a solvent such as but not limited to THF will provide compounds of formula 28. In addition, the ketone may also be subjected to reductive amination conditions in the presence of benzylamine followed by hydrogenation to remove the benzyl group to provide compounds of formula 28, which may be treated according to the procedures outlined above to generate compounds of formula (I).

Scheme 9

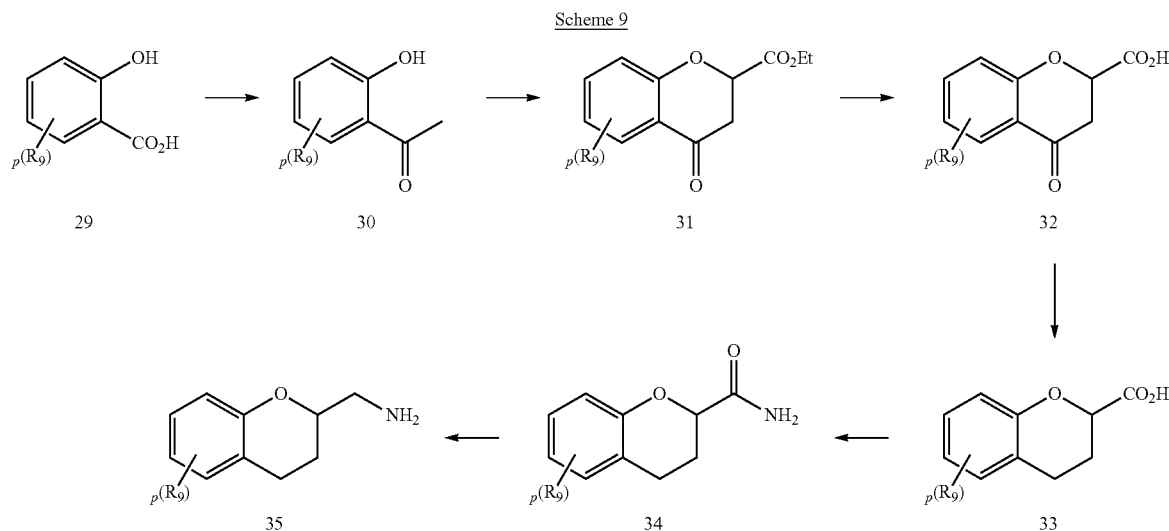

As outlined in Scheme 9, compounds of formula 35 which are representative of heterocycles $Ar_1$, may be prepared accordingly. Compounds of formula 29, wherein $R_9$ and p are defined in Scheme 7, which may be obtained from commercial sources or may be prepared according to methods known to one skilled in the art, when treated with 3 equivalents of methyl lithium in THF at about −70° C. then allowing the mixture to warm to ambient temperature will provide compounds of formula 30. Compounds of formula 30 when treated with diethyl oxalate and sodium ethoxide in ethanol under heated conditions will provide compounds of formula 31. The hydrolysis of the ester functional group of compounds of formula 31 with aqueous 12 N HCl in acetic acid under heated conditions will to provide compounds of formula 32. Compounds of formula 32 when treated with 10% palladium on carbon and an atmosphere of hydrogen in acetic acid heated to temperatures of about 70° C. will provide compounds of formula 33. Compounds of formula 33 when treated with oxalyl chloride and a catalytic amount of DMF in dichloromethane will provide the acid chloride which when subjected to ammonia gas in dioxane or concentrated ammonium hydroxide in dioxane or THF will provide compounds of formula 34. Compounds of formula 34 when treated with lithium aluminum hydride in THF under heated conditions will provide compounds of formula 35, which may be treated according to the procedures outlined above to generate compounds of formula (I).

Scheme 10

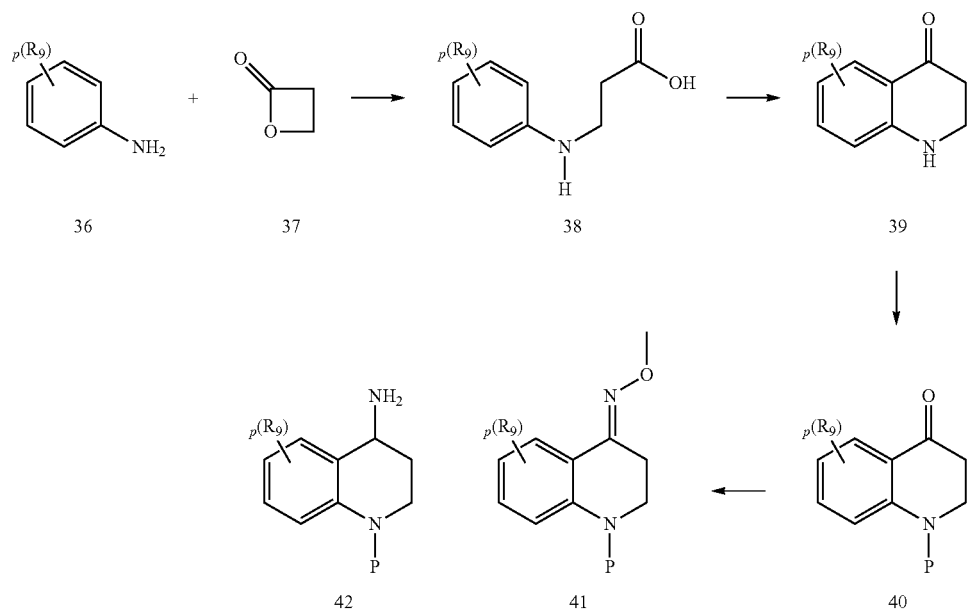

As outlined in Scheme 10, compounds of formula 42 which are representative of heterocycles $Ar_1$, may be prepared accordingly. Compounds of formula 36 which are available from commercial sources or may be obtained through methods known to one skilled in the art, wherein $R_9$ and p are as described above, when treated with oxetan 2-one (37) in acetonitrile under heated conditions will provide compounds of formula 38. Compounds of formula 38 when treated with Eaton' reagent (7.7 weight % phosphorous pentoxide in methane sulfonic acid) under heated conditions will provide compounds of formula 39. Compounds of formula 39 when treated with reagents that will protect amine functional groups as known to one skilled in the art or as outlined in T. W. Greene and P. G. M. Wuts, Protective Groups in Organic Synthesis, 3rd edition, John Wiley & Sons, New York (1999) will provide compounds of formula 40. Compounds of formula 40 when treated with O-methylhydroxylamine in pyridine will provide compounds of formula 41. Compounds of formula 41 when treated with an atmosphere of hydrogen in the presence of Raney-nickel in a solvent such as methanol containing anhydrous ammonia gas will provide compounds of formula 42, which may be treated according to the procedures outlined above to generate compounds of formula (I).

Scheme 11

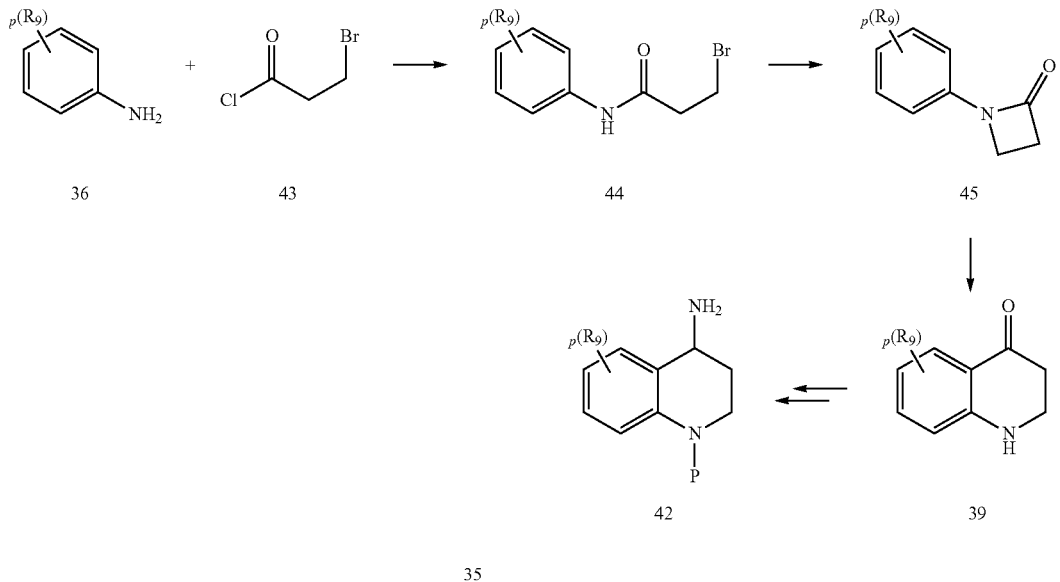

As outlined in Scheme 11, compounds of formula 36 which are representative of heterocycles $Ar_1$, may be prepared accordingly. Alternatively, compounds of formula 36 when treated with compounds of formula 43 in the presence of a base such as potassium carbonate in solvents such as but not limited to dichloromethane or acetonitrile will provide compounds of formula 44. Compounds of formula 44 when treated with sodium tert-butoxide in DMF will provide compounds of formula 45. Compounds of formula 45 when treated with trifluoroacetic acid in dichloroethane under heated conditions will provide compounds of formula 39. Similarly, compounds of formula 39 when treated according to the procedures outlined in Scheme 10 will generate compounds of formula 42, which may be treated according to the procedures outlined above to generate compounds of formula (I).

Scheme 12

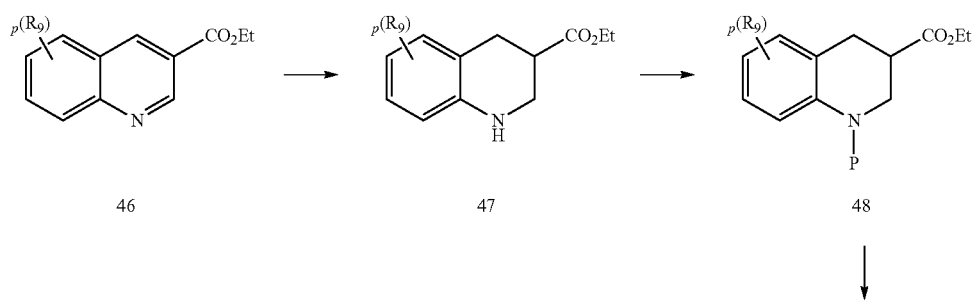

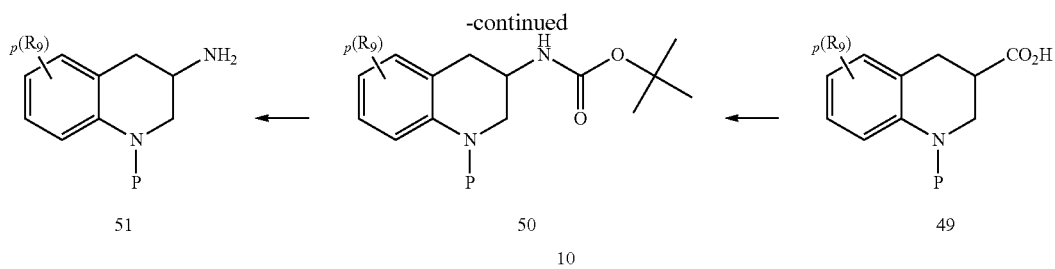

As outlined in Scheme 12, compounds of formula 51 which are representative of heterocycles $Ar_1$, may be prepared accordingly. Compounds of formula 46 which may be obtained through commercial sources or may be generated through methods known to one skilled in the art, wherein $R_9$ and p are as defined above, when heated in the presence of an atmosphere of hydrogen and 10% palladium on carbon in a solvent such as ethanol will generate compounds of formula 47. Compounds of formula 48 when treated with a reagent that will protect an amine functional group as described in Scheme 10 will provide compounds of formula 48. Compounds of formula 48 when treated with sodium, lithium or potassium hydroxide in an aqueous alcoholic solvent will provide compounds of formula 49. Compounds of formula 49 when treated with diphenylphosphoryl azide and triethylamine in tert-butanol under heated conditions will provide compounds of formula 50. Compounds of formula 50 when treated with hydrochloric in acetic acid or trifluoroacetic acid in dichloromethane will provide compounds of formula 51, which may be treated according to the procedures outlined above to generate compounds of formula (I).

conditions will generate compounds of formula 54. The treatment of compounds of formula 54 with lithium aluminum hydride in THF under mild heated conditions will generate compounds of formula 55, which may be treated according to the procedures outlined above to generate compounds of formula (I).

Scheme 14

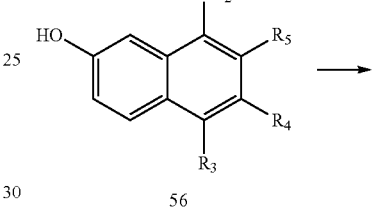

56

Scheme 13

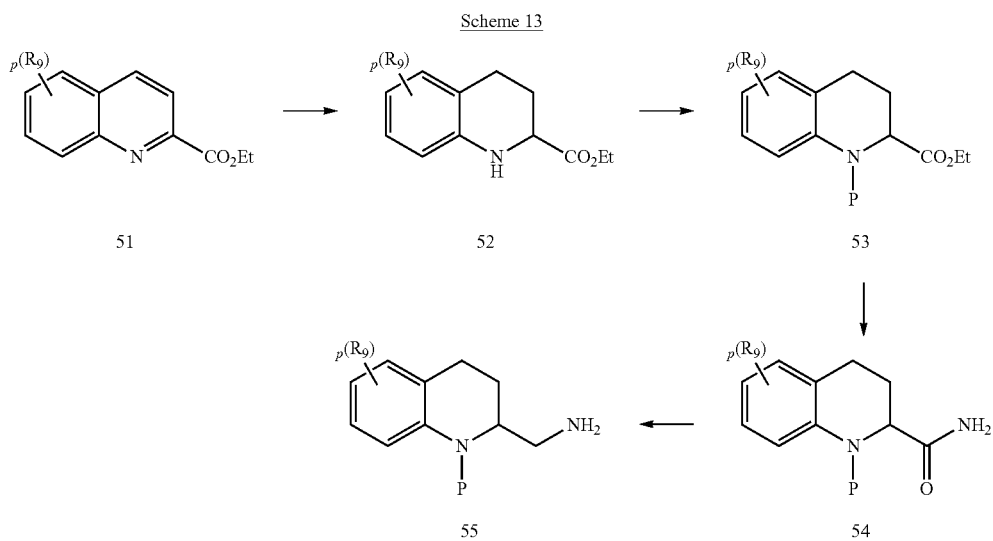

As outlined in Scheme 13, compounds of formula 55 which are representative of heterocycles $Ar_1$, may be prepared accordingly. Similarly, compounds of formula 51 when treated with an atmosphere of hydrogen in the presence of 5% palladium on carbon in a solvent such as acetic acid will provide compounds of formula 52. The amine functional group of compounds of formula 52 may be protected through methods known to one skilled in the art or as described in the literature as listed in Scheme 10, will provide compounds of formula 53. Compounds of formula 53 when treated with ammonia gas in methanol in a sealed vessel under heated -continued

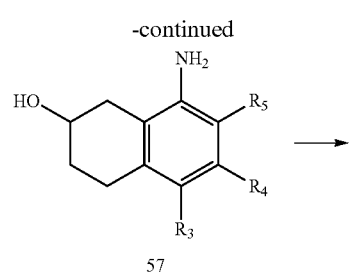

57

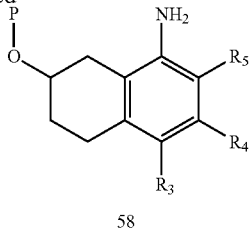

58

As outlined in Scheme 14, compounds of formula compounds of formula 58, wherein $R_3$, $R_4$ and $R_5$ are defined in formula (I), which are used in the preparation of compounds of formula (I) may be obtained from commercial sources or may be prepared accordingly. Compounds of formula 56 which contain both a hydroxyl and an amine functional group when subjected to 1300 psi of hydrogen gas in the presence of Raney-nickel and sodium hydroxide in ethanol at about 80° C. will provide compounds of formula 57. The hydroxyl group of compounds of formula 57 may be protected according to conditions known to one skilled in the art or through methods outlined in T. W. Greene and P. G. M. Wuts, Protective Groups in Organic Synthesis, 3rd edition, John Wiley & Sons, New York (1999) to provide compounds of formula 58, which may be treated according to the procedures outlined above to generate compounds of formula (I).

It is understood that the foregoing schemes are described for illustrative purposes and that routine experimentation, including appropriate manipulation of the sequence of the synthetic route, protection of any chemical functionality that are not compatible with the reaction conditions and the removal of such protecting groups are included in the scope of the application.

EXAMPLES

The following Examples are intended as an illustration of and not a limitation upon the scope of the application as defined in the appended claims.

Example 1

N-(3,4-Dihydro-2H-chromen-3-yl)-N'-(7-hydroxy-5,6,7,8-tetrahydronaphthalen-1-yl)urea

Example 1A

2H-Chromene-3-carbonitrile

A microwave vessel was charged with 2-hydroxybenzaldehyde (Aldrich, 3.0 mL, 28.6 mmol), acrylonitrile (9.4 mL, 143 mmol) and 1,4-diazabicyclo[2.2.2]octane (0.80 g, 7.2 mmol), and heated in a microwave Personal Chemistry at 90° C. for 13 hours. Sodium hydroxide (1N, 200 mL) was added and the mixture was extracted twice with ethyl acetate (200 mL), and the combined organic layer washed with brine, dried with anhydrous sodium sulfate, filtered, and concentrated under reduced pressure. The residue was chromatographed on silica gel eluting with 0-to-20% ethyl acetate in hexane providing the title compound. $^1$H NMR (300 MHz, DMSO-$d_6$) δ ppm 4.88 (d, J=1.36 Hz, 2H), 6.90 (d, J=8.14 Hz, 1H), 7.01 (td, J=7.46, 1.01 Hz, 1H), 7.30 (m, 2H), 7.58 (s, 1H). MS (DCI) m/z 175.05 (M+NH$_4$)$^+$.

Example 1B

2H-Chromene-3-carboxylic acid

Example 1A (3.543 g, 22.5 mmol), 50 w % sodium hydroxide (25 mL) and water (50 mL) were heated to reflux for 4 hours. After cooling to ambient temperature, water was added (500 mL) and the mixture was acidified with 6N hydrochloric acid (80 mL) to precipitate the product. The solids were collected by filtration, rinsed with water, and freeze dried to obtain the title compound. $^1$H NMR (300 MHz, DMSO-$d_6$) δ ppm 4.91 (d, J=1.36 Hz, 2H), 6.84 (d, J=8.14 Hz, 1H), 6.95 (td, J=7.46, 1.01 Hz, 1H), 7.26 (td, J=7.80, 1.70 Hz, 1H), 7.32 (dd, J=7.46, 1.70 Hz, 1H), 7.44 (s, 1H), 12.82 (br s, 1H). MS (EI) m/z 176.10 (M)$^+$.

Example 1C

Chroman-3-one

Example 1B (3.472 g, 19.7 mmol) was dissolved in dichloromethane (45 mL) to which was added triethylamine (3.5 mL) and diphenylphosphoryl azide (5.97 g, 21.7 mmol) in toluene (20 mL). The flask was equipped with a Dean-Stark trap and the mixture was heated to reflux. Toluene (45 mL) was added after one hour and the mixture was reflux for an 2 additional hours after which it was cooled to ambient temperature. 6N hydrochloric acid (50 mL) and toluene (20 mL) were added and the biphasic mixture refluxed for 3.5 hours followed by cooling to ambient temperature. Ethyl acetate (100 mL) and water (100 mL) were added, and the separated organic layer was washed sequentially with saturated sodium bicarbonate (2×100 mL), brine, dried over anhydrous sodium sulfate and filtered. The solution was concentrated under reduced pressure and chromatographed on silica gel eluting with 0-to-40% ethyl acetate in hexane to afford the title compound. $^1$H NMR (300 MHz, DMSO-$d_6$) δ ppm 3.68 (s, 2H), 4.46 (s, 2H), 7.04 (m, 2H), 7.23 (m, 2H). MS (DCI) m/z 148.04 (M+NH$_4$—H$_2$O)$^+$.

Example 1D

Chroman-3-one O-methyl oxime

Methoxylamine hydrochloride (1.23 g, 14.8 mmol) was added to a solution of Example 1C (1.99 g, 13.4 mmol) in pyridine (30 mL) and stirred overnight at ambient temperature. The mixture was concentrated to a yellow residue and ethyl acetate (200 mL) and 1N hydrochloric acid (200 mL) were added. The organic layer was washed with brine, dried with anhydrous sodium sulfate and filtered. The solvent was concentrated under reduced pressure and the residue chromatographed on silica gel eluting with 0-to-20% ethyl acetate in hexane to afford the title compound. $^1$H NMR (300 MHz, DMSO-$d_6$) δ ppm 3.72 (s, 2H), 3.85 (s, 3H), 4.51 (s, 2H), 6.89 (dd, J=8.14, 1.36 Hz, 1H), 6.96 (td, J=7.46, 1.36 Hz, 1H), 7.14 (m, 1H), 7.21 (d, J=7.46 Hz, 1H). MS (DCI) m/z 178.07 (M+H)$^+$.

Example 1E

Chroman-3-amine

Example 1D (2.027 g, 11.4 mmol), Raney nickel (10.0 g), and 20% ammonia in anhydrous methanol (20 mL) were shaken under an atmosphere of hydrogen (60 psi) for 3 hours at ambient temperature. The catalyst was removed by filtration and the solvent evaporated under reduced pressure to afford the title compound. $^1$H NMR (300 MHz, DMSO-$d_6$) δ ppm 1.61 (br s, 2H), 2.46 (dd, J=16.28, 9.16 Hz, 1H), 2.87 (dd, J=15.94, 3.73 Hz, 1H), 3.10 (m, 1H), 3.57 (dd, J=10.17, 8.82 Hz, 1H), 4.06 (ddd, J=10.26, 3.48, 1.86 Hz, 1H), 6.72 (dd, J=8.48, 1.35 Hz, 1H), 6.80 (td, J=7.46, 1.36 Hz, 1H), 7.04 (m, 2H). MS (DCI) m/z 150.07 (M+H)$^+$.

Example 1F

8-Amino-1,2,3,4-tetrahydronaphthalen-2-ol

A hydrogenation reaction vessel was charged with 8-aminonaphthalen-2-ol (Aldrich, 5.0 g, 31.4 mmol), 50% w/w sodium hydroxide (0.2 g, 2.5 mmol) and Raney nickel (slurry in water, 40% weight load, 2.0 g) in ethanol (100 mL). The vessel was purged with hydrogen gas several times before sealing under a hydrogen atmosphere at a pressure of 1300 psi followed by heating to 85° C. After 6 hours the mixture was filtered, and the filtrate was concentrated under reduced pressure to afford the title compound. $^1$H NMR (500 MHz, DMSO-$d_6$) δ ppm 1.44-1.68 (m, 1H), 1.79-1.94 (m, 1H), 2.20 (dd, J=16.48, 7.63 Hz, 1H), 2.56-2.85 (m, 3H), 3.85-3.99 (m, 1H), 4.63 (s, 2H), 4.75 (d, J=4.12 Hz, 1H), 6.30 (d, J=7.48 Hz, 1H), 6.44 (d, J=7.78 Hz, 1H), 6.78 (t, J=7.63 Hz, 1H). $^{13}$C NMR (126 MHz, DMSO-$d_6$) δ ppm 27.35, 31.41, 33.36, 65.81, 111.35, 116.48, 119.13, 125.53, 136.00, 146.12. MS (DCI) m/z 164.06 (M+H)$^+$.

Example 1G 7-(tert-Butyldimethylsilyloxy)-5,6,7,8-tetrahydronaphthalen-1-amine A mixture of Example 1F (2.33 g, 14.3 mmol), tert-butylchlorodimethylsilane (2.6 g, 17.2 mmol) and imidazole (2.9 g, 42.3 mmol) in dichloromethane (40 mL) were stirred at ambient temperature overnight. The mixture was then washed several times with water and once with brine. The organic layer was separated and dried over anhydrous sodium sulfate. Filtration and concentration afforded the title compound. $^1$H NMR (500 MHz, DMSO-$d_6$) δ ppm 0.09 (s, 6H), 0.88 (s, 9H), 1.63 (m, 1H), 1.82 (m, 1H), 2.24 (m, 1H), 2.75 (m, 3H), 4.11 (m, 1H), 4.7 (br s, 2H), 6.28 (d, J=7.4 Hz, 1H), 6.42 (d, J=7.8 Hz, 1H), 6.77 (dd, J=7.8, 7.4 Hz, 1H). MS (ESI) m/z 278 (M+H)$^+$.

Example 1H

N-(3,4-Dihydro-2H-chromen-3-yl)-N'-(7-hydroxy-5,6,7,8-tetrahydronaphthalen-1-yl)urea To di-(N-succinimidyl) carbonate (Fluka, 538 mg, 2.1 mmol) in acetonitrile (5 mL) was added Example 1G (555 mg, 2.0 mmol) in acetonitrile (10 mL) and pyridine (0.17 mL, 2.1 mmol). The mixture was stirred for 15 minutes at ambient temperature. Example 1E (298 mg, 2.0 mmol) and diisopropylethylamine (1.05 mL, 6.0 mmol) were added and the mixture stirred for 30 minutes. The mixture was filtered through a silica gel plug, rinsed with 1/1 ethyl acetate/hexane and concentrated under reduced pressure to afford 1-(7-(tert-butyldimethylsilyloxy)-5,6,7,8-tetrahydronaphthalen-1-yl)-3-(chroman-3-yl)-urea. This intermediate was dissolved in tetrahydrofuran (20 mL), tetrabutylammonium fluoride (1.0M in THF, 6.0 mL, 6.0 mmol) was added, and the mixture stirred overnight at ambient temperature. The mixture was concentrated under reduced pressure and chromatographed on silica gel eluting with ethyl acetate and concentrated under reduced pressure. The residue was dissolved in ethyl acetate (200 mL) and washed sequentially with 1N sodium hydroxide (200 mL), water (200 mL) and brine. The organic layer was dried with anhydrous sodium sulfate, filtered, concentrated under reduced pressure and vacuum dried overnight to afford the title compound. $^1$H NMR (300 MHz, DMSO-$d_6$) δ ppm 1.56 (m, 1H), 1.84 (m, 1H), 2.27 (m, 1H), 2.74 (m, 4H), 3.09 (dd, J=16.95, 3.09 Hz, 1H), 3.89 (m, 1H), 4.02 (m, 1H), 4.12 (m, 2H), 4.82 (d, J=4.07 Hz, 1H), 6.69 (d, J=7.12 Hz, 1H), 6.85 (m, 3H), 6.97 (t, J=7.80 Hz, 1H), 7.11 (m, 2H), 7.61 (s, 1H), 7.69 (d, J=7.46 Hz, 1H). MS (ESI) m/z 339.10 (M+H)$^+$. Calcd for $C_{20}H_{22}N_2O_3$.0.15 EtOAc: C, 70.37; H, 6.65; N, 7.97. Found: C, 70.34; H, 6.70; N, 8.04.

Example 2

N-(8-tert-Butyl-3,4-dihydro-2H-chromen-3-yl)-N'-(7-hydroxy-5,6,7,8-tetrahydronaphthalen-1-yl)urea

Example 2A 8-tent-Butyl-2H-chromene-3-carbonitrile 3-tert-butyl-2-hydroxybenzaldehyde (Aldrich, 4.0 mL, 23.4 mmol), acrylonitrile (7.7 mL, 117 mmol), and 1,4-diazabicyclo[2.2.2]octane (0.66 g, 5.8 mmol) were heated in a microwave Personal Chemistry at 95° C. for 5 hours. Sodium hydroxide (1N, 200 mL) was added and the mixture was extracted twice with ethyl acetate (200 mL). The combined organic layers were washed with brine, dried over anhydrous sodium sulfate, filtered, and concentrate under reduced pressure. The residue was chromatographed on silica gel eluting with 0-to-30% ethyl acetate in hexane to afford the title compound. $^1$H NMR (300 MHz, DMSO-$d_6$) δ ppm 1.31 (s, 9H), 4.85 (d, J=1.36 Hz, 2H), 6.97 (t, J=7.63 Hz, 1H), 7.16 (dd, J=7.63, 1.53 Hz, 1H), 7.29 (dd, J=7.80, 1.70 Hz, 1H), 7.58 (s, 1H). MS (DCI) m/z 231.10 (M+NH$_4$)$^+$.

Example 2B 8-tent-Butyl-2H-chromene-3-carboxylic acid

Example 2A (2.25 g, 12.0 mmol), 50 w % sodium hydroxide (25 mL), water (75 mL) and ethanol (50 mL) were heated at reflux for 6 hours. The mixture was cooled, water (500 mL) was added and the mixture was acidified with 6N hydrochloric acid (80 mL) to afford a precipitate. The mixture was filtered, rinsed with water, and freeze-dried to afford the title compound. $^1$H NMR (300 MHz, DMSO-$d_6$) δ ppm 1.32 (s, 9H), 4.86 (d, J=1.36 Hz, 2H), 6.91 (t, J=7.63 Hz, 1H), 7.21 (dd, J=11.53, 1.70 Hz, 1H), 7.23 (dd, J=11.70, 1.53 Hz, 1H), 7.43 (t, J=1.19 Hz, 1H), 12.79 (br s, 1H). MS (DCI) m/z 250.10 (M+NH$_4$)$^+$.

Example 2C 8-tent-Butylchroman-3-one

Example 2B (3.865 g, 16.6 mmol) was dissolved in dichloromethane (45 mL). Triethylamine (3.5 mL) and diphenylphosphoryl azide (5.04 g, 18.3 mmol) in toluene (20 mL) were added. The flask was equipped with a Dean-Stark trap and heated to reflux. Toluene (45 mL) was added after one hour, and the mixture continued to reflux for 1.5 additional hours after which it was allowed to cool to ambient temperature. Hydrochloric acid (6N, 50 mL) and toluene (10 mL)

were added and the biphasic mixture was heated at reflux for 2 hours then cooled to ambient temperature. Ethyl acetate (100 mL) and water (100 mL) were added, and the organic layer was washed twice with saturated sodium bicarbonate (100 mL), then with brine, dried over anhydrous sodium sulfate and filtered concentrated under reduced pressure and purified on silica gel eluting with 0-to-30% ethyl acetate in hexane afforded the title compound. $^1$H NMR (300 MHz, DMSO-d$_6$) δ ppm 1.36 (s, 9H), 3.66 (s, 2H), 4.43 (s, 2H), 6.99 (t, J=7.63 Hz, 1H), 7.08 (dd, J=7.29, 1.19 Hz, 1H), 7.19 (dd, J=7.80, 1.36 Hz, 1H). MS (DCI) m/z 204.10 (M+NH$_4$—H$_2$O)$^+$.

Example 2D 8-tent-Butylchroman-3-one O-methyl oxime

Methoxylamine hydrochloride (1.15 g, 13.7 mmol) was added to a solution of Example 2C (2.547 g, 12.5 mmol) in pyridine (30 mL) and the mixture was stirred overnight at ambient temperature. The mixture was concentrated under reduced pressure, and ethyl acetate (200 mL) and 1N hydrochloric acid (200 mL) were added. The separated organic layer was washed with brine, dried over anhydrous sodium sulfate, filtered and concentrated under reduced pressure. The residue was chromatographed on silica gel eluting with 0-to-20% ethyl acetate in hexane to afford the title compound. MS (DCI) m/z 234.12 (M+H)$^+$.

Example 2E 8-tent-Butylchroman-3-amine

Example 2D (1.870 g, 8.02 mmol), Raney nickel (9.0 g), and 20% ammonia in methanol (40 mL) were shaken under hydrogen (60 psi) for 3 hours at ambient temperature. The catalyst was removed by filtration and the solvent was removed under reduced pressure to afford the title compound. $^1$H NMR (300 MHz, DMSO-d$_6$) δ ppm 1.31 (s, 9H), 1.63 (br s, 2H), 2.46 (m, 1H), 2.89 (m, 1H), 3.09 (m, 1H), 3.56 (dd, J=10.17, 8.82 Hz, 1H), 4.14 (ddd, J=10.26, 3.31, 1.70 Hz, 1H), 6.73 (t, J=7.46 Hz, 1H), 6.88 (d, J=6.10 Hz, 1H), 7.00 (dd, J=7.63, 1.53 Hz, 1H). MS (DCI) m/z 206.08 (M+H)$^+$.

Example 2F

N-(8-tert-Butyl-3,4-dihydro-2H-chromen-3-yl)-N'-(7-hydroxy-5,6,7,8-tetrahydronaphthalen-1-yl)urea To di-(N-succinimidyl) carbonate (538 mg, 2.1 mmol) in acetonitrile (5 mL) was added Example 1G (555 mg, 2.0 mmol) in acetonitrile (10 mL) and pyridine (0.17 mL, 2.1 mmol). The mixture was stirred for 15 minutes at ambient temperature. Example 2E (411 mg, 2.0 mmol) and diisopropylethylamine (1.05 mL, 6.0 mmol) were added and the mixture stirred for an additional 30 minutes. The mixture was filtered through a silica gel plug, rinsed with 1/1 ethyl acetate/hexane, and concentrated under reduced pressure to afford 1-(8-tert-butylchroman-3-yl)-3-(7-(tert-butyldimethylsilyloxy)-5,6,7,8-tetrahydronaphthalen-1-yl)urea. The intermediate was dissolved in tetrahydrofuran (20 mL) followed by the addition of tetrabutylammonium fluoride (1.0M in THF, 6.0 mL, 6.0 mmol) and the mixture stirred overnight at ambient temperature. Ethyl acetate (200 mL) was added and the organic layer was washed sequentially with 1N sodium hydroxide (200 mL), water (200 mL), and brine. The organic layer was dried over anhydrous sodium sulfate, filtered, and concentrated under reduced pressure. The residue was chromatographed on silica gel eluting with 0-to-5% methanol in ethyl acetate to afford the title compound. $^1$H NMR (300 MHz, DMSO-d$_6$) δ ppm 1.34 (s, 9H), 1.58 (m, 1H), 1.85 (m, 1H), 2.29 (dd, J=16.28, 7.80 Hz, 1H), 2.72 (m, 4H), 3.11 (dd, J=16.28, 5.43 Hz, 1H), 3.90 (m, 1H), 3.98 (m, 1H), 4.10 (m, 1H), 4.17 (d, J=10.17 Hz, 1H), 4.82 (d, J=3.73 Hz, 1H), 6.71 (d, J=8.14 Hz, 1H), 6.74 (dd, J=7.12, 3.05 Hz, 1H), 6.80 (t, J=7.63 Hz, 1H), 6.96 (dd, J=7.46, 1.36 Hz, 1H), 6.98 (t, J=7.80 Hz, 1H), 7.06 (dd, J=7.80, 1.70 Hz, 1H), 7.66 (m, 2H). MS (ESI) m/z 395.24 (M+H)$^+$. Calcd for C$_{24}$H$_{30}$N$_2$O$_3$.0.09H$_2$O: C, 72.77; H, 7.68; N, 7.07. Found: C, 72.79; H, 7.79; N, 7.08.

Example 3

N-(7-Hydroxy-5,6,7,8-tetrahydronaphthalen-1-yl)-N'-(7-methoxy-3,4-dihydro-2H-chromen-3-yl)urea Example 3A 7-Methoxy-2H-chromene-3-carbonitrile 2-Hydroxy-4-methoxybenzaldehyde (Aldrich, 5.0 g, 32.9 mmol), acrylonitrile (11 mL, 164 mmol), and 1,4-diazabicyclo[2.2.2]octane (0.92 g, 8.2 mmol) were heated in a microwave Personal Chemistry at 95° C. for 5 hours. Sodium hydroxide (200 mL) was added and the mixture was extracted with ethyl acetate (200 mL) and brine. The organic layer was dried over anhydrous sodium sulfate, filtered, and concentrated under reduced pressure. Chromatography on silica gel eluting with 0-to-50% ethyl acetate in hexane afforded the title compound. $^1$H NMR (300 MHz, DMSO-d$_6$) δ ppm 3.77 (s, 3H), 4.84 (d, J=1.36 Hz, 2H), 6.50 (d, J=2.71 Hz, 1H), 6.61 (dd, J=8.48, 2.71 Hz, 1H), 7.21 (d, J=8.48 Hz, 1H), 7.52 (s, 1H). MS (DCI) m/z 205.07 (M+NH$_4$)$^+$.

Example 3B

7-Methoxy-2H-chromene-3-carboxylic acid

Example 3A (2.25 g, 12.0 mmol), 50 w % sodium hydroxide (25 mL), water (50 mL), and ethanol (25 mL), were heated to reflux for 3 hours. The mixture was cooled and water (300 mL) was added. The mixture was acidified with 1N hydrochloric acid (100 mL) to afford a precipitate. The mixture was filtered and the solids were rinsed with water and freeze-dried to afford the title compound. $^1$H NMR (300 MHz, DMSO-d$_6$) δ ppm 3.75 (s, 3H), 4.87 (d, J=1.36 Hz, 2H), 6.45 (d, J=2.71 Hz, 1H), 6.55 (dd, J=8.31, 2.54 Hz, 1H), 7.25 (d, J=8.48 Hz, 1H), 7.41 (s, 1H), 12.62 (br s, 1H). MS (DCI) m/z 206.87 (M+H)$^+$.

Example 3C

7-Methoxychroman-3-one

Example 3B (1.928 g, 9.35 mmol) was dissolved in dichloromethane (25 mL) followed by the addition of triethylamine (1.7 mL) and diphenylphosphoryl azide (2.83 g, 10.3 mmol) in toluene (10 mL). The flask was equipped with a Dean-Stark trap and the solution was refluxed. After one hour, toluene (25 mL) was added, and the mixture continued to reflux for 2 hours followed by cooling to ambient temperature. Hydrochloric acid (6N, 20 mL), was added and the mixture was heated to reflux for an additional 3 hours after which it was cooled. Ethyl acetate (100 mL) and water (100 mL) were added, and the separated organic layer was washed twice with saturated sodium bicarbonate (100 mL), once with brine, dried over anhydrous sodium sulfate and filtered. Concentration under reduced pressure and chromatography on silica gel eluting with 40-to-90% dichloromethane in hexane afforded the title compound. $^1$H NMR (300 MHz, DMSO-$d_6$) δ ppm 3.59 (s, 2H), 3.73 (s, 3H), 4.44 (s, 2H), 6.64 (m, 2H), 7.10 (d, J=8.82 Hz, 1H). MS (DCI) m/z 178.99 (M+H)$^+$.

Example 3D

7-Methoxychroman-3-one O-methyl oxime

Methoxyl amine hydrochloride (459 mg, 5.49 mmol) was added to a solution of Example 3C (890 mg, 4.99 mmol) in pyridine (20 mL) and the mixture was stirred overnight at ambient temperature. The mixture was concentrated under reduced pressure, taken up in ethyl acetate (100 mL) and 1N hydrochloric acid (100 mL). The separated organic layer was washed with brine, filtered, and dried over anhydrous sodium sulfate. Concentration and chromatography on silica gel eluting with 0-to-20% ethyl acetate in hexane afforded the title compound. $^1$H NMR (300 MHz, DMSO-$d_6$) δ ppm 3.64 (s, 2H), 3.70 (s, 3H), 3.85 (s, 3H), 4.49 (s, 2H), 6.47 (d, J=2.72 Hz, 1H), 6.57 (dd, J=8.48, 2.38 Hz, 1H), 7.10 (d, J=8.48 Hz, 1H). MS (DCI) m/z 208.05 (M+H)$^+$.

Example 3E

7-Methoxychroman-3-amine

Example 3D (829 mg, 4.0 mmol), Raney nickel (5.0 g) and 20% ammonia in methanol (30 mL) were shaken under hydrogen (60 psi) for 3 hours at ambient temperature. The catalyst was removed by filtration and the solvent was evaporated under reduced pressure affording the title compound. $^1$H NMR (300 MHz, DMSO-$d_6$) δ ppm 1.61 (br s, 2H), 2.37 (dd, J=15.43, 8.99 Hz, 1H), 2.79 (dd, J=15.43, 4.24 Hz, 1H), 3.06 (m, 1H), 3.54 (dd, J=10.18, 8.82 Hz, 1H), 3.67 (s, 3H), 4.04 (ddd, J=10.26, 3.31, 1.70 Hz, 1H), 6.30 (d, J=2.71 Hz, 1H), 6.41 (dd, J=8.31, 2.54 Hz, 1H), 6.92 (d, J=8.48 Hz, 1H). MS (DCI) m/z 180.07 (M+H)$^+$.

Example 3F

N-(7-Hydroxy-5,6,7,8-tetrahydronaphthalen-1-yl)-N'-(7-methoxy-3,4-dihydro-2H-chromen-3-yl)urea To a suspension of di(Ar-succinimidyl) carbonate (409 mg, 1.60 mmol) in acetonitrile (5 mL) was added Example 1G (422 mg, 1.52 mmol) in acetonitrile (10 mL) and pyridine (0.13 mL, 1.60 mmol). After 15 minutes at ambient temperature, Example 3E (272 mg, 1.52 mmol) and diisopropylethylamine (0.79 mL, 4.56 mmol) were added and the mixture stirred for 30 minutes. The mixture was filtered through a silica gel plug, rinsed with 1/1 ethyl acetate/hexane, and concentrated under reduced pressure to afford 1-(7-(tert-butyldimethylsilyloxy)-5,6,7,8-tetrahydronaphthalen-1-yl)-3-(7-methoxychroman-3-yl)urea. The residue was dissolved in tetrahydrofuran (30 mL), tetrabutylammonium fluoride (1.0M in THF, 3.04 mL, 3.04 mmol) was added and the mixture stirred overnight at ambient temperature. The mixture was concentrated under reduced pressure and the residue was chromatographed on silica gel eluting with 0-to-10% methanol in ethyl acetate. The resulting solid was suspended in methanol (20 mL) which was sonicated after which water (200 mL) was added. The sonication was repeated and the solids were collected by filtration, rinsed with water, and freeze-dried to afford the title compound. $^1$H NMR (300 MHz, DMSO-$d_6$) δ ppm 1.56 (m, 1H), 1.84 (m, 1H), 2.28 (m, 1H), 2.59 (m, 1H), 2.76 (m, 1H), 3.00 (dd, J=16.10, 5.26 Hz, 1H), 3.70 (s, 3H), 3.89 (m, 1H), 4.01 (m, 1H), 4.10 (m, 2H), 4.82 (d, J=4.07 Hz, 1H), 6.40 (d, J=2.37 Hz, 1H), 6.49 (dd, J=8.31, 2.54 Hz, 1H), 6.69 (d, J=7.46 Hz, 1H), 6.85 (d, J=7.46 Hz, 1H), 6.97 (t, J=7.80 Hz, 1H), 7.00 (d, J=8.14 Hz, 1H), 7.61 (s, 1H), 7.69 (d, J=7.46 Hz, 1H). MS (ESI) m/z 369.16 (M+H)$^+$. Calcd for $C_{21}H_{24}N_2O_4 \cdot 0.17H_2O$: C, 67.90; H, 6.60; N, 7.54. Found: C, 67.92; H, 6.67; N, 7.41.

Example 4

N-(6-Chloro-3,4-dihydro-2H-chromen-3-yl)-N'-(7-hydroxy-5,6,7,8-tetrahydronaphthalen-1-yl)urea Example 4A 6-Chlorochroman-3-one To a solution of 6-chloro-2H-chromene-3-carboxylic acid (Avocado, 4.90 g, 23.3 mmol) in dichloromethane (50 mL) was added triethylamine (4 mL) and diphenylphosphoryl azide (7.04 g, 25.6 mmol) in toluene (20 mL). The flask was equipped with a Dean-Stark trap, and the mixture was heated to reflux. After 1.5 hours, toluene (50 mL) was added and the mixture continued to reflux for 2.5 hours and was then cooled to ambient temperature. Hydrochloric acid (6N, 40 mL) was added, and the biphasic mixture was heated at reflux for 3.5 hours then cooled to ambient temperature. Ethyl acetate (200 mL) and water (200 mL) were added and the separated organic layer was washed sequentially with saturated sodium bicarbonate (2×200 mL) followed by brine. The organic layer was dried over anhydrous sodium sulfate, filtered, concentrate under reduced pressure, and chromatographed on silica gel eluting with 10-to-60% dichloromethane in hexane to afford the title compound. MS (DCI) m/z 181.97 (M+H)$^+$.

Example 4B

6-Chlorochroman-3-amine

Example 4A (1.29 g, 7.06 mmol) was dissolved in isopropyl alcohol (125 mL) and ammonium acetate (16.34 g, 212 mmol) was added. The mixture was stirred for one hour at ambient temperature. Sodium cyanoborohydride (1.55 g, 24.7 mmol) was added and the mixture refluxed for one hour, and was cooled. After quenching with 3N sodium hydroxide (70 mL), the mixture was extracted twice with text-butyl methyl ether (100 mL), and concentrate under reduced pressure. Ethyl acetate (100 mL) was added, and the mixture was extracted with 1N hydrochloric acid (3×70 mL). The acidic aqueous extracts were combined, and 3N sodium hydroxide (90 mL) was added. The resulting aqueous solution was extracted twice with ethyl acetate (200 mL). The three ethyl acetate layers were combined and washed with brine, dried over anhydrous sodium sulfate, filtered and concentrated under reduced pressure to afford the title compound. $^1$H NMR (300 MHz, DMSO-$d_6$) δ ppm 1.71 (br s, 2H), 2.46 (dd, J=15.94, 8.48 Hz, 1H), 2.88 (dd, J=15.26, 4.75 Hz, 1H), 3.09 (m, 1H), 3.60 (dd, J=10.85, 8.48 Hz, 1H), 4.07 (ddd, J=10.43, 3.48, 2.03 Hz, 1H), 6.75 (d, J=8.81 Hz, 1H), 7.08 (dd, J=8.48, 2.71 Hz, 1H), 7.12 (m, 1H). MS (DCI) m/z 184.01 (M+H)$^+$.

Example 4C

N-(6-Chloro-3,4-dihydro-2H-chromen-3-yl)-N'-(7-hydroxy-5,6,7,8-tetrahydronaphthalen-1-yl)urea Di(N-succinimidyl) carbonate (546 mg, 2.13 mmol) was suspended in acetonitrile (5 mL) followed by the addition of Example 1G (563 mg, 2.03 mmol) in acetonitrile (5 mL) and pyridine (0.17 mL, 2.13 mmol). The mixture stirred for 15 minutes at ambient temperature followed by the addition of Example 4B (373 mg, 2.03 mmol) in acetonitrile (10 mL) and diisopropylethylamine (1.06 mL, 6.09 mmol). The mixture stirred for 30 minutes was concentrated under reduced pressure and chromatographed on silica gel eluting with 0-to-40% ethyl acetate in hexane to afford 1-(7-(tert-butyldimethylsilyloxy)-5,6,7,8-tetrahydronaphthalen-1-yl)-3-(6-chlorochroman-3-yl)urea. The intermediate was dissolved in tetrahydrofuran (30 mL), and tetrabutylammonium fluoride (1.0M in THF, 4.06 mL, 4.06 mmol) was added, and the mixture stirred overnight at ambient temperature. The mixture was concentrated under reduced pressure and chromatographed on silica gel eluting with 0-to-10% methanol in ethyl acetate. The residue was dissolved in methanol (20 mL), sonicated and water (200 mL) was added. The sonication was repeated, and the solids were collected by filtration, rinsed with water, and freeze-dried to afford the title compound. $^1$H NMR (300 MHz, DMSO-$d_6$) δ ppm 1.57 (m, 1H), 1.83 (m, 1H), 2.27 (dd, J=16.45, 7.63 Hz, 1H), 2.74 (m, 4H), 3.10 (dd, J=16.95, 4.74 Hz, 1H), 3.88 (m, 1H), 4.09 (m, 3H), 4.81 (d, J=4.07 Hz, 1H), 6.69 (d, J=7.46 Hz, 1H), 6.86 (m, 2H), 6.98 (t, J=7.80 Hz, 1H), 7.15 (dd, J=8.81, 2.71 Hz, 1H), 7.21 (d, J=2.71 Hz, 1H), 7.58 (s, 1H), 7.69 (d, J=7.80 Hz, 1H). MS (ESI) m/z 373.11 (M+H)$^+$. Calcd for $C_{20}H_{21}Cl_1N_2O_3 \cdot 0.78H_2O$: C, 62.09; H, 5.88; N, 7.24. Found: C, 62.09; H, 5.90; N, 7.19.

Example 5

N-(8-tert-Butyl-3,4-dihydro-2H-chromen-4-yl)-N'-(7-hydroxy-5,6,7,8-tetrahydronaphthalen-1-yl)urea

Example 5A 1-text-Butyl-2-(prop-2-ynyloxy)benzene 2-tert-butylphenol (Aldrich, 15.02 g, 15.4 ml, 100 mmol), propargyl bromide (80% in toluene, 14.3 ml, 128 mmol) and potassium carbonate (17.66 g, 128 mmol) were stirred together in acetonitrile (200 mL) for 5 days at ambient temperature. The solvent was removed under reduced pressure, and the residue taken into water and extracted with diethyl ether. The organic layers were combined, dried with magnesium sulfate, filtered, and the solvent evaporated under reduced pressure to afford the title compound. $^1$H NMR (300 MHz, CDCl$_3$) δ ppm 1.39 (s, 9H), 2.48 (t, J=2.37 Hz, 1H), 4.73 (d, J=2.37 Hz, 2H), 6.90-6.98 (m, 2H), 7.15-7.22 (m, 1H), 7.30 (dd, J=7.80, 1.70 Hz, 1H). MS (DCI) m/z 206 (M+NH$_4$)$^+$.

Example 5B 1-tent-Butyl-2-(3-chloroprop-2-ynyloxy)benzene

To a solution of Example 5A (18.86 g, 100 mmol) in acetone (400 mL) was added N chlorosuccinimide (16.02 g, 120 mmol) and silver acetate (1.67 g, 10 mmol) and the mixture was heated at reflux for 4 hours. After cooling, the silver salts were removed by filtration and the filtrate evaporated under reduced pressure. The residue was taken up in diethyl ether, washed with water and saturated aqueous sodium bicarbonate, dried with magnesium sulfate, filtered, and the solvent was removed under reduced pressure to afford the title compound. $^1$H NMR (300 MHz, CDCl$_3$) δ ppm 1.38 (s, 9H), 4.73 (s, 2H), 6.91-6.97 (m, 2H), 7.19 (td, J=7.71, 1.86 Hz, 1H), 7.30 (dd, J=7.97, 1.53 Hz, 1H). MS (DCI) m/z 223 (M+H)$^+$.

Example 5C 8-tert-Butylchroman-4-one

Example 5B (25.8 g) in ethylene glycol (250 mL) was heated to reflux for 4 hours. The mixture was cooled, poured into water, and extracted with diethyl ether. The organic layers were combined, washed sequentially with 1N sodium hydroxide and saturated ammonium carbonate, dried with magnesium sulfate, and filtered. Removal of solvent under reduced pressure gave a residue which was taken up in 1/1 dichloromethane/hexane and filtered through a pad of silica gel. The filtrate was evaporated under reduced pressure to afford the title compound. $^1$H NMR (300 MHz, CDCl$_3$) δ ppm 1.39 (s, 9H), 2.79-2.85 (m, 2H), 4.51-4.58 (m, 2H), 6.95 (t, J=7.80 Hz, 1H), 7.47 (dd, J=7.63, 1.86 Hz, 1H), 7.81 (dd, J=7.80, 1.70 Hz, 1H). MS (DCI) m/z 205 (M+H)$^+$.

Example 5D 8-tert-Butylchroman-4-one O-methyl oxime

Example 5C (13.51 g, 66 mmol) was dissolved in pyridine (100 mL). Methoxyl amine hydrochloride (10 g, 120 mmol) was added and the mixture stirred for 16 hours at ambient temperature. The pyridine was removed under reduced pressure, and the residue partitioned between water and diethyl ether. The aqueous layer was extracted with diethyl ether, and the combined organic layers were washed with 1N sodium hydroxide and 1N hydrochloric acid, dried with magnesium sulfate, and filtered. The solvent was removed under reduced pressure afford the title compound. $^1$H NMR (300 MHz, CDCl$_3$) δ ppm 1.36 (s, 9H), 2.91 (t, J=6.27 Hz, 2H), 3.98 (s, 3H), 4.18 (t, J=6.27 Hz, 2H), 6.87 (t, J=7.80 Hz, 1H), 7.21-7.27 (m, 1H), 7.79 (dd, J=7.80, 1.70 Hz, 1H). MS (DCI) m/z 234 (M+H)$^+$.

Example 5E 8-tert-Butylchroman-4-amine

Example 5D (14.44 g, 61.9 mmol), 10% palladium on carbon (1.5 g), and 20% ammonia in methanol (400 mL) were shaken under hydrogen (60 psi) for 2.5 hours at ambient temperature. The catalyst was removed by filtration and the solvent evaporated under reduced pressure to afford the title compound. $^1$H NMR (300 MHz, CDCl$_3$) δ ppm 1.34-1.37 (m, 9H), 1.90 (td, J=9.16, 4.07 Hz, 1H), 2.10-2.25 (m, 1H), 4.11 (t, J=5.09 Hz, 1H), 4.22-4.29 (m, 2H), 6.81-6.89 (m, 1H), 7.14-7.24 (m, 2H). MS (DCI) m/z 206 (M+H)$^+$.

Example 5F

N-(8-tert-Butyl-3,4-dihydro-2H-chromen-4-yl)-N'-(7-hydroxy-5,6,7,8-tetrahydronaphthalen-1-yl)urea To a solution of di(N-succinimidyl) carbonate (408 mg, 1.59 mmol) in acetonitrile (5 mL) was added Example 1G (421 mg, 1.52 mmol) dissolved in acetonitrile (5 mL) and pyridine (0.13 mL, 1.59 mmol) and the mixture stirred for 15 minutes at ambient temperature. Example 5E (311 mg, 1.52 mmol) dissolved in acetonitrile (10 mL) and diisopropylethylamine (0.79 mL, 4.55 mmol) was added and the mixture stirred for 30 minutes. The mixture was filtered through a silica gel plug, rinsed with 1/1 ethyl acetate/hexane, and the supernatant solution was concentrated under reduced pressure to afford 1-(8-tert-butylchroman-4-yl)-3-(7-(tert-butyldimethylsilyloxy)-5,6,7,8-tetrahydronaphthalen-1-yl) urea. The intermediate was dissolved in tetrahydrofuran (30 mL), tetrabutylammonium fluoride (1.0M in THF, 3.0 mL, 3.0 mmol) was added and the mixture stirred overnight at ambient temperature. The mixture was concentrated under reduced pressure to an oil, chromatographed on silica gel eluting with 0-to-10% methanol in ethyl acetate, and concentrate under reduced pressure. The residue was dissolved in methanol (25 mL), precipitated with water (250 mL), and sonicated. The solids were collected by filtration, rinsed with water, and freeze-dried overnight to afford the title compound. $^1$H NMR (300 MHz, DMSO-$d_6$) δ ppm 1.34 (s, 9H), 1.57 (m, 1H), 1.85 (m, 1H), 1.95 (m, 1H), 2.08 (m, 1H), 2.27 (dd, 1H), 2.73 (m, 3H), 3.91 (m, 1H), 4.11 (td, 1H), 4.34 (dt, 1H), 4.82 (q, 1H), 4.83 (d, 1H), 6.69 (d, 1H), 6.84 (t, 1H), 7.00 (t, 1H), 7.14 (m, 3H), 7.43 (s, 1H), 7.74 (d, 1H). MS (ESI) m/z 395.18 (M+H)$^+$. Calcd for $C_{24}H_{30}N_2O_3 \cdot 0.29H_2O$: C, 72.11; H, 7.71; N, 7.01. Found: C, 72.15; H, 8.03; N, 6.92.

Example 6

N-(3,4,7,8,9,10-Hexahydro-2H-benzo[h]chromen-4-yl)-N'-(7-hydroxy-5,6,7,8-tetrahydronaphthalen-1-yl)urea Example 6A 5-(Prop-2-ynyloxy)-1,2,3,4-tetrahydronaphthalene 5,6,7,8-Tetrahydronaphthalen-1-ol (Aldrich, 3.93 g, 26.5 mmol), propargyl bromide (80% in toluene, 3.9 ml, 35 mmol), and potassium carbonate (4.83 g, 35 mmol) were stirred together in acetonitrile (75 mL) for 6 days at ambient temperature. The solvent was removed under reduced pressure, and the residue taken into water and extracted with diethyl ether. The organic layers were combined, dried with magnesium sulfate, filtered, and the solvent was evaporated under reduced pressure to afford the title compound. $^1$H NMR (300 MHz, CDCl$_3$) δ ppm 1.76 (m, 4H), 2.49 (t, J=2.37 Hz, 1H), 2.68 (t, J=5.59 Hz, 2H), 2.75 (t, J=5.59 Hz, 2H), 4.69 (d, J=2.37 Hz, 2H), 6.74 (dd, J=7.80, 3.73 Hz, 2H), 7.06 (t, J=7.80 Hz, 1H). MS (DCI) m/z 187.06 (M+H)$^+$.

Example 6B 5-(3-Chloroprop-2-ynyloxy)-1,2,3,4-tetrahydronaphthalene

Example 6A (5.41 g) was dissolved in acetone (120 mL). N chlorosuccinimide (4.00 g, 30 mmol) and silver acetate (0.42 g, 2.5 mmol) were added, and the mixture was refluxed for 4 hours. After cooling, the silver salts were removed by filtration and the filtrate was evaporated under reduced pressure. The residue was taken up in diethyl ether, washed with water and saturated aqueous sodium bicarbonate, dried with magnesium sulfate, filtered, and concentrated under reduced pressure to afford a mixture of starting material and product. The reaction procedure was repeated with this mixture, affording the title compound. $^1$H NMR (300 MHz, CDCl$_3$) δ ppm 1.76 (m, 4H), 2.66 (t, J=5.59 Hz, 2H), 2.75 (t, J=5.43 Hz, 2H), 4.69 (s, 2H), 6.73 (t, J=7.12 Hz, 2H), 7.07 (t, J=7.97 Hz, 1H). MS (DCI) m/z 220.99 (M+H)$^+$.

Example 6C 7,8,9,10-Tetrahydro-2H-benzo[h]chromen-4(3H)-one

Example 6B (4.80 g, 21.7 mmol) in ethylene glycol (50 mL) was heated to reflux for 4.5 hours. The mixture was cooled, poured into water, and extracted with diethyl ether. The organic layers were combined, washed with 1N sodium hydroxide and with saturated ammonium carbonate, and dried with magnesium sulfate. Removal of the solvent under reduced pressure gave a residue which was filtered through a pad of silica gel eluting with 1/1 dichloromethane/hexane. The filtrate was evaporated under reduced pressure to afford the title compound. $^1$H NMR (300 MHz, CDCl$_3$) δ ppm 1.78 (m, 4H), 2.63 (t, J=5.59 Hz, 2H), 2.76 (t, J=6.44 Hz, 4H), 4.53 (t, J=6.44 Hz, 2H), 6.74 (d, J=8.14 Hz, 1H), 7.65 (d, J=8.14 Hz, 1H). MS (DCI) m/z 203.07 (M+H)$^+$.

Example 6D 7,8,9,10-Tetrahydro-2H-benzo[h]chromen-4(3H)-one O-methyl oxime

Example 6C (5.00 g) was dissolved in pyridine (30 mL). Methoxyl amine hydrochloride (2.09 g, 25 mmol) was added and the mixture stirred for 16 hours at ambient temperature. The pyridine was removed under reduced pressure, and the residue partitioned between water and diethyl ether. The aqueous layer was extracted with diethyl ether, and the combined organic layers were washed with 1N sodium hydroxide and 1N hydrochloric acid, dried over magnesium sulfate, filtered and concentrate under reduced pressure. The solvent was removed under reduced pressure to afford the title compound. $^1$H NMR (300 MHz, CDCl$_3$) δ ppm 1.76 (m, 4H), 2.61 (t, J=5.43 Hz, 2H), 2.72 (t, J=5.43 Hz, 2H), 2.87 (t, J=6.27 Hz, 2H), 3.96 (s, 3H), 4.21 (t, J=6.10 Hz, 2H), 6.67 (d, J=8.13 Hz, 1H), 7.64 (d, J=8.13 Hz, 1H). MS (DCI) m/z 232.08 (M+H)$^+$.

Example 6E 3,4,7,8,9,10-Hexahydro-2H-benzo chromen-4-amine

Example 6D (2.0 g, 8.65 mmol), 10% palladium on carbon (0.2 g), and 20% ammonia in methanol (20 mL) were shaken under hydrogen (60 psi) for 2 hours at ambient temperature. The catalyst was removed by filtration and the solvent was evaporated under reduced pressure to afford the title compound. $^1$H NMR (300 MHz, CDCl$_3$) δ ppm 1.75 (m, 4H), 1.83 (m, 1H), 1.93 (br s, 2H), 2.13 (m, 1H), 2.59 (t, J=5.09 Hz, 2H), 2.71 (t, J=5.59 Hz, 2H), 4.03 (t, J=5.09 Hz, 1H), 4.26 (m, 2H), 6.66 (d, J=7.80 Hz, 1H), 7.06 (d, J=7.79 Hz, 1H). MS (DCI) m/z 203.0 (M+NH$_4$—H$_2$O)$^+$.

Example 6F

N-(3,4,7,8,9,10-Hexahydro-2H-benzo[h]chromen-4-yl)-N'-(7-hydroxy-5,6,7,8-tetrahydronaphthalen-1-yl)urea To a mixture of di(N-succinimidyl) carbonate (417 mg, 1.63 mmol) in acetonitrile (5 mL) was added Example 1G (430 mg, 1.55 mmol) dissolved in acetonitrile (5 mL) and pyridine (0.13 mL, 1.63 mmol). After stirring for 15 minutes at ambient temperature, Example 6E (315 mg, 1.55 mmol) in acetonitrile (5 mL), dimethylformamide (10 mL), and diisopropylethylamine (0.81 mL, 4.65 mmol) were added and the mixture stirred for 30 minutes. Ethyl acetate (200 mL) and water (200 mL) were added and the organic layer was washed with brine, dried over anhydrous sodium sulfate, filtered, and concentrate under reduced pressure. The residue was chromatographed on silica gel eluting with 0-to-30% ethyl acetate in hexane, and concentrated under reduced pressure to afford 1-(7-(tert-butyldimethylsilyloxy)-5,6,7,8-tetrahydronaphthalen-1-yl)-3-(3,4,7,8,9,10-hexahydro-2H-benzo[h]-chromen-4-yl)urea. The intermediate was dissolved in tetrahydrofuran (20 mL), tetrabutylammonium fluoride (1.0M in THF, 3.1 mL, 3.1 mmol) was added, and the mixture stirred overnight at ambient temperature. The mixture was concentrated under reduced pressure and chromatographed on silica gel eluting with 0-to-10% methanol in ethyl acetate. The residue was suspended in methanol (70 mL), sonicated, water (300 mL) was added, and the sonication was repeated. The solids were collected by filtration, rinsed with water, and freeze-dried to afford the title compound. $^1$H NMR (300 MHz, DMSO-d$_6$) δ ppm 1.58 (m, 1H), 1.67 (m, 4H), 1.88 (m, 2H), 2.04 (m, 1H), 2.28 (dd, 1H), 2.73 (m, 5H), 3.91 (m, 1H), 4.13 (td, 1H), 4.29 (dt, 1H), 4.76 (q, 1H), 4.84 (d, 1H), 6.61 (d, 1H), 6.69 (d, 1H), 6.99 (m, 3H), 7.43 (s, 1H), 7.72 (d, 1H). MS (ESI) m/z 393.21 (M+H)$^1$. Calcd for $C_{24}H_{28}N_2O_3 \cdot 0.20H_2O$: C, 72.78; H, 7.23; N, 7.07. Found: C, 72.79; H, 7.29; N, 7.01.

Example 7

N-(7-Hydroxy-5,6,7,8-tetrahydronaphthalen-1-yl)-N'-(6-methyl-3,4-dihydro-2H-chromen-4-yl)urea Example 7A 6-Methyl chroman-4-one O-methyl oxime 6-Methylchroman-4-one (Aldrich, 3.24 g, 20 mmol) was dissolved in pyridine (15 mL). Methoxyl amine hydrochloride (1.84 g, 22 mmol) was added and the mixture stirred for 16 hours at ambient temperature. The pyridine was removed under reduced pressure, and the residue was added to water and diethyl ether. The aqueous layer was extracted with diethyl ether, and the combined organic layers washed with 1N sodium hydroxide and 1N hydrochloric acid and then dried with magnesium sulfate and filtered. The solvent was removed under reduced pressure to afford the title compound. $^1$H NMR (300 MHz, CDCl$_3$) δ ppm 2.28 (s, 3H), 2.88 (t, J=6.27 Hz, 2H), 3.98 (s, 3H), 4.17 (t, J=6.27 Hz, 2H), 6.78 (d, J=8.48 Hz, 1H), 7.05 (dd, J=8.48, 2.03 Hz, 1H), 7.70 (d, J=2.03 Hz, 1H). MS (DCI) m/z 192.02 (M+H)$^+$.

Example 7B

6-Methyl-chroman-4-ylamine

A solution of Example 7A (4.24 g) in 20% ammonia in methanol (50 mL) was treated with Raney Nickel, 40 g, under hydrogen (60 psi) for 4 hours at ambient temperature. The mixture was filtered, and the solvent was evaporated under reduced pressure. The residue dissolved in diethyl ether which was washed sequentially with water and saturated aqueous sodium bicarbonate, dried with magnesium sulfate, filtered and concentrated under reduced pressure to afford the title compound. $^1$H NMR (300 MHz, CDCl$_3$) δ ppm 1.78-1.88 (m, 1H), 2.10-2.21 (m, 1H), 2.27 (s, 3H), 4.01 (m, 1H), 4.22 (m, 2H), 6.71 (d, J=8.5 Hz, 1H), 6.95 (d, J=8.5 Hz, 1H), 7.11 (s, 1H). MS (DCI) m/z 164 (M+H)$^+$.

Example 7C

N-(7-Hydroxy-5,6,7,8-tetrahydronaphthalen-1-yl)-N'-(6-methyl-3,4-dihydro-2H-chromen-4-yl)urea Di(N-succinimidyl) carbonate (542 mg, 2.12 mmol) was suspended in acetonitrile (5 mL), and Example 1G (559 mg, 2.02 mmol) dissolved in acetonitrile (5 mL) and pyridine (0.17 mL, 2.12 mmol) was added to the mixture. After stirring for 15 minutes at ambient temperature, Example 7B (329 mg, 2.02 mmol) dissolved in acetonitrile (5 mL), dimethylformamide (10 mL), and diisopropylethylamine (1.05 mL, 6.05 mmol) was added and the mixture stirred for 30 minutes. Ethyl acetate (200 mL) and water (200 mL) were added, and the organic layer was washed with brine and dried over anhydrous sodium sulfate, filtered, concentrate under reduced pressure. The residue was chromatographed on silica gel eluting with 0-to-30% ethyl acetate in hexane to afford 1-(7-(tert-butyldimethylsilyloxy)-5,6,7,8-tetrahydronaphthalen-1-yl)-3-(6-methylchroman-4-yl)urea. The intermediate was dissolved in tetrahydrofuran (20 mL), tetrabutylammonium fluoride (1.0M in THF, 4.0 mL, 4.0 mmol) was added, and the mixture stirred overnight at ambient temperature. The mixture was concentrated under reduced pressure and chromatographed on silica gel eluting with 0-to-10% methanol in ethyl acetate. The residue was suspended in methanol (25 mL), sonicated, water was added (250 mL), and the sonication was repeated. The solids were collected by filtration, rinsed with water, and freeze-dried to afford the title compound. $^1$H NMR (300 MHz, DMSO-d$_6$) δ ppm 1.59 (m, 1H), 1.89 (m, 2H), 2.06 (m, 1H), 2.22 (s, 3H), 2.29 (dd, 1H), 2.75 (m, 3H), 3.91 (m, 1H), 4.08 (td, 1H), 4.22 (dt, 1H), 4.78 (q, 1H), 4.84 (d, 1H), 6.70 (m, 2H), 7.00 (m, 2H), 7.06 (m, 2H), 7.46 (s, 1H), 7.74 (d, 1H). MS (ESI) m/z 353.12 (M+H)$^+$. Calcd for $C_{21}H_{24}N_2O_3 \cdot 0.05H_2O$: C, 71.39; H, 6.87; N, 7.93. Found: C, 71.39; H, 6.98; N, 7.90.

Example 8

N-[(4R)-3,4-Dihydro-2H-chromen-4-yl]-N'-(7-hydroxy-5,6,7,8-tetrahydronaphthalen-1-yl)urea Di(N-succinimidyl) carbonate (538 mg, 2.1 mmol) was suspended in acetonitrile (5 mL), Example 1G (555 mg, 2.0 mmol) dissolved in acetonitrile (10 mL) and pyridine (0.17 mL, 2.1 mmol) were added, and the mixture stirred for 15 minutes at ambient temperature. (R)-chroman-4-amine hydrochloride (J&W PharmLab, 371 mg, 2.0 mmol) and diisopropylethylamine (1.05 mL, 6.0 mmol) were added and the mixture stirred for 30 minutes. The mixture was filtered through a silica gel plug, rinsed with 1/1 ethyl acetate/hexane, and concentrated under reduced pressure to afford 1-(7-(tert-butyldimethylsilyloxy)-5,6,7,8-tetrahydronaphthalen-1-yl)-3-((R)-chroman-4-yl)urea. The intermediate was dissolved in tetrahydrofuran (30 mL), tetrabutylammonium fluoride (1.0M in THF, 4.0 mL, 4.0 mmol) was added, and the mixture stirred overnight at ambient temperature. The mixture was concentrated under reduced pressure and chromatographed on silica gel eluting with 0-to-10% methanol in ethyl acetate. The residue was suspended in methanol (20 mL), sonicated after which and water (200 mL)was added. Sonication was repeated and the solids were collected by filtration, rinsed with water, and freeze-dried to afford the title compound. [α]$_D$: +46.8° (c1.0, 1:1 DMSO:MeOH). $^1$H NMR (300 MHz, DMSO-d$_6$) δ ppm 1.58 (m, 1H), 1.86 (m, 1H), 1.97 (m, 1H), 2.09 (m, 1H), 2.29 (dd, 1H), 2.75 (m, 3H), 3.91 (m, 1H), 4.13 (td, 1H), 4.27 (m, 1H), 4.83 (d, 1H), 4.86 (q, 1H), 6.70 (d, 1H), 6.78 (dd, 1H), 6.90 (td, 1H), 7.00 (t, 1H), 7.09 (d, 1H), 7.17 (td, 1H), 7.26 (d, 1H), 7.46 (s, 1H), 7.73 (d, 1H). MS (ESI) m/z 339.11 (M+H)$^+$. Calcd for C$_{20}$H$_{22}$N$_2$O$_3$·0.26H$_2$O: C, 70.02; H, 6.62; N, 8.17. Found: C, 70.05; H, 6.78; N, 8.13.

Example 9

N-[(4S)-3,4-Dihydro-2H-chromen-4-yl]-N'-(7-hydroxy-5,6,7,8-tetrahydronaphthalen-1-yl)urea Di(N-succinimidyl) carbonate (538 mg, 2.1 mmol) was suspended in acetonitrile (5 mL), and Example 1G (555 mg, 2.0 mmol) dissolved in acetonitrile (10 mL) and pyridine (0.17 mL, 2.1 mmol) was added. After stirring for 15 minutes at ambient temperature, (S)-chroman-4-amine hydrochloride (J&W PharmLab, 371 mg, 2.0 mmol) and diisopropylethylamine (1.05 mL, 6.0 mmol) was added and the mixture stirred for 30 minutes. The mixture was filtered through a silica gel plug, rinsed with 1/1 ethyl acetate/hexane, and concentrated under reduced pressure to afford 1-(7-(tert-butyldimethylsilyloxy)-5,6,7,8-tetrahydronaphthalen-1-yl)-3-((S)-chroman-4-yl)urea. The intermediate was dissolved in tetrahydrofuran (30 mL), tetrabutylammonium fluoride (1.0M in THF, 4.0 mL, 4.0 mmol) was added, and the mixture stirred overnight at ambient temperature. The mixture was concentrated under reduced pressure and chromatographed on silica gel eluting with 0-to-10% methanol in ethyl acetate. The residue was suspended in methanol (20 mL), sonicated, and water (200 mL) was added. The sonication was repeated and the solids were collected by filtration, rinsed with water, and freeze-dried to afford the title compound. [α]$_D$: −45.0° (c:1.0, 1:1 DMSO:MeOH). $^1$H NMR (300 MHz, DMSO-d$_6$) δ ppm 1.58 (m, 1H), 1.86 (m, 1H), 1.97 (m, 1H), 2.09 (m, 1H), 2.29 (dd, 1H), 2.75 (m, 3H), 3.91 (m, 1H), 4.13 (td, 1H), 4.27 (m, 1H), 4.83 (d, 1H), 4.86 (q, 1H), 6.70 (d, 1H), 6.78 (dd, 1H), 6.90 (td, 1H), 7.00 (t, 1H), 7.09 (d, 1H), 7.17 (td, 1H), 7.26 (d, 1H), 7.46 (s, 1H), 7.73 (d, 1H). MS (ESI) m/z 339.06 (M+H)$^+$. Calcd for C$_{20}$H$_{22}$N$_2$O$_3$·0.31 H$_2$O: C, 69.83; H, 6.63; N, 8.14. Found: C, 69.82; H, 6.58; N, 8.13.

Example 10

N-(3,4-Dihydro-2H-chromen-2-ylmethyl)-N'-(7-hydroxy-5,6,7,8-tetrahydronaphthalen-1-yl)urea

Example 10A

Chroman-2-carboxylic acid

4-Oxo-4H-chromene-2-carboxylic acid (Aldrich, 3.0 g, 15.8 mmol) was added to a mixture of acetic acid (30 mL) and 10% palladium on carbon (0.3 g) in a Parr shaker. The glass reactor was sealed and flushed with nitrogen, and it was pressurized with hydrogen (60 psi). The mixture was shaken at 70° C. for 2.5 hours. The mixture was filtered and the solids were rinsed with methanol. The filtrate was concentrated under reduced pressure and chromatographed on silica gel eluting with 0-to-10% methanol in ethyl acetate to afford the title compound. $^1$H NMR (300 MHz, DMSO-d$_6$) δ ppm 2.04 (m, 1H), 2.14 (m, 1H), 2.63 (dt, 1H), 2.78 (dt, 1H), 4.76 (dd, 1H), 6.80 (m, 2H), 7.05 (m, 2H). MS (ESI) m/z 177.09 (M−H)$^-$.

Example 10B

Chroman-2-carboxamide

Example 10A (2.796 g, 15.7 mmol) was dissolved in dichloromethane (60 mL), and oxalyl chloride (4.1 mL, 47.1 mmol) was added with a few drops of dimethylformamide. The mixture stirred for one hour at ambient temperature and was concentrated under reduced pressure to an orange oil. The residue was dissolved in dichloromethane (20 mL), and added to 0.5M ammonia in dioxane (200 mL). After stirring overnight, and filtering off the salts, the filtrate was concentrated under reduced pressure and chromatographed on silica gel eluting with 50-to-100% ethyl acetate in hexane to afford the title compound. $^1$H NMR (300 MHz, DMSO-d$_6$) δ ppm 1.89 (m, 1H), 2.15 (m, 1H), 2.68 (dt, 1H), 2.80 (ddd, 1H), 4.45 (dd, 1H), 6.83 (m, 2H), 7.07 (m, 2H), 7.35 (d, 2H). MS (DCI) m/z 195.08 (M+NH$_4$)$^1$.

Example 10C

Chroman-2-ylmethanamine

Lithium aluminum hydride (1.0M in THF, 42.5 mL, 42.5 mmol) was added to Example 10B (2.510 g, 14.2 mmol) dissolved in tetrahydrofuran (40 mL). The mixture was stirred for 1.5 hours at ambient temperature then refluxed for two hours. The mixture was chilled to 0° C. followed by the sequential additions of water (3.5 mL), tetrahydrofuran (100 mL), 15% sodium hydroxide (3.5 mL), and water (7.0 mL). The slurry was filtered, the solids were rinsed with ethyl acetate (200 mL), and the filtrate was concentrated under reduced pressure to afford the title compound. Obtained 2.329 g of Example 10C. $^1$H NMR (300 MHz, DMSO-d$_6$) δ ppm 1.55 (m, 3H), 2.00 (m, 1H), 2.74 (qd, 4H), 3.87 (dtd, 1H), 6.71 (dd, 1H), 6.78 (td, 1H), 7.03 (m, 2H). MS (DCI) m/z 164.07 (M+H)$^+$.

Example 10D

N-(3,4-Dihydro-2H-chromen-2-ylmethyl)-N'-(7-hydroxy-5,6,7,8-tetrahydronaphthalen-1-yl)urea Di(N-succinimidyl) carbonate (538 mg, 2.1 mmol) was suspended in acetonitrile (5 mL), and Example 1G (555 mg, 2.0 mmol) dissolved in acetonitrile (5 mL) and pyridine (0.17 mL, 2.1 mmol) was added and the mixture stirred for 15 minutes at ambient temperature. Example 10C (326 mg, 2.0 mmol) dissolved in acetonitrile (10 mL) and diisopropylethylamine (1.05 mL, 6.0 mmol) was added and the mixture stirred for 30 minutes. The mixture was concentrated under reduced pressure and the residue was chromatographed on silica gel eluting with 0-to-40% ethyl acetate in hexane to afford 1-(7-(tert-butyldimethylsilyloxy)-5,6,7,8-tetrahydronaphthalen-1-yl)-3-(chroman-2-ylmethyl)urea. The intermediate was dissolved in tetrahydrofuran (20 mL), tetrabutylammonium fluoride (1.0M in THF, 4.0 mL, 4.0 mmol) was added and the mixture stirred overnight at ambient temperature. The mixture was concentrated under reduced pressure and the residue was chromatographed on silica gel eluting with 0-to-10% methanol in ethyl acetate. The residue was suspended in methanol (20 mL), sonicated, water (200 mL) was added, and the sonication was repeated. The solids were collected by filtration, rinsed with water, and freeze-dried to afford the title compound. $^1$H NMR (300 MHz, DMSO-d$_6$) δ ppm 1.57 (m, 1H), 1.70 (m, 1H), 1.86 (m, 1H), 1.98 (m, 1H), 2.32 (dd, 1H), 2.78 (m, 5H), 3.38 (q, 2H), 3.92 (m, 1H), 4.06

(m, 1H), 4.83 (d, 1H), 6.69 (d, 1H), 6.81 (m, 3H), 6.98 (t, 1H), 7.07 (m, 2H), 7.65 (t, 2H). MS (ESI) m/z 353.09 (M+H)$^+$. Calcd for $C_{21}H_{24}N_2O_3 \cdot 0.12H_2O$: C, 71.13; H, 6.89; N, 7.90. Found: C, 71.13; H, 6.63; N, 7.78.

Example 11

N-[(7-Ethoxy-3,4-dihydro-2H-chromen-2-yl)methyl]-N'-(7-hydroxy-5,6,7,8-tetrahydronaphthalen-1-yl)urea

Example 11A

7-Ethoxy-4-oxo-4H-chromene-2-carboxylic acid

To a solution of 1-(4-ethoxy-2-hydroxyphenyl)ethanone (Aldrich, 5.0 g, 27.7 mmol) and diethyl oxalate (8.3 mL, 61 mmol) in ethanol (50 mL) was added sodium ethoxide (21% in EtOH, 31 mL, 83 mmol) and the mixture was refluxed for 1.5 hours. The mixture was cooled to ambient temperature, diethyl ether (150 mL), water (150 mL) and 12N hydrochloric acid (7 mL) were added. The separated organic layer was washed with brine, dried over anhydrous sodium sulfate, filtered and was concentrated under reduced pressure to afford ethyl 7-ethoxy-4-oxo-4H-chromene-2-carboxylate. The intermediate was dissolved in acetic acid (70 mL) and 12N hydrochloric acid (8.5 mL), heated to reflux for 2 hours, and cooled to ambient temperature. Water (300 mL) was added and the solids were collected by filtration, rinsed with water, and freeze-dried to afford the title compound. $^1$H NMR (300 MHz, DMSO-$d_6$) δ ppm 1.38 (t, 3H), 4.20 (q, 2H), 6.84 (s, 1H), 7.08 (dd, 1H), 7.19 (d, 1H), 7.92 (d, 1H). MS (APCI) m/z 235.04 (M+H)$^1$.

Example 11B

7-Ethoxychroman-2-carboxylic acid

Example 11A (3.0 g, 12.8 mmol) was added to a mixture of acetic acid (30 mL) and 10% palladium on carbon (0.3 g) in a Parr shaker. The glass reactor was sealed and flushed with nitrogen, and pressurized with hydrogen (60 psi). The mixture was shaken at 70° C. for 3 hours. The mixture was filtered and the solids were rinsed with methanol. The filtrate was concentrated under reduced pressure and chromatographed on silica gel eluting with 0-to-10% methanol in ethyl acetate to afford the title compound. $^1$H NMR (300 MHz, DMSO-$d_6$) δ ppm 1.29 (t, 3H), 2.01 (m, 1H), 2.10 (m, 1H), 2.57 (m, 1H), 2.69 (dt, 1H), 3.94 (q, 2H), 4.73 (dd, 1H), 6.34 (d, 1H), 6.40 (dd, 1H), 6.90 (d, 1H), 12.94 (br s, 1H). MS (ESI) m/z 221.12 (M−H)$^−$.

Example 11C

7-Ethoxychroman-2-carboxamide

Example 11B (2.462 g, 11.1 mmol) was dissolved in dichloromethane (40 mL) followed by the addition of oxalyl chloride (2.9 mL, 33.2 mmol) and a few drops of dimethylformamide. The mixture stirred for one hour at ambient temperature, was concentrate under reduced pressure, and dissolved in dichloromethane (20 mL), and added to 0.5M ammonia in dioxane (200 mL). The mixture stirred overnight and was filtered. The filtrate was concentrate under reduced pressure, and the residue was chromatographed on silica gel eluting with 50-to-100% ethyl acetate in hexane to afford the title compound. $^1$H NMR (300 MHz, DMSO-$d_6$) δ ppm 1.29 (t, 3H), 1.86 (m, 1H), 2.12 (m, 1H), 2.59 (dt, 1H), 2.70 (ddd, 1H), 3.94 (q, 2H), 4.42 (dd, 1H), 6.41 (m, 2H), 6.92 (d, 1H), 7.33 (d, 2H). MS (DCI) m/z 239.13 (M+NH$_4$)$^1$.

Example 11D (7-Ethoxychroman-2-yl)methanamine

Lithium aluminum hydride (1.0M in THF, 24.3 mL, 24.3 mmol) was added to Example 11C (1.79 g, 8.09 mmol) suspended in tetrahydrofuran (60 mL). The mixture stirred for 1.5 hours at ambient temperature and was refluxed for two hours. The mixture was chilled to 0° C., and was sequentially added water (2.0 mL), tetrahydrofuran (60 mL), 15% sodium hydroxide (2.0 mL), and water (4.0 mL). The mixture was filtered, the solids were rinsed with ethyl acetate (200 mL), and the filtrate was concentrated under reduced pressure to afford the title compound. $^1$H NMR (300 MHz, DMSO-$d_6$) δ ppm 1.28 (t, 3H), 1.56 (m, 3H), 1.98 (m, 1H), 2.70 (m, 4H), 3.84 (m, 1H), 3.92 (q, 2H), 6.28 (d, 1H), 6.36 (dd, 1H), 6.90 (d, 1H). MS (DCI) m/z 208.10 (M+H)$^+$.

Example 11E

N-[(7-Ethoxy-3,4-dihydro-2H-chromen-2-yl)methyl]-N'-(7-hydroxy-5,6,7,8-tetrahydronaphthalen-1-yl)urea Di(N-succinimidyl) carbonate (538 mg, 2.1 mmol) was suspended in acetonitrile (5 mL) followed by the addition of Example 1G (555 mg, 2.0 mmol) dissolved in acetonitrile (5 mL) and pyridine (0.17 mL, 2.1 mmol) and the mixture stirred for 15 minutes at ambient temperature. Example 11D (415 mg, 2.0 mmol) dissolved in acetonitrile (10 mL) and diisopropylethylamine (1.05 mL, 6.0 mmol) was added and the mixture stirred for 30 minutes. The mixture was concentrated under reduced pressure and the residue was chromatographed on silica gel eluting with 0-to-40% ethyl acetate in hexane to afford 1-(7-(tert-butyl dimethylsilyloxy)-5,6,7,8-tetrahydronaphthalen-1-yl)-3-(7-ethoxychroman-2-yl)methyl)urea. The intermediate was dissolved in tetrahydrofuran (20 mL), and tetrabutylammonium fluoride (1.0M in THF, 4.0 mL, 4.0 mmol) was added and the mixture stirred overnight at ambient temperature. The mixture was concentrated under reduced pressure and the residue was chromatographed on silica gel eluting with 0-to-10% methanol in ethyl acetate. The solid was suspended in methanol (20 mL), sonicated, and water (200 mL) was added. The sonication was repeated and the solids were collected by filtration, rinsed with water, and freeze-dried to afford the title compound. $^1$H NMR (300 MHz, DMSO-$d_6$) δ ppm 1.29 (t, 3H), 1.61 (m, 2H), 1.86 (m, 1H), 1.95 (m, 1H), 2.32 (dd, 1H), 2.74 (m, 5H), 3.37 (q, 2H), 3.92 (m, 1H), 3.93 (q, 2H), 4.04 (m, 1H), 4.84 (d, 1H), 6.32 (d, 1H), 6.39 (dd, 1H), 6.69 (d, 1H), 6.84 (t, 1H), 6.93 (d, 1H), 6.98 (t, 1H), 7.65 (m, 2H). MS (ESI) m/z 397.19 (M+H)$^+$. Calcd for $C_{23}H_{28}N_2O_4 \cdot 0.15H_2O$: C, 69.20; H, 7.15; N, 7.02. Found: C, 69.26; H, 7.00; N, 6.43.

Example 12

N-(7-Hydroxy-5,6,7,8-tetrahydronaphthalen-1-yl)-N-[(6-methyl-3,4-dihydro-2H-chromen-2-yl)methyl]urea

Example 12A

6-Methylchroman-2-carboxylic acid

6-Methyl-4-oxo-4H-chromene-2-carboxylic acid (Aldrich, 3.5 g, 17.1 mmol) was added to a mixture of acetic acid (50 mL) and 10% palladium on carbon (0.35 g) in a Parr shaker. The glass reactor was sealed and flushed with nitrogen, and pressurized with hydrogen (60 psi). The mixture was shaken at 70° C. for 2.5 hours, and filtered and solids were rinsed with methanol. The filtrate was concentrated under reduced pressure to afford the title compound. $^1$H NMR (300 MHz, CDCl$_3$) δ ppm 2.09-2.23 (m, 1H), 2.25 (s, 3H), 2.28-2.40 (m, 1H), 2.72-2.86 (m, 2H), 4.71 (dd, J=8.48, 3.39 Hz, 1H), 6.83 (t, J=8.65 Hz, 2H), 6.90-6.96 (m, 1H). MS (ESI) m/z 210.1 (M+NH$_4$)$^+$.

Example 12B

6-Methylchroman-2-carboxamide

To a solution of Example 12A (3.3 g, 17.1 mmol) dissolved in dichloromethane (60 mL) was added oxalyl chloride (4.5 mL, 51.6 mmol) and a few drops of dimethylformamide. After stirring for 30 minutes at ambient temperature, the solvent was evaporated and the residue was dissolved in dichloromethane (30 mL) and added to 0.5M ammonia in dioxane (100 mL). The mixture stirred overnight, was filtered, and the filtrate was concentrate under reduced pressure. The residue was dissolved in ethyl acetate, and filtered through a silica gel plug and the filtrate was concentrated under reduced pressure to afford the title compound. $^1$H NMR (300 MHz, DMSO-d$_6$) δ ppm 1.79-1.94 (m, 1H), 2.07-2.17 (m, 1H), 2.19 (s, 3H), 2.62 (dt, J=16.53, 5.30 Hz, 1H), 2.70-2.82 (m, 1H), 4.41 (dd, J=8.99, 3.22 Hz, 1H), 6.73 (d, J=8.14 Hz, 1H), 6.84-6.91 (m, 2H), 7.35 (d, J=6.10 Hz, 2H). MS (ESI) m/z 192.13 (M+H)$^+$.

Example 12C (6-Methylchroman-2-yl)methanamine

Lithium aluminum hydride (1.0M in THF, 31.5 mL, 31.5 mmol) was added to Example 12B (2.009 g, 10.5 mmol) dissolved in tetrahydrofuran (40 mL). The mixture stirred for 1.5 hours at ambient temperature, and then refluxed for 2.5 hours. After cooling to 0° C., the following was added sequentially: water (2.6 mL), tetrahydrofuran (75 mL), 15% sodium hydroxide (2.6 mL), and water (5.2 mL). The slurry was filtered, the solids were rinsed with ethyl acetate (200 mL), and the filtrate was concentrated under reduced pressure to afford the title compound. $^1$H NMR (300 MHz, DMSO-d$_6$) δ ppm 1.55 (m, 3H), 1.98 (m, 1H), 2.17 (s, 3H), 2.71 (qd, 4H), 3.81 (dtd, 1H), 6.59 (d, 1H), 6.84 (m, 2H). MS (DCI) m/z 178.10 (M+H)$^+$.

Example 12D

N-(7-Hydroxy-5,6,7,8-tetrahydronaphthalen-1-yl)-N'-[(6-methyl-3,4-dihydro-2H-chromen-2-yl)methyl]urea Di-(N-succinimidyl) carbonate (538 mg, 2.1 mmol) was suspended in acetonitrile (5 mL) after which Example 1G (555 mg, 2.0 mmol) dissolved in acetonitrile (5 mL) and pyridine (0.17 mL, 2.1 mmol) were added. After stirring for 15 minutes at ambient temperature, Example 12C (354 mg, 2.0 mmol) dissolved in acetonitrile (10 mL) and diisopropylethylamine (1.05 mL, 6.0 mmol) were added and the mixture stirred for 30 minutes. The mixture was concentrated under reduced pressure and chromatographed on silica gel eluting with 0-to-40% ethyl acetate in hexane, to afford 1-(7-(tert-butyldimethylsilyloxy)-5,6,7,8-tetrahydronaphthalen-1-yl)-3-((6-methylchroman-2-yl)methyl)urea. The intermediate was dissolved in tetrahydrofuran (20 mL), and tetrabutylammonium fluoride (1.0M in THF, 4.0 mL, 4.0 mmol) was added and the mixture stirred overnight at ambient temperature. The mixture was concentrated under reduced pressure and chromatographed on silica gel eluting with 0-to-10% methanol in ethyl acetate. The residue was suspended in methanol (20 mL), sonicated, and water (200 mL) was added. The sonication was repeated and the solids were collected by filtration, rinsed with water, and freeze-dried to afford the title compound. $^1$H NMR (300 MHz, DMSO-d$_6$) δ ppm 1.62 (m, 2H), 1.86 (m, 1H), 1.96 (m, 1H), 2.19 (s, 3H), 2.32 (dd, 1H), 2.76 (m, 5H), 3.36 (q, 2H), 3.92 (m, 1H), 4.02 (m, 1H), 4.83 (d, 1H), 6.68 (m, 2H), 6.86 (m, 3H), 6.98 (t, 1H), 7.64 (t, 2H). MS (ESI) m/z 367.17 (M+H)$^1$. Calcd for C$_{22}$H$_{26}$N$_2$O$_3$.0.11H$_2$O: C, 71.72; H, 7.17; N, 7.60. Found: C, 71.71; H, 7.02; N, 7.50.

Example 13

N-(7-Hydroxy-5,6,7,8-tetrahydronaphthalen-1-yl)-N'-[(8-isopropyl-3,4-dihydro-2H-chromen-2-yl)methyl]urea Example 13A 1-(2-Hydroxy-3-isopropylphenyl)ethanone 2-Hydroxy-3-isopropylbenzoic acid (Aldrich, 4.0 g, 22.2 mmol) was dissolved in tetrahydrofuran (20 mL), chilled to −75° C., and methyllithium (1.6M in diethyl ether, 42 mL, 66.6 mmol) was added. The mixture stirred overnight at ambient temperature. The mixture was quenched with methanol (50 mL), concentrate under reduced pressure, and ethyl acetate (200 mL) was added. The mixture was washed with 1N hydrochloric acid (200 mL), water (200 mL), and brine and the organic layer was dried over anhydrous sodium sulfate, filtered and concentrate under reduced pressure. The residue was chromatographed on silica gel eluting with 0-to-30% ethyl acetate in hexane to afford the title compound. $^1$H NMR (300 MHz, CDCl$_3$) δ ppm 1.23 (d, 6H), 2.64 (s, 3H), 3.39 (m, 1H), 6.87 (t, 1H), 7.41 (dd, 1H), 7.59 (dd, 1H), 12.69 (s, 1H). MS (DCI) m/z 179.07 (M+H)$^+$.

Example 13B

8-Isopropyl-4-oxo-4H-chromene-2-carboxylic acid

To a solution of Example 13A (2.048 g, 11.5 mmol) in ethanol (60 mL) was added diethyl oxalate (3.43 mL, 25.3 mmol) and sodium ethoxide (21% in EtOH, 12.9 mL, 34.5 mmol) and the mixture was refluxed for 30 minutes. The mixture was cooled to ambient temperature, partitioned between diethyl ether (150 mL) and water (150 mL). Hydrochloric acid (12N, 3 mL) was added and the separated organic layer was washed with brine, dried over anhydrous sodium sulfate, filtered and concentrated under reduced pressure to afford ethyl 8-isopropyl-4-oxo-4H-chromene-2-carboxylate. After dissolving the intermediate in acetic acid (45 mL) and 12N hydrochloric acid (7.5 mL), the mixture was heated to reflux for 5.5 hours then cooled to ambient temperature. Water (400 mL) was added and the mixture was extracted with ethyl acetate (400 mL). The combined organic layers were washed with water (400 mL) and brine, dried over anhydrous sodium sulfate and filtered. The solution was concentrated under reduced pressure and vacuum dried overnight to afford the title compound. $^1$H NMR (300 MHz, DMSO-d$_6$)

δ ppm 1.32 (d, 6H), 3.56 (m, 1H), 6.91 (s, 1H), 7.48 (t, 1H), 7.78 (dd, 1H), 7.89 (dd, 1H). MS (ESI) m/z 232.94 (M+H)+.

Example 13C

8-Isopropylchroman-2-carboxylic acid

Example 13B (2.421 g, 10.4 mmol) was added to a mixture of acetic acid (30 mL) and 10% palladium on carbon (0.25 g) in a Parr shaker. The glass reactor was sealed and flushed with nitrogen, and pressurized with hydrogen (60 psi). The mixture was shaken at 70° C. for 3 hours. The mixture was filtered, the solids were rinsed with methanol and the filtrate was concentrated under reduced pressure and chromatographed on silica gel eluting with 0-to-50% ethyl acetate in hexane to afford the title compound. $^1$H NMR (300 MHz, DMSO-$d_6$) δ ppm 1.16 (dd, 6H), 2.09 (m, 2H), 2.63 (m, 1H), 2.76 (dt, 1H), 3.22 (m, 1H), 4.81 (dd, 1H), 6.77 (t, 1H), 6.85 (dd, 1H), 6.99 (dd, 1H), 12.90 (br s, 1H). MS (ESI) m/z 219.15 (M−H)−.

Example 13D

8-Isopropylchroman-2-carboxamide

To a solution of Example 13C (2.157 g, 9.79 mmol) in dichloromethane (40 mL) was added oxalyl chloride (2.56 mL, 29.4 mmol) and a few drops of dimethylformamide. After stirring for one hour at ambient temperature, the mixture was concentrate under reduced pressure, dissolved in dichloromethane (20 mL), and added to 0.5M ammonia in dioxane (200 mL). After stirring overnight, the mixture was filtered, the filtrate was concentrate under reduced pressure, and the residue was chromatographed on silica gel eluting with 0-to-50% ethyl acetate in hexane to afford the title compound. $^1$H NMR (300 MHz, CDCl$_3$) δ ppm 1.24 (dd, 6H), 2.06 (m, 1H), 2.43 (m, 1H), 2.87 (m, 2H), 3.28 (m, 1H), 4.54 (dd, 1H), 5.53 (s, 1H), 6.55 (s, 1H), 6.91 (m, 2H), 7.07 (dd, 1H). MS (DCI) m/z 237.11 (M+NH$_4$)+.

Example 13E (8-Isopropylchroman-2-yl)methanamine

Lithium aluminum hydride (1.0M in THF, 19.6 mL, 19.6 mmol) was added to Example 13D (1.435 g, 6.54 mmol) dissolved in tetrahydrofuran (30 mL). The mixture stirred for 1.5 hours at ambient temperature, and refluxed for 2 hours. After cooling to 0° C., the following was added sequentially: water (1.6 mL), tetrahydrofuran (50 mL), 15% sodium hydroxide (1.6 mL) and additional water (3.2 mL). The mixture was filtered, and the solids were rinsed with ethyl acetate (200 mL). The combined filtrates were concentrated under reduced pressure to afford the title compound. $^1$H NMR (300 MHz, CDCl$_3$) δ ppm 1.21 (dd, 6H), 1.64 (br s, 2H), 1.76 (m, 1H), 1.94 (m, 1H), 2.78 (ddd, 1H), 2.88 (m, 1H), 2.95 (d, 2H), 3.28 (m, 1H), 3.97 (m, 1H), 6.81 (t, 1H), 6.89 (d, 1H), 7.02 (dd, 1H). MS (DCI) m/z 206.11 (M+H)+.

Example 13F

N-(7-Hydroxy-5,6,7,8-tetrahydronaphthalen-1-yl)-N'-[(8-isopropyl-3,4-dihydro-2H-chromen-2-yl)methyl]urea Di(N-succinimidyl) carbonate (538 mg, 2.1 mmol) was suspended in acetonitrile (5 mL) followed by the addition of Example 1G (555 mg, 2.0 mmol) dissolved in acetonitrile (5 mL) and pyridine (0.17 mL, 2.1 mmol). The mixture was stirred for 15 minutes at ambient temperature after which Example 13E (411 mg, 2.0 mmol) dissolved in acetonitrile (10 mL) and diisopropylethylamine (1.05 mL, 6.0 mmol) were added and the mixture stirred for 30 minutes. The mixture was concentrated under reduced pressure and chromatographed on silica gel eluting with 0-to-40% ethyl acetate in hexane to afford 1-(7-(tert-butyldimethylsilyloxy)-5,6,7,8-tetrahydronaphthalen-1-yl)-3-((8-isopropylchroman-2-yl)methyl)urea. The intermediate was dissolved in tetrahydrofuran (20 mL), tetrabutylammonium fluoride (1.0M in THF, 4.0 mL, 4.0 mmol) was added and the mixture stirred overnight at ambient temperature. The mixture was concentrated under reduced pressure and chromatographed on silica gel eluting with 0-to-10% methanol in ethyl acetate. The residue was dissolved in ethyl acetate (200 mL), washed with 1N sodium hydroxide (200 mL), water (200 mL), and brine and the combined organic layers were dried over anhydrous sodium sulfate, filtered, and concentrated under reduced pressure to afford the title compound. $^1$H NMR (300 MHz, DMSO-$d_6$) δ ppm 1.14 (d, 6H), 1.62 (m, 2H), 1.86 (m, 1H), 1.97 (m, 1H), 2.32 (dd, 1H), 2.78 (m, 5H), 3.25 (m, 1H), 3.41 (t, 2H), 3.92 (m, 1H), 4.06 (m, 1H), 4.85 (d, 1H), 6.76 (m, 3H), 6.87 (dd, 1H), 6.98 (m, 2H), 7.61 (d, 1H), 7.66 (s, 1H). MS (ESI) m/z 395.24 (M+H)+. Calcd for C$_{24}$H$_{10}$N$_2$O$_3$.0.27 EtOAc: C, 72.01; H, 7.75; N, 6.70. Found: C, 71.96; H, 7.85; N, 6.81.

Example 14

N-(8-tert-Butyl-1-methyl-1,2,3,4-tetrahydroquinolin-4-yl)-N'-(7-hydroxy-5,6,7,8-tetrahydronaphthalen-1-yl)urea

Example 14A

3-Bromo-N-(2-tert-butylphenyl)propanamide 2-tert-butylaniline (Aldrich, 24.7 g, 166 mmol) was dissolved in dichloromethane (100 mL) and potassium carbonate (47.0 g, 340 mmol) was added. 3-Bromopropionyl chloride (29.1 g, 170 mmol) in dichloromethane (50 mL) was added dropwise and the mixture stirred for 3 hours at ambient temperature. Water was added slowly to quench the mixture, and the organic layer was separated and washed twice with water, dried with magnesium sulfate, filtered, and concentrated under reduced pressure to afford the title compound. $^1$H NMR (300 MHz, DMSO-$d_6$) δ ppm 1.32 (s, 9H), 2.97 (t, J=6.44 Hz, 2H), 3.74 (t, J=6.27 Hz, 2H), 7.00-7.06 (m, 1H), 7.16-7.25 (m, 2H), 7.36-7.42 (m, 1H), 9.35 (s, 1H). MS (DCI) m/z 284.0 (M+H)+.

Example 14B 1-(2-tert-Butylphenyl)azetidin-2-one

Sodium tert-butoxide (2.5 g, 26 mmol) was dissolved in dimethylformamide (100 mL) followed by the addition of Example 14A (7.1 g, 25 mmol) dissolved in dimethylformamide (10 mL) and the mixture stirred for 2 hours at ambient temperature. Ethyl acetate (200 mL) was added and the organic layer was washed three times with water, dried with magnesium sulfate, filtered, and concentrated under reduced pressure to afford the title compound. $^1$H NMR (300 MHz, CDCl$_3$) δ ppm 1.41 (s, 9H), 3.10 (t, J=4.41 Hz, 2H), 3.64 (t, J=4.41 Hz, 2H), 7.13 (dd, J=7.46, 2.03 Hz, 1H), 7.19-7.31 (m, 2H), 7.46 (dd, J=7.80, 1.70 Hz, 1H). MS (DCI) m/z 204.0 (M+H)+.

Example 14C 8-tert-Butyl-2,3-dihydroquinolin-4(1H)-one

Example 14B (4.7 g, 23 mmol) was dissolved in dichloroethane (500 mL) followed by the addition of trifluoromethanesulfonic acid (10 g, 66.6 mmol) and the mixture stirred for 18 hours at ambient temperature. The mixture was quenched with potassium carbonate (20 g) and water (1 mL), stirred for 2 hours, and filtered through a plug of magnesium sulfate and concentrated under reduced pressure to afford the title compound. $^1$H NMR (300 MHz, CDCl$_3$) δ ppm 1.43 (s, 9H), 2.64-2.74 (m, 2H), 3.56-3.66 (m, 2H), 6.70 (t, J=7.80 Hz, 1H), 7.37 (dd, J=7.46, 1.70 Hz, 1H), 7.83 (dd, J=7.97, 1.53 Hz, 1H). MS (DCI) m/z 204.0 (M+H)+.

Example 14D 8-tert-Butyl-1-methyl-2,3-dihydroquinolin-4(1H)-one

Paraformaldehyde (5.0 g, 167 mmol) and 3 drops of glacial acetic acid were added to Example 14C (4.7 g, 23 mmol) in dichloroethane (50 mL) and the mixture was stirred for 30 minutes. Sodium triacetoxyborohydride (24 g, 113 mmol) was added and the mixture was heated to 60° C. for 4 hours. After cooling, ethyl acetate (300 mL) was added, and the organic layer was washed with 10% sodium bicarbonate, 5% citric acid, brine. The solution was dried over magnesium sulfate, filtered and concentrated under reduced pressure to afford the title compound. $^1$H NMR (300 MHz, CDCl$_3$) δ ppm 1.48 (s, 9H), 2.72 (s, 3H), 2.83 (t, J=6.27 Hz, 2H), 3.47 (t, J=6.44 Hz, 2H), 7.17 (t, J=7.80 Hz, 1H), 7.59 (dd, J=7.97, 1.53 Hz, 1H), 7.86 (dd, J=7.46, 1.70 Hz, 1H). MS (DCI) m/z 218.1 (M+H)+.

Example 14E 8-tert-Butyl-1-methyl-2,3-dihydroquinolin-4(1H)-one O-methyl oxime

Methoxylamine hydrochloride (0.86 g, 10.3 mmol) was added to a solution of Example 14D (2.04 g, 9.39 mmol) in pyridine (20 mL) and the mixture stirred overnight at ambient temperature. The mixture was concentrated under reduced pressure and ethyl acetate (200 mL) was added. The solution was washed twice with water (200 mL), once with brine, dried over anhydrous sodium sulfate, filtered, and concentrate under reduced pressure. The residue was chromatographed on silica gel eluting with 0-to-25% ethyl acetate in hexane to afford the title compound. $^1$H NMR (300 MHz, DMSO-d$_6$) δ ppm 1.41 (s, 9H), 2.46 (s, 3H), 2.80 (m, 2H), 3.07 (m, 2H), 3.93 (s, 3H), 7.11 (t, J=7.80 Hz, 1H), 7.35 (dd, J=7.97, 1.53 Hz, 1H), 7.62 (dd, J=7.63, 1.53 Hz, 1H). MS (DCI) m/z 247.14 (M+H)+.

Example 14F 8-tert-Butyl-1-methyl-1,2,3,4-tetrahydroquinolin-4-amine

Example 14E (1.227 g, 4.98 mmol) and Raney nickel (11.9 g) were added to a mixture of 20% ammonia in methanol (22 mL) in a Parr shaker. The glass reactor was sealed and flushed with nitrogen and pressurized with hydrogen (60 psi). The mixture was shaken at ambient temperature for one hour. The solids were filtered off and washed with methanol and the filtrate was concentrated under reduced pressure to afford the title compound. $^1$H NMR (300 MHz, DMSO-d$_6$) δ ppm 1.39 (s, 9H), 1.83 (m, 1H), 2.30 (m, 1H), 2.57 (s, 3H), 2.98 (t, J=6.61 Hz, 2H), 3.95 (t, J=7.29 Hz, 1H), 6.99 (t, J=7.63 Hz, 1H), 7.18 (d, J=8.14 Hz, 1H), 7.33 (d, J=7.46 Hz, 1H). MS (DCI) m/z 219.1 (M+H)+.

Example 14G

N-(8-tert-Butyl-1-methyl-1,2,3,4-tetrahydroquinolin-4-yl)-N'-(7-hydroxy-5,6,7,8-tetrahydronaphthalen-1-yl)urea To a mixture of di(N-succinimidyl) carbonate (538 mg, 2.1 mmol) suspended in acetonitrile (5 mL) was added Example 1G (555 mg, 2.0 mmol) dissolved in acetonitrile (5 mL) and pyridine (0.17 mL, 2.1 mmol). The mixture stirred for 15 minutes at ambient temperature and Example 14F (437 mg, 2.0 mmol), dissolved in acetonitrile (10 mL) and diisopropylethylamine (1.05 mL, 6.0 mmol), was added and the mixture stirred for 30 minutes at ambient temperature. The mixture was concentrated under reduced pressure and chromatographed on silica gel eluting with 0-to-30% ethyl acetate in hexane, to afford 1-(8-tert-butyl-1-methyl-1,2,3,4-tetrahydroquinolin-4-yl)-3-(7-(tert-butyldimethylsilyloxy)-5,6,7,8-tetrahydronaphthalen-1-yl)urea. The intermediate was dissolved in tetrahydrofuran (25 mL), and tetrabutylammonium fluoride (1.0M in THF, 4.0 mL, 4.0 mmol) was added, and the mixture stirred overnight at ambient temperature. The mixture was concentrated under reduced pressure and chromatographed on silica gel eluting with 0-to-10% methanol in ethyl acetate. The residue was dissolved in ethyl acetate (250 mL), washed with 1.0N sodium hydroxide (250 mL), water (250 mL), and brine, and dried over anhydrous sodium sulfate, filtered, concentrate under reduced pressure, and vacuum dried overnight to afford the title compound. $^1$H NMR (300 MHz, DMSO-d$_6$) δ ppm 1.42 (s, 9H), 1.59 (m, 1H), 1.70 (m, 1H), 1.87 (m, 1H), 2.37 (m, 2H), 2.62 (s, 3H), 2.77 (m, 3H), 3.04 (m, 2H), 3.91 (m, 1H), 4.84 (d, J=4.41 Hz, 1H), 4.95 (q, J=7.46 Hz, 1H), 6.70 (d, J=7.46 Hz, 1H), 7.01 (m, 3H), 7.14 (d, J=7.46 Hz, 1H), 7.26 (dd, J=7.97, 1.53 Hz, 1H), 7.51 (s, 1H), 7.74 (d, J=8.14 Hz, 1H). MS (ESI) m/z 408.27 (M+H)+. Calcd for C$_{25}$H$_{33}$N$_3$O$_2$.0.29 EtOAc: C, 72.55; H, 8.22; N, 9.70. Found: C, 72.54; H, 8.53; N, 9.73.

Example 15

N-(1-Benzyl-1,2,3,4-tetrahydroquinolin-4-yl)-N'-(7-hydroxy-5,6,7,8-tetrahydronaphthalen-1-yl)urea Example 15A 3-(Phenylamino)propanoic acid Aniline (9.11 mL, 100 mmol) was dissolved in acetonitrile (100 mL) and heated to reflux while β-propiolactone (Sigma, 6.29 mL, 100 mmol) in acetonitrile (20 mL) was added dropwise for 30 minutes. The mixture was refluxed for 3 hours and then stirred overnight at ambient temperature. The mixture was concentrate under reduced pressure, and chromatographed on silica gel eluting with 40-to-100% ethyl acetate in hexane to afford the title compound. $^1$H NMR (300 MHz, CDCl$_3$) δ ppm 2.69 (t, J=6.27 Hz, 2H), 3.48 (t, J=6.44

Hz, 2H), 6.66 (dd, J=8.81, 1.02 Hz, 2H), 6.75 (t, J=7.46 Hz, 1H), 7.20 (dd, J=8.65, 7.29 Hz, 2H). MS (DCI) m/z 166.05 (M+H)$^+$.

Example 15B 2,3-Dihydroquinolin-4(1H)-one

Example 15A (10.34 g, 62.6 mmol) and Eaton's reagent (Aldrich, 185 mL, 7.7% $P_2O_5$ in $CH_3SO_3H$) were heated at 95° C. for 17 hours, and then stirred overnight at ambient temperature. The mixture was added to ice (1 L) with stirring, and 200 mL, 1N sodium hydroxide in 25 mL portions was added to adjust the pH to 10. The mixture was extracted twice with ethyl acetate (1 L). The combined organic solution was washed with brine, dried over sodium sulfate, filtered, and concentrate under reduced pressure. The residue was chromatographed on silica gel eluting with 30-70% ethyl acetate in hexane to afford the title compound. $^1$H NMR (300 MHz, CDCl$_3$) δ ppm 2.71 (t, J=6.96 Hz, 2H), 3.50 (t, J=6.96 Hz, 2H), 4.37 (br s, 1H), 6.67 (d, J=7.80 Hz, 1H), 6.74 (t, J=7.46 Hz, 1H), 7.30 (td, J=7.71, 1.53 Hz, 1H), 7.85 (dd, J=7.80, 1.70 Hz, 1H). MS (DCI) m/z 148.02 (M+H)$^+$.

Example 15C

1-Benzyl-2,3-dihydroquinolin-4(1H)-one

Example 15B (1.32 g, 9.0 mmol), benzyl bromide (1.12 mL, 9.45 mmol) and diisopropylethylamine (3.14 mL, 18.0 mmol) in acetonitrile (12 mL) were heated on a microwave at 150° C. for 30 minutes. Ethyl acetate (200 mL) was added and the organic layer was washed twice with water (200 mL) and brine, dried over sodium sulfate, filtered, concentrate under reduced pressure, and chromatographed on silica gel eluting with 0-to-40% ethyl acetate in hexane to afford the title compound. $^1$H NMR (300 MHz, DMSO-d$_6$) δ ppm 2.68 (t, J=7.12 Hz, 2H), 3.63 (t, J=6.95 Hz, 2H), 4.64 (s, 2H), 6.66 (t, J=6.95 Hz, 1H), 6.78 (d, J=8.82 Hz, 1H), 7.31 (m, 6H), 7.70 (dd, J=7.80, 1.70 Hz, 1H). MS (DCI) m/z 238.09 (M+H)$^+$.

Example 15D

1-Benzyl-2,3-dihydroquinolin-4(1H)-one O-methyl oxime

Methoxyl amine hydrochloride (0.74 g, 8.9 mmol) was added to a solution of Example 15C (1.92 g, 8.1 mmol) in pyridine (20 mL) and stirred overnight at ambient temperature. The mixture was concentrate under reduced pressure, ethyl acetate (200 mL) was added, and the organic layer was washed twice with water (200 mL) and brine, dried over sodium sulfate, filtered, and concentrate under reduced pressure. The residue was chromatographed on silica gel eluting with 0-20% ethyl acetate in hexane to afford the title compound. $^1$H NMR (300 MHz, CDCl$_3$) δ ppm 2.88 (t, J=6.44 Hz, 2H), 3.29 (t, J=6.44 Hz, 2H), 3.97 (s, 3H), 4.47 (s, 2H), 6.65 (d, J=8.14 Hz, 1H), 6.70 (t, J=7.46 Hz, 1H), 7.13 (td, J=7.80, 1.70 Hz, 1H), 7.31 (m, 5H), 7.92 (dd, J=7.80, 1.70 Hz, 1H). MS (DCI) m/z 267.11 (M+H)$^+$.

Example 15E

1-Benzyl-1,2,3,4-tetrahydroquinolin-4-amine

Example 15D (2.11 g, 7.92 mmol) was added to a mixture of 20% ammonia in methanol (80 mL) and Raney nickel (20 g) in a Parr shaker. The glass reactor was sealed and flushed with nitrogen, and pressurized with hydrogen (60 psi). The mixture was shaken at ambient temperature for 4 hours. The solids were filtered off and washed with methanol, and the filtrate was concentrated under reduced pressure to afford the title compound. $^1$H NMR (300 MHz, CDCl$_3$) δ ppm 1.48 (br s, 2H), 1.88 (m, 1H), 2.10 (m, 1H), 3.34 (m, 1H), 3.52 (td, J=10.94, 3.56 Hz, 1H), 4.05 (br s, 1H), 4.51 (s, 2H), 6.53 (d, J=8.48 Hz, 1H), 6.64 (t, J=7.29 Hz, 1H), 7.03 (m, 1H), 7.27 (m, 6H). MS (DCI) m/z 239.1 (M+H)$^+$.

Example 15F

N-(1-Benzyl-1,2,3,4-tetrahydroquinolin-4-yl)-N'47-hydroxy-5,6,7,8-tetrahydronaphthalen-1-yl)urea Di(N-succinimidyl) carbonate (538 mg, 2.1 mmol) was suspended in acetonitrile (5 mL) followed by the addition of Example 1G (555 mg, 2.0 mmol) dissolved in acetonitrile (5 mL) and pyridine (0.17 mL, 2.1 mmol). The mixture was stirred for 15 minutes at ambient temperature and Example 15E (477 mg, 2.0 mmol) dissolved in acetonitrile (10 mL) and diisopropylethylamine (1.05 mL, 6.0 mmol) were added and the mixture stirred for 30 minutes. The mixture was concentrated under reduced pressure and chromatographed on silica gel eluting with 0-30% ethyl acetate in hexane, to afford 1-(1-benzyl-1,2,3,4-tetrahydroquinolin-4-yl)-3-(7-(tert-butyldimethylsilyloxy)-5,6,7,8-tetrahydronaphthalen-1-yl) urea. The intermediate was dissolved in tetrahydrofuran (20 mL), tetrabutylammonium fluoride (1.0M in THF, 4.0 mL, 4.0 mmol) was added, and the mixture stirred overnight at ambient temperature. The mixture was concentrated under reduced pressure and chromatographed on silica gel eluting with 0-10% methanol in ethyl acetate. The residue was suspended in methanol (30 mL), sonicated after which water (300 mL) was added. The sonication was repeated, and the solids were collected by filtration, rinsed with water, and freeze-dried overnight to afford the title compound. $^1$H NMR (300 MHz, DMSO-d$_6$) δ ppm 1.57 (m, 1H), 1.86 (m, 1H), 2.00 (m, 2H), 2.31 (m, 1H), 2.75 (m, 3H), 3.42 (m, 2H), 3.91 (m, 1H), 4.54 (d, J=4.07 Hz, 2H), 4.79 (m, 1H), 4.84 (d, J=4.07 Hz, 1H), 6.53 (d, J=8.13 Hz, 1H), 6.55 (t, J=7.29 Hz, 1H), 6.69 (d, J=7.46 Hz, 1H), 6.99 (m, 3H), 7.13 (d, J=7.12 Hz, 1H), 7.29 (m, 5H), 7.49 (s, 1H), 7.77 (dd, J=7.63, 3.22 Hz, 1H). MS (ESI) m/z 428.2 (M+H)$^+$. Calcd for $C_{27}H_{29}N_3O_2 \cdot 0.42H_2O$: C, 74.53; H, 6.91; N, 9.66. Found: C, 74.56; H, 7.06; N, 9.60.

Example 16

N-[1-Benzyl-7-(trifluoromethyl)-1,2,3,4-tetrahydroquinolin-4-yl]-N'-(7-hydroxy-5,6,7,8-tetrahydronaphthalen-1-yl)urea Example 16A 3-Bromo-N-(3-(trifluoromethyl)phenyl)propanamide 3-(Trifluoromethyl)aniline (Aldrich, 16.11 g, 100 mmol) was added to a suspension of potassium carbonate (27.64 g, 200 mmol) in dichloromethane (225 mL) followed by the addition of 3-bromopropionyl chloride (10.08 mL, 100 mmol) in dichloromethane (40 mL). The mixture was stirred for 4 hours at ambient temperature, quenched with water (200 mL), the organic layer was washed twice with water (200 mL), dried over sodium sulfate, filtered through a silica gel plug, and rinsed with 1:1 ethyl acetate:hexane (400 mL), and concentrated under reduced pressure to afford the title compound. $^1$H NMR (300 MHz, DMSO-$d_6$) δ ppm 2.99 (t, J=6.27 Hz, 2H), 3.74 (t, J=6.44 Hz, 2H), 7.41 (d, J=7.80 Hz, 1H), 7.56 (t, J=7.97 Hz, 1H), 7.77 (d, J=8.48 Hz, 1H), 8.11 (s, 1H), 10.39 (s, 1H). MS (DCI) m/z 312.99 (M+NH$_4$)$^+$.

Example 16B 1-(3-(Trifluoromethyl)phenyl)azetidin-2-one

Sodium tert-butoxide (9.58 g, 100 mmol) was suspended in dimethylformamide (300 mL) and stirred for an hour at ambient temperature. Example 16A (30.13 g, 102 mmol) in dimethylformamide (50 mL) was added and the mixture stirred for 2.5 hours. The mixture was partitioned between tert-butyl methyl ether (1.0 L) and water (1.0 L), and the organic layer was washed with brine, dried over sodium sulfate, filtered, and concentrated under reduced pressure to afford the title compound. $^1$H NMR (300 MHz, DMSO-$d_6$) δ ppm 3.13 (t, J=4.58 Hz, 2H), 3.71 (t, J=4.58 Hz, 2H), 7.44 (m, 1H), 7.60 (m, 2H), 7.67 (s, 1H). MS (DCI) m/z 233.05 (M+NH$_4$)$^+$.

Example 16C 7-(Trifluoromethyl)-2,3-dihydroquinolin-4(1H)-one and 5-(Trifluoromethyl)-2,3-dihydroquinolin-4(1H)-one To a solution of Example 16B (10.75 g, 50 mmol) dissolved in dichloroethane (500 mL) was added trifluoromethanesulfonic acid (15.0 g, 100 mmol), and the mixture was stirred at 75° C. for 4 hours. After cooling potassium carbonate (50 g) and water (500 mL) were added. The organic layer was washed with water (500 mL) and brine, and dried over sodium sulfate, concentrated under reduced pressure to afford the title compound as a mixture of regioisomers: ~45% 7-(trifluoromethyl)-2,3-dihydroquinolin-4(1H)-one and ~55% 5-(trifluoromethyl)-2,3-dihydroquinolin-4(1H)-one. MS (DCI) m/z 233.07 (M+NH$_4$)$^+$.

Example 16D 7-(Trifluoromethyl)-2,3-dihydroquinolin-4(1H)-one O-methyl oxime

Methoxylamine hydrochloride (4.14 g, 49.5 mmol) was added to a solution of Example 16C (9.69 g, 45.0 mmol) in pyridine (40 mL), and mixture was stirred overnight at ambient temperature. Only one regioisomer, 7-(trifluoromethyl)-2,3-dihydroquinolin-4(1H)-one was converted to the oxime. The mixture was concentrated under reduced pressure and ethyl acetate (300 mL) was added. The organic layer was washed twice with water (300 mL) and brine, dried over sodium sulfate, and concentrate under reduced pressure. The residue was chromatographed on silica gel eluting with 20-70% ethyl acetate in hexane to afford the title compound. $^1$H NMR (300 MHz, DMSO-$d_6$) δ ppm 2.70 (t, J=6.61 Hz, 2H), 3.19 (td, J=6.53, 1.86 Hz, 2H), 3.90 (s, 3H), 6.57 (s, 1H), 6.82 (dd, J=8.14, 1.70 Hz, 1H), 6.97 (s, 1H), 7.79 (d, J=8.14 Hz, 1H). MS (DCI) m/z 245.05 (M+H)$^+$.

Example 16E

1-Benzyl-7-(trifluoromethyl)-2,3-dihydroquinolin-4 (1H)-one O-methyl oxime

A mixture of Example 16D (1.71 g, 7.0 mmol), benzyl bromide (0.88 mL, 7.35 mmol), diisopropylethylamine (2.44 mL, 14.0 mmol) in acetonitrile (12 mL) were heated in a microwave Personal Chemistry at 150° C. for 40 minutes. Ethyl acetate (200 mL) was added and the organic layer was washed twice with water (200 mL) and brine, dried over sodium sulfate, filtered, concentrate under reduced pressure, and chromatographed on silica gel eluting with 0-10% ethyl acetate in hexane to afford the title compound. $^1$H NMR (300 MHz, DMSO-$d_6$) δ ppm 2.84 (t, J=6.61 Hz, 2H), 3.39 (t, J=6.61 Hz, 2H), 3.93 (s, 3H), 4.60 (s, 2H), 6.90 (m, 2H), 7.31 (m, 5H), 7.90 (d, J=8.81 Hz, 1H). MS (DCI) m/z 335.10 (M+H)$^+$.

Example 16F

1-Benzyl-7-(trifluoromethyl)-1,2,3,4-tetrahydroquinolin-4-amine

Example 16E (2.10 g, 6.28 mmol) was added to a mixture of 20% ammonia in methanol (100 mL) and Raney nickel (21 g) in a Parr shaker. The glass reactor was sealed and flushed with nitrogen, and pressurized with hydrogen (60 psi). The mixture was shaken at ambient temperature for 4 hours. The solids were filtered off, washed with methanol, and the filtrate was concentrated under reduced pressure to afford the title compound. $^1$H NMR (300 MHz, CDCl$_3$) δ ppm 1.48 (br s, 2H), 1.88 (m, 1H), 2.07 (m, 1H), 3.37 (m, 1H), 3.53 (m, 1H), 4.06 (br s, 1H), 4.54 (s, 2H), 6.75 (s, 1H), 6.86 (d, J=7.80 Hz, 1H), 7.31 (m, 6H). MS (DCI) m/z 307.1 (M+H)$^+$.

Example 16G

N-[1-Benzyl-7-(trifluoromethyl)-1,2,3,4-tetrahydroquinolin-4-yl]-N'-(7-hydroxy-5,6,7,8-tetrahydronaphthalen-1-yl)urea Di(N-succinimidyl) carbonate (538 mg, 2.1 mmol) was suspended in acetonitrile (5 mL) followed by the addition of Example 1G (555 mg, 2.0 mmol) dissolved in acetonitrile (5 mL) and pyridine (0.17 mL, 2.1 mmol). The mixture stirred for 15 minutes at ambient temperature after which Example 16F (613 mg, 2.0 mmol) dissolved in acetonitrile (10 mL) and diisopropylethylamine (1.05 mL, 6.0 mmol) was added and the mixture stirred for 30 minutes. The mixture was concentrated under reduced pressure and chromatographed on silica gel eluting with 0-to-30% ethyl acetate in hexane, to afford 1-(1-benzyl-7-(trifluoromethyl)-1,2,3,4-tetrahydroquinolin-4-yl)-3-(7-(tert-butyldimethylsilyloxy)-5,6,7,8-tetrahydronaphthalen-1-yl)urea. The intermediate was dissolved in tetrahydrofuran (20 mL), and tetrabutylammonium fluoride (1.0M in THF, 4.0 mL, 4.0 mmol) was added and the mixture stirred overnight at ambient temperature. The mixture was concentrated under reduced pressure and chromatographed on silica gel eluting with 0-to-10% methanol in ethyl acetate. The residue was suspended in methanol (30 mL), sonicated, and water was added (300 mL). The sonication was repeated and the solids were collected by filtration, rinsed with water, and freeze-dried to afford the title compound. $^1$H NMR (300 MHz, DMSO-$d_6$) δ ppm 1.59 (m, 1H), 1.87 (m, 1H), 2.04 (m, 2H), 2.31 (m, 1H), 2.76 (m, 3H), 3.50 (m, 2H), 3.92 (m, 1H), 4.63 (d, J=3.05 Hz, 2H), 4.86 (d, J=4.07 Hz, 1H), 4.89 (m, 1H), 6.72 (m, 2H), 6.84 (d, J=7.46 Hz, 1H), 7.00 (t, J=7.80 Hz, 1H), 7.04 (d, J=7.46 Hz, 1H), 7.27 (m, 3H), 7.35 (m, 3H), 7.51 (s, 1H), 7.75 (d, J=9.15 Hz, 1H). MS (ESI) m/z 496.2 (M+H)$^+$. Calcd for C$_{28}$H$_{28}$F$_3$N$_3$O$_2$.0.04H$_2$O: C, 67.77; H, 5.70; N, 8.47. Found: C, 67.79; H, 5.85; N, 8.41.

Example 17

N-(7-Hydroxy-5,6,7,8-tetrahydronaphthalen-1-yl)-N'-(1-methyl-1,2,3,4-tetrahydroquinolin-4-yl)urea

Example 17A

1-Methyl-2,3-dihydroquinolin-4(1H)-one

Example 15B (1.62 g, 11.0 mmol), iodomethane (0.72 mL, 11.55 mmol), potassium carbonate (1.52 g, 11.0 mmol) in dimethylformamide (12 mL) were heated in a microwave at 120° C. for 1 hour. Ethyl acetate (200 mL) was added and the mixture was washed twice with water (200 mL) and brine, dried over sodium sulfate, filtered, and concentrate under reduced pressure. The residue was chromatographed on silica gel eluting with 10-60% ethyl acetate in hexane to afford the title compound. $^1$H NMR (300 MHz, DMSO-$d_6$) δ ppm 2.63 (t, J=6.95 Hz, 2H), 2.94 (s, 3H), 3.45 (t, J=6.95 Hz, 2H), 6.71 (t, J=6.95 Hz, 1H), 6.84 (d, J=8.48 Hz, 1H), 7.42 (ddd, J=8.56, 7.04, 1.70 Hz, 1H), 7.68 (dd, J=7.80, 2.03 Hz, 1H). MS (DCI) m/z 162.05 (M+H)$^+$.

Example 17B

1-Methyl-2,3-dihydroquinolin-4(1H)-one O-methyl oxime

Methoxylamine hydrochloride (0.88 g, 10.6 mmol) was added to a solution of Example 17A (1.55 g, 9.6 mmol) in pyridine (20 mL) and the mixture stirred overnight at ambient temperature. The mixture was concentrated under reduced pressure and ethyl acetate (200 mL) was added. The organic layer was washed twice with water (200 mL) and brine, dried over sodium sulfate, filtered, and concentrate under reduced pressure. The residue was chromatographed on silica gel eluting with 0-20% ethyl acetate in hexane to afford the title compound. $^1$H NMR (300 MHz, DMSO-$d_6$) δ ppm 2.76 (t, J=6.61 Hz, 2H), 2.83 (s, 3H), 3.11 (t, J=6.61 Hz, 2H), 3.87 (s, 3H), 6.69 (t, J=7.46 Hz, 1H), 6.75 (d, J=8.48 Hz, 1H), 7.22 (td, J=7.80, 1.70 Hz, 1H), 7.73 (dd, J=7.80, 1.70 Hz, 1H). MS (DCI) m/z 191.07 (M+H)$^1$.

Example 17C

1-Methyl-1,2,3,4-tetrahydroquinolin-4-amine

Example 17B (1.72 g, 9.06 mmol) was added to a mixture of 20% ammonia in methanol (100 mL) and Raney nickel (18 g) in a Parr shaker. The glass reactor was sealed and flushed with nitrogen and pressurized with hydrogen (60 psi). The mixture was shaken at ambient temperature for 4 hours. The solids were filtered off, washed with methanol and the filtrate was concentrated under reduced pressure to afford the title compound. $^1$H NMR (300 MHz, CDCl$_3$) δ ppm 1.46 (br s, 2H), 1.83 (m, 1H), 2.07 (m, 1H), 2.91 (s, 3H), 3.20 (m, 1H), 3.33 (ddd, J=11.53, 10.00, 3.56 Hz, 1H), 3.98 (m, 1H), 6.62 (d, J=8.48 Hz, 1H), 6.66 (t, J=7.46 Hz, 1H), 7.13 (m, 1H), 7.19 (d, J=7.46 Hz, 1H). MS (DCI) m/z 163.1 (M+H)$^+$.

Example 17D

N-(7-Hydroxy-5,6,7,8-tetrahydronaphthalen-1-yl)-N'-(1-methyl-1,2,3,4-tetrahydroquinolin-4-yl)urea To a mixture of Di(N-succinimidyl) carbonate (538 mg, 2.1 mmol) suspended in acetonitrile (5 mL) was added Example 1G (555 mg, 2.0 mmol) dissolved in acetonitrile (5 mL) and pyridine (0.17 mL, 2.1 mmol). The mixture stirred for 15 minutes at ambient temperature after which Example 17C (326 mg, 2.0 mmol) dissolved in acetonitrile (10 mL) and diisopropylethylamine (1.05 mL, 6.0 mmol) were added and the mixture stirred for 30 minutes. The mixture was concentrated under reduced pressure and chromatographed on silica gel eluting with 10-40% ethyl acetate in hexane, affording 1-(7-(tert-butyldimethylsilyloxy)-5,6,7,8-tetrahydronaphthalen-1-yl)-3-(1-methyl-1,2,3,4-tetrahydroquinolin-4-yl)urea. The intermediate was dissolved in tetrahydrofuran (20 mL), and tetrabutylammonium fluoride (1.0M in THF, 4.0 mL, 4.0 mmol) was added, and the mixture stirred overnight at ambient temperature. The mixture was concentrated under reduced pressure and chromatographed on silica gel eluting with 0-10% methanol in ethyl acetate. The residue was dissolved in methanol (30 mL), sonicated, and water was added (300 mL). The sonication was repeated and the solids were collected by filtration, rinsed with water, and freeze-dried overnight to afford the title compound. $^1$H NMR (300 MHz, DMSO-$d_6$) δ ppm 1.57 (m, 1H), 1.85 (m, 1H), 1.94 (m, 2H), 2.29 (dd, J=16.45, 7.63 Hz, 1H), 2.73 (m, 3H), 2.87 (s, 3H), 3.22 (m, 2H), 3.91 (m, 1H), 4.75 (m, 1H), 4.84 (d, J=4.07 Hz, 1H), 6.63 (m, 3H), 6.94 (d, J=7.46 Hz, 1H), 6.99 (t, J=7.97 Hz, 1H), 7.10 (m, 2H), 7.45 (s, 1H), 7.76 (d, J=8.14 Hz, 1H). MS (ESI) m/z 352.1 (M+H)$^+$. Calcd for $C_{21}H_{25}N_3O_2 \cdot 0.24H_2O$: C, 70.90; H, 7.22; N, 11.81. Found: C, 70.91; H, 7.21; N, 11.63.

Example 18

N-(7-Hydroxy-5,6,7,8-tetrahydronaphthalen-1-yl)-N'-[1-methyl-7-(trifluoromethyl)-1,2,3,4-tetrahydroquinolin-4-yl]urea

Example 18A

1-Methyl-7-(trifluoromethyl)-2,3-dihydroquinolin-4(1H)-one O-methyl oxime

Example 16D (2.20 g, 9.0 mmol), iodomethane (0.60 mL, 9.45 mmol) and potassium carbonate (1.25 g, 9.0 mmol) in dimethylformamide (12 mL) were heated in a microwave Personal Chemistry at 120° C. for 30 minutes. Ethyl acetate (200 mL) was added and the organic layer was washed twice with water (200 mL), brine, dried over sodium sulfate, filtered, and concentrate under reduced pressure. The residue was chromatographed on silica gel eluting with 0-10% ethyl acetate in hexane to afford the title compound. $^1$H NMR (300 MHz, CDCl$_3$) δ ppm 2.88 (t, J=6.61 Hz, 2H), 2.93 (s, 3H), 3.20 (t, J=6.61 Hz, 2H), 3.99 (s, 3H), 6.86 (s, 1H), 6.94 (d, J=7.80 Hz, 1H), 7.99 (d, J=8.14 Hz, 1H). MS (DCI) m/z 259.05 (M+H)$^+$.

Example 18B

1-Methyl-7-(trifluoromethyl)-1,2,3,4-tetrahydroquinolin-4-amine

Example 18A (1.95 g, 7.55 mmol) was added to a mixture of 20% ammonia in methanol (100 mL) and Raney nickel (20 g) in a Parr shaker. The glass reactor was sealed and flushed with nitrogen and pressurized with hydrogen (60 psi). The mixture was shaken at ambient temperature for 4 hours. The solids were filtered off, washed with methanol, and the filtrate was concentrated under reduced pressure to afford the title compound. $^1$H NMR (300 MHz, CDCl$_3$) δ ppm 1.84 (m, 1H), 2.05 (m, 1H), 2.95 (s, 3H), 3.26 (m, 1H), 3.40 (ddd, J=11.70, 9.66, 4.07 Hz, 1H), 4.00 (t, J=4.75 Hz, 1H), 6.76 (s, 1H), 6.87 (d, J=7.80 Hz, 1H), 7.28 (d, J=7.80 Hz, 1H). MS (DCI) m/z 231.0 (M+H)$^+$.

Example 18C

N-(7-Hydroxy-5,6,7,8-tetrahydronaphthalen-1-yl)-N'-[1-methyl-7-(trifluoromethyl)-1,2,3,4-tetrahydroquinolin-4-yl]urea To a mixture of Di(N-succinimidyl) carbonate (538 mg, 2.1 mmol) suspended in acetonitrile (5 mL) was added Example 1G (555 mg, 2.0 mmol) dissolved in acetonitrile (5 mL) and pyridine (0.17 mL, 2.1 mmol) and the mixture stirred for 15 minutes at ambient temperature. Example 18B (460 mg, 2.0 mmol) dissolved in acetonitrile (10 mL) and diisopropylethylamine (1.05 mL, 6.0 mmol) were added and the mixture stirred for 30 minutes. The mixture was concentrated under reduced pressure and the residue was chromatographed on silica gel eluting with 10-40% ethyl acetate in hexane, to afford 1-(7-(tert-butyl dimethyl silyloxy)-5,6,7,8-tetrahydronaphthalen-1-yl)-3-(1-methyl-7-(trifluoromethyl)-1,2,3,4-tetrahydroquinolin-4-yl)urea. The intermediate was dissolved in tetrahydrofuran (20 mL), tetrabutylammonium fluoride (1.0M in THF, 4.0 mL, 4.0 mmol) was added and the mixture stirred overnight at ambient temperature. The mixture was concentrated under reduced pressure and the residue was chromatographed on silica gel eluting with 0-10% methanol in ethyl acetate. The residue was suspended in methanol (30 mL), sonicated, and water (300 mL) was added. The sonication was repeated and the solids were collected by filtration, rinsed with water, and freeze-dried to afford the title compound. $^1$H NMR (300 MHz, DMSO-d$_6$) δ ppm 1.57 (m, 1H), 1.86 (m, 1H), 1.96 (m, 2H), 2.30 (dd, J=16.78, 7.97 Hz, 1H), 2.76 (m, 3H), 2.94 (s, 3H), 3.91 (m, 1H), 4.83 (m, 2H), 6.70 (d, J=6.78 Hz, 1H), 6.81 (s, 1H), 6.88 (d, J=7.80 Hz, 1H), 6.99 (m, 2H), 7.30 (d, J=7.80 Hz, 1H), 7.47 (s, 1H), 7.74 (d, J=7.80 Hz, 1H). MS (ESI) m/z 420.2 (M+H)$^+$. Calcd for $C_{22}H_{24}F_3N_3O_2$.0.06H$_2$O: C, 62.84; H, 5.78; N, 9.99. Found: C, 62.86; H, 5.78; N, 9.92.

Example 19

N-(1-Benzyl-1,2,3,4-tetrahydroquinolin-3-yl)-N'-(7-hydroxy-5,6,7,8-tetrahydronaphthalen-1-yl)urea Example 19A Ethyl 1,2,3,4-tetrahydroquinoline-3-carboxylate Ethyl quinoline-3-carboxylate (Aldrich, 15.44 g, 76.7 mmol) was added to a mixture of ethanol (150 mL) and 10% palladium on carbon (3.0 g) in a Parr shaker. The glass reactor was sealed and flushed with nitrogen, and pressurized with hydrogen (60 psi). The mixture was shaken at 50° C. for 52 hours. The solids were filtered, rinsed with methanol, concentrate under reduced pressure, and chromatographed on silica gel eluting with 5-40% ethyl acetate in hexane to afford the title compound. $^1$H NMR (300 MHz, DMSO-d$_6$) δ ppm 1.19 (t, J=7.12 Hz, 3H), 2.83 (m, 3H), 3.17 (m, 1H), 3.39 (m, 1H), 4.09 (q, J=7.12 Hz, 2H), 5.74 (s, 1H), 6.44 (m, 2H), 6.86 (m, 2H). MS (DCI) m/z 206.10 (M+H)$^+$.

Example 19B

Ethyl 1-benzyl-1,2,3,4-tetrahydroquinoline-3-carboxylate

Example 19A (6.16 g, 30.0 mmol), benzyl bromide (3.57 mL, 30.0 mmol) and diisopropylethylamine (10.5 mL, 60.0 mmol) in acetonitrile (40 mL) were heated in a microwave at 150° C. for 30 minutes. Ethyl acetate (400 mL) was added and the separated organic layer was washed twice with water (400 mL), brine, dried over sodium sulfate, filtered, and concentrate under reduced pressure. The residue was chromatographed on silica gel eluting with 0-20% ethyl acetate in hexane to afford the title compound. $^1$H NMR (300 MHz, DMSO-d$_6$) δ ppm 1.17 (t, J=7.12 Hz, 3H), 2.96 (m, 3H), 3.48 (m, 2H), 4.09 (q, J=7.12 Hz, 2H), 4.49 (d, J=7.45 Hz, 2H), 6.49 (m, 2H), 6.89 (m, 1H), 6.97 (d, J=7.12 Hz, 1H), 7.26 (m, 5H). MS (DCI) m/z 296.12 (M+H)$^+$.

Example 19C

1-Benzyl-1,2,3,4-tetrahydroquinoline-3-carboxylic acid

Example 19B (8.84 g, 29.9 mmol) was dissolved in tetrahydrofuran (300 mL), 1.0N lithium hydroxide (300 mL) was added and the mixture stirred overnight at ambient temperature. The organic layer was concentrated under reduced pressure and the aqueous layer was neutralized with citric acid (18.12 g, 94.3 mmol) and they were recombined. Water (100 mL) was added and the mixture was extracted twice with ethyl acetate (300 mL), and brine, filtered, and dried over sodium sulfate, filtered and concentrated under reduced pressure to afford the title compound. $^1$H NMR (300 MHz, DMSO-d$_6$) δ ppm 2.88 (m, 3H), 3.49 (m, 2H), 4.49 (s, 2H), 6.48 (m, 2H), 6.88 (t, J=8.14 Hz, 1H), 6.95 (d, J=7.29 Hz, 1H), 7.27 (m, 5H). MS (DCI) m/z 268.10 (M+H)$^+$.

Example 19D tert-Butyl 1-benzyl-1,2,3,4-tetrahydroquinolin-3-ylcarbamate

Example 19C (7.75 g, 29.0 mmol), diphenylphosphoryl azide (6.89 mL, 31.9 mmol), triethylamine (4.85 mL, 34.8 mmol) in tert-butanol (200 mL) were heated at 110° C. for 9 hours. After cooling, the mixture was concentrated under reduced pressure and diluted with 1:1 ethyl acetate:hexane (200 mL). The crystals were filtered off, the filtrate was concentrate under reduced pressure, and the residue was chromatographed on silica gel eluting with 0-30% ethyl acetate in hexane to afford the title compound. $^1$H NMR (300 MHz, CDCl$_3$) δ ppm 1.42 (s, 9H), 2.74 (d, J=16.61 Hz, 1H), 3.13 (d, J=16.11 Hz, 1H), 3.30 (d, J=9.16 Hz, 1H), 3.52 (d, J=12.04 Hz, 1H), 4.21 (br s, 1H), 4.49 (s, 2H), 4.82 (br s, 1H), 6.58 (d, J=8.14 Hz, 1H), 6.63 (t, J=7.46 Hz, 1H), 7.01 (m, 2H), 7.29 (m, 5H). MS (ESI) m/z 339.1 (M+H)$^1$.

Example 19E

1-Benzyl-1,2,3,4-tetrahydroquinolin-3-amine

Example 19D (1.36 g, 4.0 mmol) was dissolved in dichloromethane (10 mL), and trifluoroacetic acid (2 mL) was added and the mixture stirred overnight at ambient temperature. The mixture was concentrated under reduced pressure and 1.0N sodium hydroxide (100 mL) was added. The mixture was extracted twice with ethyl acetate (100 mL). The combined organic layers were washed with brine, dried over sodium sulfate and filtered. The solvent was evaporated to afford the title compound. $^1$H NMR (300 MHz, CDCl$_3$) δ ppm 2.65 (dd, J=15.60, 7.46 Hz, 1H), 3.09 (m, 2H), 3.41 (m, 2H), 4.48 (d, J=6.45 Hz, 2H), 6.56 (d, J=8.81 Hz, 1H), 6.61 (t, J=7.29 Hz, 1H), 7.00 (m, 2H), 7.27 (m, 5H). MS (DCI) m/z 239.08 (M+H)$^+$.

Example 19F

N-(1-Benzyl-1,2,3,4-tetrahydroquinolin-3-yl)-N'47-hydroxy-5,6,7,8-tetrahydronaphthalen-1-yl)urea Di(N-succinimidyl) carbonate (578 mg, 2.26 mmol) was dissolved in acetonitrile (5 mL) followed by the addition of Example 1G (596 mg, 2.15 mmol) dissolved in acetonitrile (5 mL) and pyridine (0.18 mL, 2.26 mmol). The mixture was stirred for 15 minutes at ambient temperature after which Example 19E (512 mg, 2.15 mmol) dissolved in acetonitrile (10 mL) and diisopropylethylamine (1.12 mL, 6.44 mmol) were added and the mixture was stirred for 30 minutes. The mixture was concentrated under reduced pressure and the residue was chromatographed on silica gel eluting with 0-30% ethyl acetate in hexane to afford 1-(1-benzyl-1,2,3,4-tetrahydroquinolin-3-yl)-3-(7-(tert-butyldimethylsilyloxy)-5,6,7,8-tetrahydronaphthalen-1-yl)urea. The intermediate was dissolved in tetrahydrofuran (20 mL) and tetrabutylammonium fluoride (1.0M in THF, 4.3 mL, 4.3 mmol) was added, and the mixture stirred overnight at ambient temperature. The mixture was concentrated under reduced pressure and chromatographed on silica gel eluting with 0-10% methanol in ethyl acetate. The residue was suspended in methanol (20 mL), sonicated, and additional water (200 mL) was added. The sonication was repeated and the solids were collected by filtration, rinsed with water, and freeze-dried to afford the title compound. $^1$H NMR (300 MHz, DMSO-d$_6$) δ ppm 1.57 (m, 1H), 1.86 (m, 1H), 2.31 (m, 1H), 2.74 (m, 4H), 3.08 (m, 1H), 3.52 (d, J=10.85 Hz, 1H), 3.91 (m, 1H), 4.17 (m, 1H), 4.51 (s, 2H), 4.85 (m, 1H), 6.51 (d, J=8.14 Hz, 1H), 6.54 (t, J=7.29 Hz, 1H), 6.69 (d, J=7.46 Hz, 1H), 6.75 (d, J=7.46 Hz, 1H), 6.95 (m, 3H), 7.21 (m, 1H), 7.30 (d, J=4.41 Hz, 4H), 7.65 (d, J=8.13 Hz, 1H), 7.67 (d, J=2.71 Hz, 1H). MS (ESI) m/z 428.29 (M+H)$^+$. Calcd for C$_{27}$H$_{29}$N$_3$O$_2$.0.24H$_2$O: C, 75.09; H, 6.88; N, 9.73. Found: C, 75.12; H, 6.90; N, 9.64.

Example 20

N-[1-Benzyl-7-(trifluoromethyl)-1,2,3,4-tetrahydroquinolin-3-yl]-N'-(7-hydroxy-5,6,7,8-tetrahydronaphthalen-1-yl)urea Example 20A Ethyl 4-chloro-7-(trifluoromethyl)quinoline-3-carboxylate Ethyl 4-hydroxy-7-(trifluoromethyl)quinoline-3-carboxylate (Aldrich, 10.0 g, 35.1 mmol) and phosphorus oxychloride (100 mL, 1.07 mol) were refluxed for 2 hours. After cooling the mixture was poured onto ice (1.0 L) and stirred for 1 hour. The mixture was extracted twice with dichloromethane (500 mL), dried over sodium sulfate, and concentrated under reduced pressure. The residue was chromatographed on silica gel eluting with 0-40% ethyl acetate in hexane to afford the title compound. $^1$H NMR (300 MHz, DMSO-d$_6$) δ ppm 1.40 (t, J=7.12 Hz, 3H), 4.46 (q, J=7.12 Hz, 2H), 8.14 (d, J=8.82 Hz, 1H), 8.54 (s, 1H), 8.62 (d, J=8.82 Hz, 1H), 9.30 (s, 1H). MS (ESI) m/z 303.95 (M+H)$^+$.

Example 20B

Ethyl 7-(trifluoromethyl)-1,2,3,4-tetrahydroquinoline-3-carboxylate

Example 20A (8.55 g, 28.0 mmol) was added to a mixture of tetrahydrofuran (100 mL), ethanol (200 mL), and 5% palladium on carbon (1.7 g) in a Parr shaker. The glass reactor was sealed and flushed with nitrogen and pressurized with hydrogen (60 psi). The mixture was shaken at 50° C. for 16 hours after which the solids were filtered, rinsed with methanol, and the filtrated concentrated under reduced pressure. Ethyl acetate (200 mL) was added and the organic layer was washed with saturated sodium bicarbonate (200 mL), brine, dried over sodium sulfate, filtered and concentrated under reduced pressure. The residue was chromatographed on silica gel eluting with 0-40% ethyl acetate in hexane to afford the title compound. $^1$H NMR (300 MHz, CDCl$_3$) δ ppm 1.27 (t, J=7.12 Hz, 3H), 2.90 (m, 1H), 3.03 (d, J=7.46 Hz, 2H), 3.41 (dd, J=11.52, 8.81 Hz, 1H), 3.58 (dd, J=11.53, 3.73 Hz, 1H), 4.06 (br s, 1H), 4.19 (q, J=7.23 Hz, 2H), 6.71 (s, 1H), 6.85 (d, J=8.14 Hz, 1H), 7.07 (d, J=7.80 Hz, 1H). MS (DCI) m/z 274.05 (M+H)$^+$.

Example 20C

Ethyl 1-benzyl-7-(trifluoromethyl)-1,2,3,4-tetrahydroquinoline-3-carboxylate

Example 20B (4.10 g, 15.0 mmol), benzyl bromide (1.78 mL, 15.0 mmol) and diisopropylethylamine (5.22 mL, 30.0 mmol) in acetonitrile (20 mL) were heated in a microwave at 150° C. for 30 minutes. Ethyl acetate (200 mL) was added, and the organic layer was washed twice with water (200 mL), brine, dried over sodium sulfate, filtered, and concentrate under reduced pressure. The residue was chromatographed on silica gel eluting with 0-20% ethyl acetate in hexane to afford the title compound. $^1$H NMR (300 MHz, CDCl$_3$) δ ppm 1.25 (t, J=7.12 Hz, 3H), 2.98 (m, 1H), 3.08 (d, J=7.12 Hz, 2H), 3.54 (m, 2H), 4.16 (qd, J=7.12, 2.03 Hz, 2H), 4.53 (s, 2H), 6.77 (s, 1H), 6.85 (d, J=7.46 Hz, 1H), 7.10 (d, J=7.46 Hz, 1H), 7.25 (m, 2H), 7.31 (m, 3H). MS (DCI) m/z 364.14 (M+H)$^+$.

Example 20D

1-Benzyl-7-(trifluoromethyl)-1,2,3,4-tetrahydroquinoline-3-carboxylic acid

Example 20C (5.15 g, 14.2 mmol) was dissolved in tetrahydrofuran (150 mL), and 1.0N lithium hydroxide (150 mL) was added. The mixture was stirred overnight at ambient temperature. The organic layer was separated, the aqueous layer was neutralized with citric acid (6.68 g, 34.8 mmol) and they were recombined. Water (100 mL) was added and the mixture was extracted twice with ethyl acetate (300 mL). The combined organic layers were washed with brine and dried over sodium sulfate, and concentrated under reduced pressure to afford the title compound. $^1$H NMR (300 MHz, DMSO-d$_6$) δ ppm 2.99 (m, 3H), 3.58 (m, 2H), 4.57 (s, 2H), 6.66 (s, 1H), 6.79 (d, J=7.80 Hz, 1H), 7.17 (d, J=7.80 Hz, 1H), 7.28 (m, 5H), 12.58 (br s, 1H). MS (DCI) m/z 336.08 (M+H)$^+$.

Example 20E tert-Butyl 1-benzyl-7-(trifluoromethyl)-1,2,3,4-tetrahydroquinolin-3-ylcarbamate Example 20D (4.63 g, 13.8 mmol), diphenylphosphoryl azide (3.3 mL, 15.2 mmol) and triethylamine (2.31 mL, 16.6 mmol) in tert-butanol (100 mL) were heated at 100° C. for 4.5 hours. After cooling, the mixture was concentrated under reduced pressure and chromatographed on silica gel eluting with 0-30% ethyl acetate in hexane to afford the title compound. $^1$H NMR (300 MHz, CDCl$_3$) δ ppm 1.43 (s, 9H), 2.78 (dd, J=16.11, 4.24 Hz, 1H), 3.12 (d, J=16.61 Hz, 1H), 3.32 (d, J=10.85 Hz, 1H), 3.54 (d, J=12.21 Hz, 1H), 4.21 (br s, 1H), 4.51 (s, 2H), 4.71 (br s, 1H), 6.80 (s, 1H), 6.86 (d, J=7.80 Hz, 1H), 7.06 (d, J=7.46 Hz, 1H), 7.25 (m, 2H), 7.30 (m, 3H). MS (ESI) m/z 407.1 (M+H)$^+$.

Example 20F

1-Benzyl-7-(trifluoromethyl)-1,2,3,4-tetrahydroquinolin-3-amine

To Example 20E (1.22 g, 3.0 mmol) dissolved in dichloromethane (10 mL) was added trifluoroacetic acid (2 mL) and the mixture stirred overnight at ambient temperature. The mixture was concentrated under reduced pressure and 1.0M potassium carbonate (100 mL), was added and the mixture was extracted twice with ethyl acetate (100 mL). The combined organic layers were washed with brine, dried over sodium sulfate, filtered and concentrate under reduced pressure. The residue was chromatographed on silica gel eluting with 0-10% methanol in dichloromethane to afford the title compound. $^1$H NMR (300 MHz, CDCl$_3$) δ ppm 2.66 (dd, J=16.28, 7.46 Hz, 1H), 3.06 (d, J=15.26 Hz, 1H), 3.14 (m, 1H), 3.43 (m, 2H), 4.51 (d, J=4.07 Hz, 2H), 6.78 (s, 1H), 6.84 (m, 1H), 7.06 (d, J=7.46 Hz, 1H), 7.24 (m, 2H), 7.31 (m, 3H). MS (DCI) m/z 307.08 (M+H)$^+$.

Example 20G

N-[1-Benzyl-7-(trifluoromethyl)-1,2,3,4-tetrahydroquinolin-3-yl]-N'-(7-hydroxy-5,6,7,8-tetrahydronaphthalen-1-yl)urea To Di(N-succinimidyl) carbonate (517 mg, 2.02 mmol) dissolved in acetonitrile (5 mL) was added Example 1G (534 mg, 1.92 mmol) dissolved in acetonitrile (5 mL) and pyridine (0.16 mL, 2.02 mmol) and the mixture stirred for 15 minutes at ambient temperature. Example 20F (589 mg, 1.92 mmol) dissolved in acetonitrile (10 mL) and diisopropylethylamine (1.0 mL, 5.77 mmol) were added and the mixture stirred for 30 minutes. The mixture was concentrated under reduced pressure and the residue was chromatographed on silica gel eluting with 0-30% ethyl acetate in hexane to afford 1-(1-benzyl-7-(trifluoromethyl)-1,2,3,4-tetrahydroquinolin-3-yl)-3-(7-(tert-butyldimethylsilyloxy)-5,6,7,8-tetrahydronaphthalen-1-yl)urea. The intermediate was dissolved in tetrahydrofuran (20 mL) and tetrabutylammonium fluoride (1.0M in THF, 3.85 mL, 3.85 mmol) was added, and the mixture stirred overnight at ambient temperature. The mixture was concentrated under reduced pressure and the residue was chromatographed on silica gel eluting with 0-10% methanol in ethyl acetate. The solid was suspended in methanol (20 mL), sonicated, and water (200 mL) was added. The sonication was repeated, and the solids were collected by filtration, rinsed with water, and freeze-dried to afford the title compound. $^1$H NMR (300 MHz, DMSO-d$_6$) δ ppm 1.57 (m, 1H), 1.86 (m, 1H), 2.30 (dd, J=16.45, 7.63 Hz, 1H), 2.73 (m, 4H), 3.15 (d, J=16.96 Hz, 1H), 3.61 (d, J=11.53 Hz, 1H), 3.91 (m, 1H), 4.22 (m, 1H), 4.58 (s, 2H), 4.86 (t, J=3.73 Hz, 1H), 6.71 (m, 2H), 6.75 (d, J=7.80 Hz, 1H), 6.83 (d, J=7.80 Hz, 1H), 6.97 (t, J=7.80 Hz, 1H), 7.19 (d, J=7.80 Hz, 1H), 7.23 (m, 1H), 7.31 (m, 4H), 7.66 (m, 2H). MS (DCI) m/z 496.20 (M+H)$^+$. Calcd for C$_{29}$H$_{28}$F$_3$N$_3$O$_2$.0.17H$_2$O: C, 67.45; H, 5.73; N, 8.43. Found: C, 67.44; H, 5.69; N, 8.42, 6.88; N, 9.73. Found: C, 75.12; H, 6.90; N, 9.64.

Example 21

N-(7-Hydroxy-5,6,7,8-tetrahydronaphthalen-1-yl)-N'-(1-methyl-1,2,3,4-tetrahydroquinolin-3-yl)urea

Example 21A tert-Butyl 1,2,3,4-tetrahydroquinolin-3-ylcarbamate

Example 19D (4.05 g, 12.0 mmol) was added to a mixture of methanol (100 mL) and 20% palladium hydroxide on carbon (0.8 g) in a Parr shaker. The glass reactor was sealed and flushed with nitrogen, and pressurized with hydrogen (60 psi). The mixture was shaken at ambient temperature for 16 hours. The solids were filtered, rinsed with methanol, and the filtrate was concentrate under reduced pressure. The residue was chromatographed on silica gel eluting with 0-35% ethyl acetate in hexane to afford the title compound. $^1$H NMR (300 MHz, CDCl$_3$) δ ppm 1.43 (s, 9H), 2.71 (d, J=16.27 Hz, 1H), 3.05 (dd, J=16.45, 4.58 Hz, 1H), 3.21 (d, J=9.84 Hz, 1H), 3.38 (dd, J=11.36, 2.20 Hz, 1H), 3.82 (br s, 1H), 4.17 (br s, 1H), 4.98 (br s, 1H), 6.52 (d, J=7.80 Hz, 1H), 6.66 (t, J=7.29 Hz, 1H), 6.98 (m, 2H). MS (DCI) m/z 249.11 (M+H)$^+$.

Example 21B tert-Butyl 1-methyl-1,2,3,4-tetrahydroquinolin-3-ylcarbamate

Example 21A (880 mg, 3.54 mmol), sodium bicarbonate (536 mg, 6.38 mmol), dimethoxyethane (7 mL) and water (7 mL) were combined and dimethyl sulfate (0.44 mL, 4.61 mmol) was added and the mixture stirred overnight at ambient temperature. Ethyl acetate (200 mL) was added and the separated organic layer was washed with saturated sodium bicarbonate (200 mL), brine, dried over sodium sulfate, filtered and concentrate under reduced pressure. The residue was chromatographed on silica gel eluting with 5-35% ethyl acetate in hexane to afford the title compound. $^1$H NMR (300 MHz, CDCl$_3$) δ ppm 1.43 (s, 9H), 2.73 (d, J=16.27 Hz, 1H), 2.90 (s, 3H), 3.08 (m, 2H), 3.37 (d, J=13.56 Hz, 1H), 4.19 (br s, 1H), 4.94 (br s, 1H), 6.65 (m, 2H), 6.98 (d, J=7.12 Hz, 1H), 7.12 (t, J=7.80 Hz, 1H). MS (DCI) m/z 263.13 (M+H)$^+$.

Example 21C

1-Methyl-1,2,3,4-tetrahydroquinolin-3-amine

Example 21B (980 mg, 3.74 mmol) was dissolved in dichloromethane (15 mL), and trifluoroacetic acid (3 mL) was added and the mixture stirred for 3 hours at ambient temperature. The mixture was concentrated under reduced pressure to afford the title compound. MS (DCI) m/z 163.08 (M+H)$^+$.

Example 21D

N-(7-Hydroxy-5,6,7,8-tetrahydronaphthalen-1-yl)-
N'-(1-methyl-1,2,3,4-tetrahydroquinolin-3-yl)urea To Di(N-succinimidyl) carbonate (1.01 g, 3.92 mmol) dissolved in acetonitrile (5 mL) was added Example 1G (1.04 g, 3.74 mmol) in acetonitrile (10 mL) and pyridine (0.32 mL, 3.92 mmol) and the mixture stirred for 15 minutes at ambient temperature. Example 21C (2.75 g) dissolved in acetonitrile (15 mL) and diisopropylethylamine (5.2 mL, 29.9 mmol) were added and the mixture stirred for 2 hours. Ethyl acetate (200 mL) and saturated sodium bicarbonate (200 mL) were added and the organic layer was washed with brine, dried over sodium sulfate, filtered, and concentrate under reduced pressure. The residue was chromatographed on silica gel eluting with 10-40% ethyl acetate in hexane, to afford 1-(7-(tert-butyldimethylsilyloxy)-5,6,7,8-tetrahydronaphthalen-1-yl)-3-(1-methyl-1,2,3,4-tetrahydroquinolin-3-yl)urea. The intermediate was dissolved in tetrahydrofuran (20 mL), tetrabutylammonium fluoride (1.0M in THF, 6.5 mL, 6.5 mmol) was added and the mixture was stirred overnight at ambient temperature. The mixture was concentrated under reduced pressure and the residue was chromatographed on silica gel eluting with 0-10% methanol in ethyl acetate. The residue was suspended in methanol (20 mL), sonicated, and water (200 mL) was added. The sonication was repeated, and the solids were collected by filtration, rinsed with water, and freeze-dried overnight to afford the title compound. $^1$H NMR (300 MHz, DMSO-$d_6$) δ ppm 1.56 (m, 1H), 1.84 (m, 1H), 2.28 (dd, J=16.62, 7.80 Hz, 1H), 2.71 (m, 4H), 2.87 (s, 3H), 3.03 (m, 2H), 3.36 (m, 1H), 3.89 (m, 1H), 4.12 (m, 1H), 4.81 (d, J=3.05 Hz, 1H), 6.59 (t, J=7.29 Hz, 1H), 6.64 (d, J=8.13 Hz, 1H), 6.68 (d, J=7.46 Hz, 1H), 6.74 (d, J=7.80 Hz, 1H), 6.94 (d, J=7.12 Hz, 1H), 6.97 (t, J=7.80 Hz, 1H), 7.04 (m, 1H), 7.61 (s, 1H), 7.68 (d, J=8.14 Hz, 1H). MS (ESI) m/z 352.17 (M+H)$^+$. Calcd for $C_{21}H_{25}N_3O_2$: C, 71.77; H, 7.17; N, 11.96. Found: C, 71.77; H, 7.16; N, 11.77.

Example 22

N-(7-Hydroxy-5,6,7,8-tetrahydronaphthalen-1-yl)-
N'-[1-methyl-7-(trifluoromethyl)-1,2,3,4-tetrahydroquinolin-3-yl]urea

Example 22A tert-Butyl 7-(trifluoromethyl)-1,2,3,4-tetrahydroquinolin-3-ylcarbamate Example 20E (2.73 g, 6.71 mmol) was added to a mixture of methanol (60 mL) and 20% palladium hydroxide on carbon (0.55 g) in a Parr shaker. The glass reactor was sealed and flushed with nitrogen, and pressurized with hydrogen (60 psi). The mixture was shaken at ambient temperature for 16 hours. The solids were filtered, rinsed with methanol, and the filtrate was concentrate under reduced pressure. The residue was chromatographed on silica gel eluting with 0-40% ethyl acetate in hexane to afford the title compound. $^1$H NMR (300 MHz, CDCl$_3$) δ ppm 1.44 (s, 9H), 2.76 (d, J=16.61 Hz, 1H), 3.05 (dd, J=16.79, 3.90 Hz, 1H), 3.25 (d, J=10.51 Hz, 1H), 3.42 (d, J=11.53, 1H), 4.01 (s, 1H), 4.18 (br s, 1H), 4.86 (br s, 1H), 6.73 (s, 1H), 6.87 (d, J=7.80 Hz, 1H), 7.04 (d, J=7.80 Hz, 1H). MS (DCI) m/z 317.10 (M+H)$^+$.

Example 22B tert-Butyl 1-methyl-7-(trifluoromethyl)-1,2,3,4-tetrahydroquinolin-3-ylcarbamate Example 22A (1.27 g, 4.0 mmol), iodomethane (0.25 mL, 4.0 mmol) and potassium carbonate (553 mg, 4.0 mmol) in dimethylformamide (12 mL) were heated in a microwave Personal Chemistry at 120° C. for 15 minutes. Ethyl acetate (200 mL) was added, and the separated organic layer washed with saturated sodium bicarbonate (200 mL), brine, dried over sodium sulfate, filtered and concentrated under reduced pressure to afford the title compound. $^1$H NMR (300 MHz, CDCl$_3$) δ ppm 1.44 (s, 9H), 2.77 (d, J=16.61 Hz, 1H), 2.94 (s, 3H), 3.06 (dd, J=16.61, 4.07 Hz, 1H), 3.15 (ddd, J=11.53, 4.75, 2.03 Hz, 1H), 3.43 (dd, J=11.36, 2.54 Hz, 1H), 4.20 (br s, 1H), 4.81 (br s, 1H), 6.79 (s, 1H), 6.89 (d, J=7.80 Hz, 1H), 7.04 (d, J=7.12 Hz, 1H). MS (DCI) m/z 331.10 (M+H)$^+$.

Example 22C

1-Methyl-7-(trifluoromethyl)-1,2,3,4-tetrahydroquinolin-3-amine

Example 22B (1.00 g, 3.03 mmol) was dissolved in dichloromethane (15 mL), and trifluoroacetic acid (3 mL) was added and the mixture stirred for 2 hours at ambient temperature. The mixture was concentrated under reduced pressure to afford the title compound. MS (DCI) m/z 231.06 (M+H)$^1$.

Example 22D

N-(7-Hydroxy-5,6,7,8-tetrahydronaphthalen-1-yl)-
N'-[1-methyl-7-(trifluoromethyl)-1,2,3,4-tetrahydroquinolin-3-yl]urea To Di(N-succinimidyl) carbonate (816 mg, 3.18 mmol) in acetonitrile (5 mL) was added Example 1G (842 mg, 3.03 mmol) in acetonitrile (10 mL) and pyridine (0.26 mL, 3.18 mmol) and the mixture stirred for 15 minutes at ambient temperature. Example 22C (1.86 g) dissolved in acetonitrile (15 mL) and diisopropylethylamine (4.2 mL, 24.2 mmol) were added and the mixture stirred overnight. Ethyl acetate (200 mL) was added and the separated organic layer was washed with saturated sodium bicarbonate (200 mL), brine, dried over sodium sulfate, filtered, and concentrate under reduced pressure. The residue was chromatographed on silica gel eluting with 10-40% ethyl acetate in hexane, to afford 1-(7-(tert-butyldimethylsilyloxy)-5,6,7,8-tetrahydronaphthalen-1-yl)-3-(1-methyl-7-(trifluoromethyl)-1,2,3,4-tetrahydroquinolin-3-yl)urea. The intermediate was dissolved in tetrahydrofuran (20 mL), tetrabutylammonium fluoride (1.0M in THF, 5.4 mL, 5.4 mmol) was added, and the mixture stirred overnight at ambient temperature. The mixture was concentrated under reduced pressure and chromatographed on silica gel eluting with 0-10% methanol in ethyl acetate. The residue was suspended methanol (20 mL), sonicated, and water (200 mL) was added. The sonication was repeated, and the solids were collected by filtration, rinsed with water, and freeze-dried to afford the title compound. $^1$H NMR (300 MHz, DMSO-$d_6$) δ ppm 1.56 (m, 1H), 1.84 (m, 1H), 2.27 (dd, J=16.78, 7.29 Hz, 1H), 2.73 (m, 4H), 2.94 (s, 3H), 3.06 (dd, J=16.11, 4.24 Hz, 1H), 3.15 (dd, J=11.36, 5.26 Hz, 1H), 3.45 (dd, J=11.19, 3.05 Hz, 1H), 3.89 (m, 1H), 4.16 (m, 1H), 4.81 (d, J=3.73 Hz, 1H), 6.69 (d, J=7.46 Hz, 1H), 6.74 (d, J=7.46 Hz, 1H), 6.81 (s, 1H), 6.87 (d, J=7.80 Hz, 1H), 6.97 (t, J=7.80 Hz, 1H), 7.15 (d, J=7.80 Hz, 1H), 7.58 (s, 1H), 7.68 (d, J=7.80

Hz, 1H). MS (ESI) m/z 420.23 (M+H)[1]. Calcd for $C_{22}H_{24}F_3N_3O_2$: C, 63.00; H, 5.77; N, 10.02. Found: C, 62.96; H, 5.59; N, 9.89.

Example 23

N-[(1-Benzyl-1,2,3,4-tetrahydroquinolin-2-yl)methyl]-N'-(7-hydroxy-5,6,7,8-tetrahydronaphthalen-1-yl)urea

Example 23A

Ethyl quinoline-2-carboxylate

Quinoline-2-carboxylic acid (Aldrich, 10.0 g, 57.7 mmol) was added to ethanol (500 mL) and sulfuric acid (25 mL) and refluxed for 7 hours. The mixture was concentrated under reduced pressure and dichloromethane (400 mL) was added. The organic layer was washed twice with saturated sodium bicarbonate (400 mL), dried with sodium sulfate, filtered and concentrated under reduced pressure to afford the title compound. $^1$H NMR (300 MHz, DMSO-$d_6$) δ ppm 1.39 (t, J=7.12 Hz, 3H), 4.43 (q, J=7.12 Hz, 2H), 7.76 (ddd, J=8.14, 6.95, 1.19 Hz, 1H), 7.88 (ddd, J=8.48, 6.95, 1.53 Hz, 1H), 8.11 (m, 2H), 8.18 (d, J=8.48 Hz, 1H), 8.58 (d, J=8.48 Hz, 1H). MS (DCI) m/z 202.05 (M+H)[1].

Example 23B

Ethyl 1,2,3,4-tetrahydroquinoline-2-carboxylate

Example 23A (10.77 g, 53.5 mmol) was added to a mixture of acetic acid (400 mL) and 5% platinum on carbon (2.0 g) in a Parr shaker. The glass reactor was sealed and flushed with nitrogen, and pressurized with hydrogen (60 psi). The mixture was shaken at ambient temperature for 2 hours. The solids were filtered, rinsed with methanol and the filtrate was concentrate under reduced pressure. Ethyl acetate (200 mL) was added and the organic layer was washed with saturated sodium bicarbonate (200 mL) and brine, dried over sodium sulfate, filtered and concentrate under reduced pressure. The residue was chromatographed on silica gel eluting with 0-25% ethyl acetate in hexane to afford the title compound. $^1$H NMR (300 MHz, DMSO-$d_6$) δ ppm 1.20 (t, J=7.12 Hz, 3H), 1.98 (q, J=6.27 Hz, 2H), 2.56 (t, J=7.29 Hz, 1H), 2.67 (dt, J=16.36, 5.89 Hz, 1H), 4.02 (td, J=5.17, 2.54 Hz, 1H), 4.12 (qd, J=7.12, 1.70 Hz, 2H), 5.93 (d, J=2.03 Hz, 1H), 6.44 (td, J=7.46, 1.02 Hz, 1H), 6.55 (d, J=7.80 Hz, 1H), 6.84 (m, 2H). MS (DCI) m/z 206.10 (M+H)[1].

Example 23C

Ethyl 1-benzyl-1,2,3,4-tetrahydroquinoline-2-carboxylate

Example 23B (2.46 g, 12.0 mmol), benzyl bromide (1.5 mL, 12. mmol) and diisopropylethylamine (4.2 mL, 24.0 mmol) in acetonitrile (16 mL) were heated in a microwave at 150° C. for 30 minutes. Ethyl acetate (200 mL) was added and the separated organic layer was washed twice with water (200 mL), brine, dried over sodium sulfate, filtered, and concentrate under reduced pressure. The residue was chromatographed on silica gel eluting with 0-20% ethyl acetate in hexane to afford the title compound. $^1$H NMR (300 MHz, DMSO-$d_6$) δ ppm 1.17 (t, J=6.96 Hz, 3H), 2.11 (m, 1H), 2.28 (m, 1H), 2.61 (dd, J=12.89, 5.09 Hz, 1H), 2.70 (d, J=16.28 Hz, 1H), 4.10 (t, J=7.46 Hz, 2H), 4.30 (t, J=3.57 Hz, 1H), 4.36 (d, J=17.29 Hz, 1H), 4.63 (d, J=16.95 Hz, 1H), 6.39 (d, J=8.14 Hz, 1H), 6.50 (t, J=7.29 Hz, 1H), 6.89 (m, 2H), 7.28 (m, 5H). MS (DCI) m/z 296.12 (M+H)$^+$.

Example 23D

1-Benzyl-1,2,3,4-tetrahydroquinoline-2-carboxamide

Ammonia in methanol (7N, 40 mL) was added to Example 23C (3.10 g, 10.5 mmol) in a stainless steel autoclave and the mixture was chilled to −75° C. Anhydrous ammonia (20 mL) was added, the reactor was sealed, and the mixture was heated to 100° C. for 40 hours. The mixture was concentrated under reduced pressure and the residue was chromatographed on silica gel eluting with 50-100% ethyl acetate in hexane to afford the title compound. $^1$H NMR (300 MHz, DMSO-$d_6$) δ ppm 1.94 (m, 1H), 2.22 (m, 1H), 2.63 (m, 2H), 3.97 (dd, J=5.09, 3.05 Hz, 1H), 4.22 (d, J=17.63 Hz, 1H), 4.75 (d, J=17.29 Hz, 1H), 6.41 (d, J=8.14 Hz, 1H), 6.48 (t, J=7.29 Hz, 1H), 6.88 (m, 2H), 7.13 (s, 1H), 7.22 (m, 3H), 7.31 (m, 3H). MS (DCI) m/z 267.10 (M+H)$^+$.

Example 23E (1-Benzyl-1,2,3,4-tetrahydroquinolin-2-yl)methanamine

Lithium aluminum hydride (1.0M in THF, 18.8 mL, 18.8 mmol) was added to Example 23D (1.67 g, 6.26 mmol) suspended in tetrahydrofuran (50 mL). The mixture stirred for 2 hours at ambient temperature and was refluxed for 1 hour. The mixture was chilled to 0° C. followed by the sequential addition of water (1.6 mL), tetrahydrofuran (50 mL), 15% sodium hydroxide (1.6 mL) and water (3.2 mL). The mixture was filtered, the solids were rinsed with ethyl acetate (200 mL), and the combined filtrate was dried over sodium sulfate, filtered, and concentrated under reduced pressure to afford the title compound. $^1$H NMR (300 MHz, CDCl$_3$) δ ppm 1.95 (m, 1H), 2.11 (m, 1H), 2.82 (m, 4H), 3.36 (td, J=8.39, 4.58 Hz, 1H), 4.59 (d, J=6.44 Hz, 2H), 6.48 (d, J=7.46 Hz, 1H), 6.59 (t, J=7.46 Hz, 1H), 6.99 (m, 2H), 7.23 (m, 2H), 7.30 (m, 2H). MS (DCI) m/z 253.12 (M+H)$^+$.

Example 23F

N-[1-Benzyl-1,2,3,4-tetrahydroquinolin-2-yl)methyl]-N'-(7-hydroxy-5,6,7,8-tetrahydronaphthalen-1-yl)urea To di(N-succinimidyl) carbonate (539 mg, 2.1 mmol) in acetonitrile (5 mL) was added Example 1G (556 mg, 2.0 mmol) in acetonitrile (5 mL) and pyridine (0.17 mL, 2.1 mmol) and the mixture stirred for 15 minutes at ambient temperature. Example 23E (505 mg, 2.0 mmol) in acetonitrile (10 mL) and diisopropylethylamine (1.05 mL, 6.0 mmol) were added and the mixture stirred for 30 minutes. The mixture was concentrated under reduced pressure and the residue was chromatographed on silica gel eluting with 0-30% ethyl acetate in hexane to afford 1-((1-benzyl-1,2,3,4-tetrahydroquinolin-2-yl)methyl)-3-(7-(tert-butyldimethylsilyloxy)-5,6,7,8-tetrahydronaphthalen-1-yl)urea. The intermediate was dissolved in tetrahydrofuran (20 mL), and tetrabutylammonium fluoride (1.0M in THF, 3.2 mL, 3.2 mmol) was added and the mixture stirred overnight at ambient temperature. The mixture was concentrated under reduced pressure and the residue was chromatographed on silica gel eluting with 0-10% methanol in ethyl acetate. The residue was dissolved in ethyl acetate (300 mL), washed with water (300 mL), brine, dried over sodium sulfate, filtered, concentrate under reduced pressure, and vacuum dried overnight to afford the title compound. $^1$H NMR (300 MHz, DMSO-d$_6$) δ ppm 1.58 (m, 1H), 1.84 (m, 2H), 2.03 (m, 1H), 2.33 (dd, J=16.78, 7.63 Hz, 1H), 2.78 (m, 5H), 3.12 (m, 1H), 3.49 (m, 1H), 3.91 (m, 1H), 4.62 (q, J=15.85 Hz, 2H), 4.85 (d, J=4.41 Hz, 1H), 6.33 (d, J=8.13 Hz, 1H), 6.46 (td, J=7.29, 0.91 Hz, 1H), 6.72 (m, 2H), 6.84 (t, J=7.80 Hz, 1H), 6.94 (dd, J=7.12, 1.02 Hz, 1H), 6.97 (t, J=7.80 Hz, 1H), 7.22 (m, 3H), 7.31 (m, 2H), 7.56 (m, 2H). MS (ESI) m/z 442.28 (M+H)$^+$. Calcd for C$_{28}$H$_{31}$N$_3$O$_2$.0.39 EtOAc: C, 74.60; H, 7.23; N, 8.83. Found: C, 74.58; H, 7.41; N, 8.94.

Example 24

N-{[1-Benzyl-7-(trifluoromethyl)-1,2,3,4-tetrahydroquinolin-2-yl]methyl}-N'-(7-hydroxy-5,6,7,8-tetrahydronaphthalen-1-yl)urea

Example 24A

Dimethyl 2-(3-(trifluoromethyl)phenylamino)maleate 3-(Trifluoromethyl)aniline (10.0 g, 62.0 mmol) and dimethyl acetylenedicarboxylate (8.4 mL, 68.4 mmol) were dissolved in methanol (100 mL) and the mixture was refluxed for 2 hours. After cooling, the mixture was concentrated under reduced pressure and the residue was chromatographed on silica gel eluting with 0-30% ethyl acetate in hexane to afford the title compound. $^1$H NMR (300 MHz, CD$_3$OD) δ ppm 3.71 (s, 3H), 3.73 (s, 3H), 5.49 (s, 1H), 7.16 (m, 2H), 7.36 (d, J=7.80 Hz, 1H), 7.48 (t, J=7.80 Hz, 1H). MS (ESI) m/z 303.97 (M+H)$^+$.

Example 24B

Methyl 4-oxo-7-(trifluoromethyl)-1,4-dihydroquinoline-2-carboxylate and Methyl 4-oxo-5-(trifluoromethyl)-1,4-dihydroquinoline-2-carboxylate Example 24A (14.42 g, 47.6 mmol) in diphenyl ether (20 mL) was added in 2 mL portions to diphenyl ether (150 mL) that was preheated to 245° C. The mixture was heated for 1 hour at 250° C. then cooled to ambient temperature. Hexane (200 mL) was added to the mixture, the solids were collected by filtration, rinsed with hexane (200 mL) and diethyl ether (100 mL), and air-dried to afford the title compound as a mixture of regioisomers: ~85% methyl 4-oxo-7-(trifluoromethyl)-1,4-dihydroquinoline-2-carboxylate and ~15% methyl 4-oxo-5-(trifluoromethyl)-1,4-dihydroquinoline-2-carboxylate. $^1$H NMR (300 MHz, CD$_3$OD) δ ppm 4.05 (s, 3H), 7.00 (s, 1H), 7.67 (dd, J=8.82, 1.70 Hz, 1H), 8.21 (s, 1H), 8.41 (d, J=8.48 Hz, 1H). MS (ESI) m/z 271.91 (M+H)$^+$.

Example 24C

Methyl 4-chloro-7-(trifluoromethyl)quinoline-2-carboxylate

Example 24B (9.53 g, 35.1 mmol) and phosphorus oxychloride (100 mL, 1.07 mol) were refluxed for 2 hours. After cooling, the mixture was poured onto ice (1.0 L) and stirred for 1 hour. The mixture was extracted twice with ethyl acetate (400 mL), washed with brine, dried over sodium sulfate, filtered, and concentrate under reduced pressure. The residue was chromatographed on silica gel eluting with 0-40% ethyl acetate in hexane to afford the title compound. $^1$H NMR (300 MHz, DMSO-d$_6$) δ ppm 3.99 (s, 3H), 8.19 (dd, J=8.65, 1.86 Hz, 1H), 8.41 (s, 1H), 8.52 (d, J=8.82 Hz, 1H), 8.66 (s, 1H). MS (ESI) m/z 289.94 (M+H)$^+$.

Example 24D

Methyl 7-(trifluoromethyl)-1,2,3,4-tetrahydroquinoline-2-carboxylate

Example 24C (8.21 g, 28.3 mmol) in tetrahydrofuran (85 mL) was added to a mixture of 5% palladium on carbon (1.7 g) and methanol (85 mL) in a Parr shaker. The glass reactor was sealed and flushed with nitrogen and pressurized with hydrogen (60 psi). The mixture was shaken at 50° C. for 16 hours. The solids were filtered, rinsed with methanol, and the filtrate was concentrated under reduced pressure. Ethyl acetate (200 mL) was added, and the separated organic layer was washed with saturated sodium bicarbonate (200 mL) and brine. The organic layer was dried over sodium sulfate, filtered, and concentrate under reduced pressure. The residue was chromatographed on silica gel eluting with 0-30% ethyl acetate in hexane to afford the title compound. $^1$H NMR (300 MHz, DMSO-d$_6$) δ ppm 2.01 (m, 2H), 2.61 (m, 1H), 2.73 (dt, J=16.95, 5.42 Hz, 1H), 3.67 (s, 3H), 4.14 (td, J=5.08, 2.71 Hz, 1H), 6.53 (d, J=2.38 Hz, 1H), 6.73 (dd, J=7.80, 1.36 Hz, 1H), 6.88 (d, J=1.69 Hz, 1H), 7.04 (d, J=7.80 Hz, 1H). MS (ESI) m/z 259.90 (M+H)$^+$.

Example 24E

Methyl 1-benzyl-7-(trifluoromethyl)-1,2,3,4-tetrahydroquinoline-2-carboxylate

Example 24D (1.30 g, 5.0 mmol), benzyl bromide (0.6 mL, 5.0 mmol) and diisopropylethylamine (1.74 mL, 10.0 mmol) in acetonitrile (8 mL) were heated in a microwave at 150° C. for 1 hour. Ethyl acetate (200 mL) was added and the separated organic layer was washed twice with water (200 mL) and brine. The organic layer was dried over sodium sulfate, filtered, and concentrate under reduced pressure. The residue was chromatographed on silica gel eluting with 0-20% ethyl acetate in hexane to afford the title compound. $^1$H NMR (300 MHz, CDCl$_3$) δ ppm 2.14 (m, 1H), 2.39 (dq, J=13.35, 3.69 Hz, 1H), 2.77 (dd, J=8.99, 3.56 Hz, 2H), 3.72 (s, 3H), 4.18 (dd, J=5.26, 2.88 Hz, 1H), 4.32 (d, J=16.95 Hz, 1H), 4.79 (d, J=16.95 Hz, 1H), 6.78 (s, 1H), 6.86 (d, J=7.80 Hz, 1H), 7.05 (d, J=7.80 Hz, 1H), 7.24 (m, 2H), 7.31 (m, 3H). MS (DCI) m/z 350.12 (M+H)$^+$.

Example 24F

1-Benzyl-7-(trifluoromethyl)-1,2,3,4-tetrahydroquinoline-2-carboxamide

Ammonia in methanol (7N, 20 mL) was added to Example 24E (1.56 g, 4.46 mmol) in a stainless steel autoclave, chilled to −75° C. followed by the addition of anhydrous ammonia (5 mL). The reactor was sealed and heated at 100° C. for 56 hours. The mixture was concentrated under reduced pressure and the residue was chromatographed on silica gel eluting with 50-100% ethyl acetate in hexane to afford the title compound. $^1$H NMR (300 MHz, CDCl$_3$) δ ppm 1.93 (m, 1H), 2.47 (m, 1H), 2.79 (m, 2H), 4.06 (dd, J=5.94, 2.55 Hz, 1H), 4.40 (d, J=16.96 Hz, 1H), 4.86 (d, J=16.61 Hz, 1H), 5.47 (br s, 1H), 6.16 (br s, 1H), 6.93 (m, 2H), 7.13 (d, J=7.12 Hz, 1H), 7.21 (m, 2H), 7.31 (m, 3H). MS (DCI) m/z 335.10 (M+H)$^+$.

Example 24G (1-Benzyl-7-(trifluoromethyl)-1,2,3,4-tetrahydroquinolin-2-yl)methanamine Lithium aluminum hydride (1.0M in THF, 9.7 mL, 9.7 mmol) was added to Example 24F (1.08 g, 3.24 mmol) in tetrahydrofuran (30 mL). The mixture stirred for 2 hours at ambient temperature then refluxed for 1 hour. After cooling to 0° C., was added sequentially water (0.8 mL), tetrahydrofuran (25 mL), 15% sodium hydroxide (0.8 mL) and water (1.6 mL). The mixture was filtered, the solids were washed with ethyl acetate (200 mL), and the organic layer was dried over sodium sulfate, filtered, and concentrated under reduced pressure to afford the title compound. $^1$H NMR (300 MHz, CDCl$_3$) δ ppm 1.92 (tt, J=12.76, 5.21 Hz, 1H), 2.14 (m, 1H), 2.81 (m, 4H), 3.40 (td, J=8.31, 4.75 Hz, 1H), 4.62 (q, J=15.60 Hz, 2H), 6.69 (s, 1H), 6.81 (d, J=7.80 Hz, 1H), 7.07 (d, J=7.12 Hz, 1H), 7.24 (m, 2H), 7.29 (m, 2H). MS (DCI) m/z 321.08 (M+H)$^+$.

Example 24H 1-((1-Benzyl-7-(trifluoromethyl)-1,2,3,4-tetrahydroquinolin-2-yl)methyl)-3-(7-(tert-butyldimethylsilyloxy)-5,6,7,8-tetrahydronaphthalen-1-yl)urea To di(N-succinimidyl) carbonate (870 mg, 3.40 mmol) in acetonitrile (5 mL) was added Example 1G (898 mg, 3.24 mmol) in acetonitrile (10 mL) and pyridine (0.28 mL, 3.40 mmol) and the mixture was stirred for 15 minutes at ambient temperature. Example 24G (1.09 g) dissolved in acetonitrile (15 mL) and diisopropylethylamine (1.7 mL, 9.7 mmol) were added and the mixture stirred for 30 minutes. The mixture was concentrated under reduced pressure and the residue was chromatographed on silica gel eluting with 0-30% ethyl acetate in hexane to afford the title compound. $^1$H NMR (300 MHz, DMSO-d$_6$) δ ppm 0.08 (q, J=3.05 Hz, 6H), 0.86 (s, 9H), 1.64 (m, 1H), 1.82 (m, 2H), 2.05 (m, 1H), 2.40 (dd, J=16.95, 7.46 Hz, 1H), 2.77 (m, 4H), 2.94 (m, 1H), 3.57 (m, 1H), 4.10 (m, 1H), 4.67 (q, J=15.60 Hz, 2H), 6.52 (s, 1H), 6.68 (m, 1H), 6.74 (d, J=7.46 Hz, 2H), 6.98 (t, J=7.80 Hz, 1H), 7.14 (d, J=7.80 Hz, 1H), 7.23 (m, 3H), 7.29 (m, 2H), 7.46 (dd, J=7.12, 5.76 Hz, 1H), 7.58 (s, 1H). MS (ESI) m/z 624.46 (M+H)$^+$.

Example 24I

N-{[1-Benzyl-7-(trifluoromethyl)-1,2,3,4-tetrahydroquinolin-2-yl]methyl}-N'-(7-hydroxy-5,6,7,8-tetrahydronaphthalen-1-yl)urea Example 24H (831 mg, 1.33 mmol) was dissolved in tetrahydrofuran (20 mL), and tetrabutylammonium fluoride (1.0M in THF, 2.7 mL, 2.7 mmol) was added, and the mixture stirred overnight at ambient temperature. The mixture was concentrated under reduced pressure and the residue was chromatographed on silica gel eluting with 0-10% methanol in ethyl acetate. The residue was dissolved in ethyl acetate (200 mL), and the organic layer was washed with water (200 mL), brine, dried over sodium sulfate, filtered, concentrate under reduced pressure, and vacuum dried overnight to afford the title compound. $^1$H NMR (300 MHz, DMSO-d$_6$) δ ppm 1.58 (m, 1H), 1.85 (m, 2H), 2.06 (m, 1H), 2.34 (dd, J=16.62, 7.80 Hz, 1H), 2.78 (m, 4H), 2.94 (m, 1H), 3.16 (m, 1H), 3.56 (m, 1H), 3.91 (m, 1H), 4.69 (q, J=15.71 Hz, 2H), 4.85 (d, J=4.07 Hz, 1H), 6.53 (s, 1H), 6.75 (m, 3H), 6.97 (t, J=7.80 Hz, 1H), 7.15 (d, J=7.80 Hz, 1H), 7.23 (m, 3H), 7.32 (m, 2H), 7.58 (m, 2H). MS (ESI) m/z 510.33 (M+H)$^+$. Calcd for C$_{29}$H$_{30}$F$_3$N$_3$O$_2$.0.37 EtOAc: C, 67.52; H, 6.13; N, 7.75. Found: C, 67.45; H, 6.21; N, 7.91.

Example 25

N-(7-Hydroxy-5,6,7,8-tetrahydronaphthalen-1-yl)-N'-{[1-methyl-7-(trifluoromethyl)-1,2,3,4-tetrahydroquinolin-2-yl]methyl}urea

Example 25A

Methyl 1-methyl-7-(trifluoromethyl)-1,2,3,4-tetrahydroquinoline-2-carboxylate

Example 24D (1.31 g, 5.0 mmol), iodomethane (0.33 mL, 5.25 mmol) and potassium carbonate (691 mg, 5.0 mmol) in dimethylformamide (8 mL) were heated in a microwave at 120° C. for 1 hour. Ethyl acetate (200 mL) was added and the separated organic layer was washed with saturated sodium bicarbonate (200 mL), brine, dried over sodium sulfate, filtered and concentrated under reduced pressure to afford the title compound. $^1$H NMR (300 MHz, CDCl$_3$) δ ppm 2.11 (m, 1H), 2.31 (m, 1H), 2.72 (m, 2H), 2.99 (s, 3H), 3.72 (s, 3H), 4.08 (dd, J=5.76, 3.39 Hz, 1H), 6.79 (s, 1H), 6.86 (d, J=7.80 Hz, 1H), 7.01 (d, J=7.80 Hz, 1H). MS (DCI) m/z 274.05 (M+H)$^+$.

Example 25B

1-Methyl-7-(trifluoromethyl)-1,2,3,4-tetrahydroquinoline-2-carboxamide

Ammonia in methanol (7M, 15 mL) was added to Example 25A (1.15 g, 4.22 mmol) in a stainless steel autoclave and the mixture was cooled to −75° C. Anhydrous ammonia (10 mL) was added and the reactor was sealed and heated at 100° C. for 48 hours. The mixture was concentrated under reduced pressure and the residue was chromatographed on silica gel eluting with 50-100% ethyl acetate in hexane to afford the title compound. $^1$H NMR (300 MHz, CDCl$_3$) δ ppm 1.90 (m, 1H), 2.40 (dq, J=13.23, 3.73 Hz, 1H), 2.73 (m, 2H), 3.06 (s, 3H), 3.89 (dd, J=6.10, 3.05 Hz, 1H), 5.49 (br s, 1H), 6.13 (br s, 1H), 6.88 (s, 1H), 6.95 (d, J=7.80 Hz, 1H), 7.09 (d, J=7.80 Hz, 1H). MS (DCI) m/z 259.07 (M+H)$^+$.

Example 25C (1-Methyl-7-(trifluoromethyl)-1,2,3,4-tetrahydroquinolin-2-yl)methanamine Lithium aluminum hydride (1.0M in THF, 8.1 mL, 8.1 mmol) was added to Example 25B (697 mg, 2.7 mmol) suspended in tetrahydrofuran (20 mL). The mixture stirred for 1 hour at ambient temperature then refluxed for 1 hour. The mixture was cooled to 0° C. followed by the sequential addition of water (0.7 mL), tetrahydrofuran (20 mL), 15% sodium hydroxide (0.7 mL) and water (1.4 mL). The mixture was filtered, the solids were rinsed with ethyl acetate (200 mL) and the filtrate was dried over sodium sulfate, filtered, and concentrated under reduced pressure to afford the title compound. $^1$H NMR (300 MHz, CDCl$_3$) δ ppm 1.85 (m, 1H), 2.06 (m, 1H), 2.74 (m, 3H), 2.91 (dd, J=13.05, 4.92 Hz, 1H), 3.03

(s, 3H), 3.28 (m, 1H), 6.72 (s, 1H), 6.82 (d, J=7.46 Hz, 1H), 7.02 (d, J=7.80 Hz, 1H). MS (DCI) m/z 245.06 (M+H)$^+$.

Example 25D

N-(7-Hydroxy-5,6,7,8-tetrahydronaphthalen-1-yl)-N'-{[1-methyl-7-(trifluoromethyl)-1,2,3,4-tetrahydroquinolin-2-yl]methyl}urea To di(N-succinimidyl) carbonate (417 mg, 1.63 mmol) in acetonitrile (5 mL) was added Example 1G (430 mg, 1.55 mmol) in acetonitrile (5 mL) and pyridine (0.13 mL, 1.63 mmol) and the mixture stirred for 15 minutes at ambient temperature. Example 25C (379 mg, 1.55 mmol) dissolved in acetonitrile (10 mL) and diisopropylethylamine (0.81 mL, 4.65 mmol) were added and the mixture stirred for 30 minutes. The mixture was concentrated under reduced pressure and the residue was chromatographed on silica gel eluting with 0-35% ethyl acetate in hexane, to afford 1-(7-(tert-butyldimethylsilyloxy)-5,6,7,8-tetrahydronaphthalen-1-yl)-3-((1-methyl-7-(trifluoromethyl)-1,2,3,4-tetrahydroquinolin-2-yl)methyl)urea. The intermediate was dissolved in tetrahydrofuran (20 mL), tetrabutylammonium fluoride (1.0M in THF, 2.5 mL, 2.5 mmol) was added, and the mixture stirred overnight at ambient temperature. The mixture was concentrated under reduced pressure and the residue was chromatographed on silica gel eluting with 0-10% methanol in ethyl acetate. The solid was suspended in methanol (5 mL), sonicated, and water (150 mL) was added. The sonication was repeated, the solids were collected by filtration and rinsed with water, and freeze-dried to provide the title compound. $^1$H NMR (300 MHz, DMSO-d$_6$) δ ppm 1.58 (m, 1H), 1.70 (m, 1H), 1.86 (m, 1H), 1.96 (m, 1H), 2.33 (dd, J=16.61, 7.80 Hz, 1H), 2.78 (m, 5H), 3.00 (s, 3H), 3.06 (m, 1H), 3.41 (m, 1H), 3.91 (m, 1H), 4.86 (d, J=4.07 Hz, 1H), 6.70 (m, 3H), 6.80 (d, J=7.46 Hz, 1H), 6.98 (t, J=7.80 Hz, 1H), 7.11 (d, J=7.80 Hz, 1H), 7.56 (s, 1H), 7.61 (d, J=8.14 Hz, 1H). MS (ESI) m/z 434.22 (M+H)$^1$. Calcd for C$_{23}$H$_{26}$F$_3$N$_3$O$_2$: C, 63.73; H, 6.05; N, 9.69. Found: C, 63.66; H, 5.97; N, 9.54.

Example 26

N-(7-Hydroxy-5,6,7,8-tetrahydronaphthalen-1-yl)-N'-{[7-(trifluoromethyl)-1,2,3,4-tetrahydroquinolin-2-yl]methyl}urea

Example 26A 1-(7-(tert-Butyldimethylsilyloxy)-5,6,7,8-tetrahydronaphthalen-1-yl)-3-(trifluoromethyl)-1,2,3,4-tetrahydroquinolin-2-yl)methyl)urea Example 24H (780 mg, 1.25 mmol) was added to a mixture of ethanol (40 mL) and 20% palladium hydroxide on carbon (190 mg) in a Parr shaker. The glass reactor was sealed and flushed with nitrogen, and pressurized with hydrogen (60 psi). The mixture was shaken at ambient temperature for 18 hours, filtered and concentrated under reduced pressure the filtrate to provide the title compound. $^1$H NMR (300 MHz, DMSO-d$_6$) δ ppm 0.08 (m, 6H), 0.86 (s, 9H), 1.61 (m, 2H), 1.84 (m, 2H), 2.39 (dd, J=16.95, 7.46 Hz, 1H), 2.75 (m, 5H), 3.08 (m, 1H), 4.11 (m, 1H), 6.21 (s, 1H), 6.71 (m, 4H), 6.98 (m, 2H), 7.57 (m, 2H). MS (ESI) m/z 534.41 (M+H)$^+$.

Example 26B

N-(7-Hydroxy-5,6,7,8-tetrahydronaphthalen-1-yl)-N'-{[7-(trifluoromethyl)-1,2,3,4-tetrahydroquinolin-2-yl]methyl}urea To Example 26A (650 mg, 1.22 mmol) in tetrahydrofuran (20 mL) was added tetrabutylammonium fluoride (1.0M in THF, 2.44 mL, 2.44 mmol) and the mixture stirred overnight at ambient temperature. The mixture was concentrated under reduced pressure and chromatographed on silica gel eluting with 0-to-10% methanol in ethyl acetate to afford a white solid. The residue was dissolved in methanol (10 mL) and water (150 mL). The mixture was sonicated and filtered. The solid was freeze-dried overnight to obtain the title compound. $^1$H NMR (300 MHz, DMSO-d$_6$) δ ppm 1.59 (m, 2H), 1.86 (m, 2H), 2.33 (dd, J=16.45, 7.63 Hz, 1H), 2.76 (m, 5H), 3.08 (m, 1H), 3.36 (m, 2H), 3.91 (m, 1H), 4.85 (dd, J=4.24, 2.20 Hz, 1H), 6.23 (s, 1H), 6.70 (d, J=7.80 Hz, 2H), 6.78 (m, 2H), 6.98 (t, J=7.80 Hz, 1H), 7.04 (d, J=7.80 Hz, 1H), 7.59 (s, 1H), 7.65 (d, J=7.80 Hz, 1H). MS (ESI) m/z 420.20 (M+H)$^+$. Calcd for C$_{22}$H$_{24}$F$_3$N$_3$O$_2$.0.06H$_2$O: C, 62.84; H, 5.78; N, 9.99. Found: C, 62.85; H, 5.73; N, 9.93.

Example 27

N-(7-Hydroxy-5,6,7,8-tetrahydronaphthalen-1-yl)-N'-[(1-methyl-1,2,3,4-tetrahydroquinolin-2-yl)methyl]-urea

Example 27A

Ethyl 1-methyl-1,2,3,4-tetrahydroquinoline-2-carboxylate

Example 23B (2.46 g, 12.0 mmol), iodomethane (1.12 mL, 18.0 mmol) and potassium carbonate (1.66 g, 12.0 mmol) in dimethylformamide (12 mL) were stirred overnight at ambient temperature. To the mixture was added ethyl acetate (200 mL). The separated organic solution was washed with water (2×200 mL), brine (1×), dried over sodium sulfate, filtered and concentrate under reduced pressure. The residue was chromatographed on silica gel eluting with 0-to-20% ethyl acetate in hexane to provide the title compound. Obtained 2.21 g (84% yield) of Example 27A as a colorless liquid. $^1$H NMR (300 MHz, CDCl$_3$) δ ppm 1.24 (t, J=7.12 Hz, 3H), 2.12 (m, 1H), 2.29 (dq, J=13.18, 4.31 Hz, 1H), 2.68 (d, J=4.41 Hz, 1H), 2.71 (m, 1H), 2.95 (s, 3H), 4.01 (dd, J=5.08, 3.73 Hz, 1H), 4.17 (dq, J=8.14, 7.12 Hz, 2H), 6.63 (m, 2H), 6.94 (d, J=7.46 Hz, 1H), 7.10 (t, J=7.80 Hz, 1H). MS (DCI) m/z 220.10 (M+H)$^1$.

Example 27B

1-Methyl-1,2,3,4-tetrahydroquinoline-2-carboxamide

Added 7N ammonia in methanol (40 mL) to Example 27A (2.10 g, 9.59 mmol) in a stainless steel autoclave chilled to −75° C. followed by the addition of anhydrous ammonia (20 mL). The reactor was sealed and heated at 100° C. for 48 hours. The mixture was concentrated under reduced pressure to a brown solid which was chromatographed on silica gel eluting with 50-to-100% ethyl acetate in hexane to provide the title compound. $^1$H NMR (300 MHz, DMSO-d$_6$) δ ppm 1.82 (m, 1H), 2.10 (m, 1H), 2.56 (m, 1H), 2.84 (s, 3H), 3.79 (dd, J=5.42, 3.73 Hz, 1H), 6.51 (td, J=7.29, 1.02 Hz, 1H), 6.57

(d, J=8.14 Hz, 1H), 6.87 (dd, J=7.12, 1.36 Hz, 1H), 7.01 (t, J=7.80 Hz, 1H), 7.08 (s, 1H), 7.23 (s, 1H). MS (DCI) m/z 191.09 (M+H)$^+$.

Example 27C (1-Methyl-1,2,3,4-tetrahydroquinolin-2-yl)methanamine

Lithium aluminum hydride (1.0M in THF, 18.9 mL, 18.9 mmol) was added to Example 27B (1.20 g, 6.3 mmol) in tetrahydrofuran (30 mL). The mixture was stirred for 1.5 hours at ambient temperature then refluxed for 1 hour. The mixture was chilled to 0° C., followed by the sequential addition of water (1.6 mL), tetrahydrofuran (50 mL), 15% sodium hydroxide (1.6 mL) and water (3.2 mL). The mixture was filtered and the solids were rinsed with ethyl acetate (200 mL). The combined organic solution was dried with sodium sulfate and concentrated under reduced pressure to provide the title compound. $^1$H NMR (300 MHz, CDCl$_3$) δ ppm 1.87 (m, 1H), 2.03 (m, 1H), 2.72 (m, 3H), 2.89 (dd, J=12.88, 4.74 Hz, 1H), 2.99 (s, 3H), 3.23 (m, 1H), 6.57 (d, J=8.14 Hz, 1H), 6.59 (t, J=7.12 Hz, 1H), 6.96 (d, J=7.12 Hz, 1H), 7.09 (t, J=7.80 Hz, 1H). MS (DCI) m/z 177.10 (M+H)$^+$.

Example 27D

N-(7-Hydroxy-5,6,7,8-tetrahydronaphthalen-1-yl)-N'-[(1-methyl-1,2,3,4-tetrahydroquinolin-2-yl)methyl]-urea To di(N-succinimidyl) carbonate (538 mg, 2.1 mmol) in acetonitrile (5 mL) was added Example 1G (555 mg, 2.0 mmol) in acetonitrile (5 mL) and pyridine (0.17 mL, 2.1 mmol) and the mixture was stirred for 15 minutes at ambient temperature. Example 27C (353 mg, 2.0 mmol) in acetonitrile (10 mL) and diisopropylethylamine (1.05 mL, 6.0 mmol) were added and the mixture was stirred for 30 minutes. The mixture was concentrated under reduced pressure and chromatographed on silica gel eluting with 0-to-40% ethyl acetate in hexane to provide 780 mg of 1-(7-(tert-butyldimethylsilyloxy)-5,6,7,8-tetrahydronaphthalen-1-yl)-3-((1-methyl-1,2,3,4-tetrahydroquinolin-2-yl)methyl)urea as a white foam. The intermediate was dissolved in tetrahydrofuran (20 mL) followed by the addition of tetrabutylammonium fluoride (1.0M in THF, 3.25 mL, 3.25 mmol) and the mixture was stirred overnight at ambient temperature. The mixture was concentrated under reduced pressure and chromatographed on silica gel eluting with 0-to-10% methanol in ethyl acetate to afford a white solid. The residue was suspended in methanol (15 mL), sonicated followed by the addition of water (250 mL), repeated sonication, the solids were collected by filtration, rinsed with water, and freeze-dried the wet cake overnight to provide the title compound. $^1$H NMR (300 MHz, DMSO-d$_6$) δ ppm 1.58 (m, 1H), 1.71 (m, 1H), 1.90 (m, 2H), 2.33 (dd, J=16.28, 8.14 Hz, 1H), 2.60 (m, 1H), 2.78 (m, 4H), 2.94 (s, 3H), 3.03 (m, 1H), 3.92 (br s, 1H), 4.86 (d, J=4.07 Hz, 1H), 6.50 (m, 2H), 6.71 (m, 2H), 6.91 (d, J=7.12 Hz, 1H), 6.98 (m, 2H), 7.55 (s, 1H), 7.63 (d, J=8.14 Hz, 1H). MS (ESI) m/z 366.20 (M+H)$^+$. Calcd for C$_{22}$H$_{27}$N$_3$O$_2$: C, 72.30; H, 7.45; N, 11.50. Found: C, 72.37; H, 7.50; N, 11.46.

Example 28

N-(7-hydroxy-5,6,7,8-tetrahydronaphthalen-1-yl)-N'-{(3R)-3-[4-(trifluoromethyl)phenyl]cyclohexyl}urea Example 28A (R)-3-(4-(trifluoromethyl)phenyl)cyclohexanone To a 40 ml microwave flask containing dioxane/H$_2$O (10/1) (22 mL) was added cyclohexen-1-one (1.35 g, 14.0 mmol), acetylacetonatobis(ethylene)rhodium(I) (0.36 g, 1.40 mmol), R-2,2'-bis(diphenyl-phosphino)-1,1'-binaphthyl (0.88 g, 1.40 mmol) and 4-(trifluoromethyl)-phenylboronic acid (5.0 g, 28.0 mmol). The mixture was heated in the microwave (Personal Chemistry) at 100° C. for 20 minutes. The material was transferred to a separatory funnel and extracted with ethyl acetate (150 mL). The resulting organic layer was washed with NaHCO$_3$ (75 mL), dried (Na$_2$SO$_4$), filtered and concentrated under reduced pressure. The mixture was purified on SiO$_2$ (hexane/ethyl acetate 4/1) to provide the title compound. [α]$_D$=+13.62 c=1.0 (CH$_3$OH). $^1$H NMR (CD$_3$OD, 300 MHz); δ 1.72-2.20 (m, 5H), 2.35-2.73 (m, 3H), 3.06-3.15 (m, 1H), 7.40-7.42 (m, 2H), 7.46-7.63 (m, 2H). MS (+ESI)m/z 242 (M+NH$_4$—H$_2$O)$^+$.

Example 28B (R)-3-(4-(trifluoromethyl)phenyl)cyclohexanone O-methyl oxime

To a flask containing Example 28A (1.97 g, 8.60 mmol) was added pyridine (10 mL) followed by N-methoxyamine hydrochloride (0.81 g, 9.60 mmol) and the mixture was stirred at room temperature overnight. The mixture was concentrated under reduced pressure, taken up in ethyl acetate, washed with sat NaHCO$_3$, dried (Na$_2$SO$_4$), filtered and concentrated under reduced pressure. The residue was purified on SiO$_2$ (hexane/ethyl acetate 4/1) to provide the title compound. $^1$H NMR (CD$_3$OD, 300 MHz); δ 1.48-1.89 (m, 2H), 1.92-2.52 (m, 5H), 2.75-2.87 (m, 1H), 3.22-3.35 (m, 1H), 3.79 (d, J=1.70 Hz, 3H), 7.46 (d, J=8.14 Hz, 2H), 7.60 (d, J=8.48 Hz, 2H). MS (DCI) m/z 272 (M+H)$^+$.

Example 28C (3R)-3-(4-(trifluoromethyl)phenyl)cyclohexanamine

To a flask containing Example 28B (1.80 g, 6.90 mmol) was added saturated NH$_3$/CH$_3$OH (50 mL), RaNi (20%, 5.0 eq by weight) and subjected to an atmosphere of hydrogen gas (60 psi). The mixture was stirred at room temperature for 3 hours, filtered and washed with 50 mL of methanol. The solution was concentrated under reduced pressure and the residue was purified on SiO$_2$ (hexane/ethyl acetate 1/1) to afford the title compound. $^1$H NMR (CD$_3$OD, 300 MHz); δ 1.45-1.86 (m, 3H), 1.95-2.55 (m, 5H), 2.80-2.88 (m, 1H), 3.20-3.35 (m, 1H), 7.45 (d, J=8.1 Hz, 2H), 7.60 (d, J=8.4 Hz, 2H). MS (DCI) m/z 244 (M+H)$^+$.

Example 28D 1-(7-(tert-butyl dimethylsilyloxy)-5,6,7,8-tetrahydronaphthalen-1-yl)-3-((3R)-3-(4-(trifluoromethyl)phenyl)cyclohexyl)urea In a 250 mL round bottom flask containing acetonitrile (20 mL) was added Example 1G (0.80 g, 2.90 mmol) followed by di(succinimidyl)carbonate (0.24 g, 3.0 mmol) (Fluka) and pyridine (0.25 mL). The mixture was stirred at room temperature for 30 minutes. Example 28C (0.70 g, 2.90 mmol) was added as a solution in acetonitrile (10 mL) and disopropylethylamine (1.60 mL, 9.10 mmol) to the mixture and allowed to stir at room temperature overnight. The mixture was concentrated under reduced pressure. The material was purified on $SiO_2$ (hexane/ethyl acetate 4/1 tot/1) to provide the title compound. $^1H$ NMR (DMSO, 300 MHz); δ 0.86 (s, 9H), 1.18-2.18 (m, 15H), 2.45-2.58 (m, 1H), 2.71-2.98 (m, 4H), 3.65-3.76 (m, 1H), 4.05-4.18 (m, 2H), 6.83-6.88 (m, 1H), 7.01-7.06 (m, 1H), 7.26 (d, J=7.80 Hz, 1H), 7.36-7.43 (m, 2H), 7.55-7.58 (m, 2H). MS (DCI) m/z 547 $(M+H)^+$.

Example 28E 1-(7-hydroxy-5,6,7,8-tetrahydronaphthalen-1-yl)-34 (3R)-3-(4-(trifluoromethyl)phenyl)cyclohexyl)urea To a round bottom flask containing Example 28D (1.56 g, 2.90 mmol) was added THF (30 mL) followed by tetrabutylammoniumfluoride 1M in THF (5.70 mL) and the mixture was stirred at room temperature overnight. The mixture was concentrated under reduced pressure. The material was purified on $SiO_2$ (hexane/ethyl acetate 1/6) to provide the title compound. $^1H$ NMR (DMSO, 300 MHz); δ 1.07-2.07 (m, 10H), 2.27-2.40 (m, 1H), 2.63-2.87 (m, 4H), 3.54-3.64 (m, 0.5H), 3.85-3.97 (m, 0.5H), 4.83-4.90 (m, 1H), 6.57 (d, J=7.12 Hz, 1H), 6.68 (d, J=7.12 Hz, 1H), 6.93-6.99 (m, 1H), 7.41 (s, 1H), 7.47-7.51 (m, 2H), 7.63-7.66 (m, 3H). MS (DCI) m/z 433 $(M+H)^+$. Calc for $C_{24}H_{27}N_2O_2F_3$: C, 71.29; H, 8.03; N, 10.39. Found: C, 71.18; H, 8.07; N, 10.02.

Example 29

N-{(3S)-3-[4-(dimethylamino)phenyl]cyclopentyl}-N'-(7-hydroxy-5,6,7,8-tetrahydronaphthalen-1-yl) urea Example 29A (S)-3-(4-(dimethylamino)phenyl)cyclopentanone The title compound was prepared using the procedure as described in Example 28A, substituting 2-cyclopenten-1-one for cyclohexen-1-one, S-BINAP and 4-(dimethylamino)-phenylboronic acid for 4-(tertbutyl)-phenylboronic acid. The mixture was purified on $SiO_2$ (hexane/ethyl acetate 4/1) to provide the title compound. $[α]_D$=-22.31 c=1.0 $(CH_3OH)$. $^1H$ NMR $(CD_3OD$, 300 MHz); δ 1.85-2.01 (m, 1H), 2.21-2.40 (m, 4H), 2.42-2.50 (m, 1H), 2.88 (s, 6H), 3.29-3.39 (m, 1H), 6.78-6.81 (m, 2H), 7.11-7.21 (m, 2H). MS (DCI) m/z 204 $(M+H)^+$.

Example 29B (S)-3-(4-(dimethylamino)phenyl)cyclopentanone O-methyl oxime

The title compound was prepared using the procedure as described in Example 28B, substituting Example 29A for Example 28A. Purified on $SiO_2$ (hexane/ethyl acetate 1/1) to provide the title compound. $^1H$ NMR $(CD_3OD$, 300 MHz); δ 1.85-2.00 (m, 1H), 2.20-2.45 (m, 4H), 2.48-2.52 (m, 1H), 2.90 (s, 6H), 3.30-3.40 (m, 1H), 3.90 (s, 3H), 6.75-6.80 (m, 2H), 7.10-7.20 (m, 2H). MS (DCI) m/z 219 $(M+H)^+$.

Example 29C 4-((1S)-3-aminocyclopentyl)-N,N-dimethylaniline

The title compound was prepared using the procedure as described in Example 28C, except for substituting Example 29B for Example 28B. Purified on $SiO_2$ (hexane/ethyl acetate 1/4) to provide the title compound. $^1H$ NMR $(CD_3OD$, 300 MHz); δ 1.33-1.65 (m, 2H), 1.68-2.32 (m, 4H), 2.86 (s, 6H), 3.08-3.54 (m, 2H), 6.70-6.84 (m, 2H), 7.05-7.13 (m, 2H). MS (DCI) m/z 205 $(M+H)^+$.

Example 29D 1-(7-(tert-butyldimethylsilyloxy)-5,6,7,8-tetrahydronaphthalen-1-yl)-3-((3S)-3-(4-(dimethylamine) phenyl)cyclopentyl)urea In a 250 mL round bottom flask containing acetonitrile (20 mL) was added Example 1G (0.80 g, 2.90 mmol) followed by di(succinimidyl)carbonate (0.24 g, 3.0 mmol) (Fluka) and pyridine (0.25 mL). The mixture was stirred at room temperature for 30 minutes. Example 29C (0.70 g, 2.90 mmol) was added as a solution in acetonitrile (10 mL) and disopropylethylamine (1.60 mL, 9.10 mmol) to the mixture and allowed to stir at room temperature overnight. The mixture was concentrated under reduced pressure. The material was purified on $SiO_2$ (hexane/ethyl acetate 4/1 tot/1) to provide the title compound. $^1H$ NMR (DMSO, 300 MHz); δ 0.87 (s, 9H), 1.31-1.70 (m, 3H), 1.79-2.10 (m, 4H), 2.26-2.42 (m, 2H), 2.65-3.11 (m, 10H), 3.31 (s, 6H), 3.98-4.16 (m, 2H), 6.65-6.71 (m, 4H), 6.95 (t, J=7.80, 1H), 7.03-7.10 (m, 2H), 7.37 (d, J=7.80 Hz, 1H), 7.54-7.64 (m, 1H). MS (DCI) m/z 508 $(M+H)^+$.

Example 29E 1-((3S)-3-(4-(dimethylamino)phenyl)cyclopentyl)-3-(7-hydroxy-5,6,7,8-tetrahydronaphthalen-1-yl)urea To a round bottom flask containing Example 29D (1.0 g, 2.0 mmol) was added THF (20 mL) followed by tetrabutylammoniumfluoride 1M in THF (4.0 mL) and the mixture was stirred at room temperature overnight. The mixture was concentrated under reduced pressure and the material was purified on $SiO_2$ (ethyl acetate/10% methanol) to provide the title compound. $^1H$ NMR (DMSO, 300 MHz); δ 1.31-1.64 (m, 4H), 1.79-2.36 (m, 7H), 2.61-2.81 (m, 8H), 2.84-3.12 (m, 1H), 3.92-4.07 (m, 1H), 6.66-6.79 (m, 4H), 6.97 (t, J=7.12 Hz, 1H), 7.06-7.10 (m, 2H), 7.36 (d, J=6.80 Hz, 1H), 7.69 (t, J=6.80 Hz, 1H). MS (DCI) m/z 394 $(M+H)^+$. Calc for $C_{24}H_{31}N_3O_2$: C, 71.29; H, 8.03; N, 10.39. Found: C, 71.18; H, 8.07; N, 10.02.

Pharmaceutical Compositions

The application also provides pharmaceutical compositions comprising a therapeutically effective amount of a compound of formula (I) in combination with a pharmaceutically acceptable carrier. The compositions comprise compounds of the application formulated together with one or more non-toxic pharmaceutically acceptable carriers. The pharmaceutical compositions can be formulated for oral administration in solid or liquid form, for parenteral injection or for rectal administration.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The pharmaceutical compositions of this application can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration, including intravenous, intramuscular, intraperitoneal, intrasternal, subcutaneous, intraarticular injection and infusion.

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions can also contain adjuvants such as preservative agents, wetting agents, emulsifying agents, and dispersing agents. Prevention of the action of microorganisms can be ensured by various antibacterial and antifungal agents, for example, parabens, chlorobutanol, phenol, sorbic acid, and the like. It also can be desirable to include isotonic agents, for example, sugars, sodium chloride and the like. Prolonged absorption of the injectable pharmaceutical form can be brought about by the use of agents delaying absorption, for example, aluminum monostearate and gelatin.

In some cases, in order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug can depend upon its rate of dissolution, which, in turn, may depend upon crystal size and crystalline form. Alternatively, a parenterally administered drug form can be administered by dissolving or suspending the drug in an oil vehicle.

Suspensions, in addition to the active compounds, can contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the application can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions can be formulated according to the known art using suitable dispersing or wetting agents and suspending agents. The sterile injectable preparation also can be a sterile injectable solution, suspension or emulsion in a nontoxic, parenterally acceptable diluent or solvent such as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the application is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well-known in the pharmaceutical formulating art. They can optionally contain opacifying agents and can also be of a composition that they release the active ingredient(s) only, or preferentially, in a certain part of the intestinal tract in a delayed manner. Examples of materials useful for delaying release of the active agent can include polymeric substances and waxes.

Compositions for rectal or vaginal administration are preferably suppositories which can be prepared by mixing the compounds of this application with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this application include ointments, pastes, creams, lotions, gels, powders, solutions, sprays, inhalants or patches. A desired compound of the application is admixed under sterile conditions with a pharmaceutically acceptable carrier and any needed preservatives or buffers as may be required. Ophthalmic formulation, eardrops, eye ointments, powders and solutions are also contemplated as being within the scope of this application. The ointments, pastes, creams and gels may contain, in addition to an active compound of this application, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this application, lactose, talc, silicic acid, aluminum hydroxide, calcium silicates and polyamide powder, or mixtures of these substances. Sprays can additionally contain customary propellants such as chlorofluorohydrocarbons.

Compounds of the application also can be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the application, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

Dosage forms for topical administration of a compound of this application include powders, sprays, ointments and inhalants. The active compound is mixed under sterile conditions with a pharmaceutically acceptable carrier and any needed preservatives, buffers or propellants. Ophthalmic formulations, eye ointments, powders and solutions are also contemplated as being within the scope of this application. Aqueous liquid compositions of the application also are particularly useful.

The compounds of the application can be used in the form of pharmaceutically acceptable salts, esters, or amides derived from inorganic or organic acids. The term "pharmaceutically acceptable salts, esters and amides," as used herein, include salts, zwitterions, esters and amides of compounds of formula (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the application or separately by reacting a free base function with a suitable organic acid.

Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid, and citric acid.

Basic addition salts can be prepared in situ during the final isolation and purification of compounds of this application by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylamine, dimethylamine, trimethylamine, triethylamine, diethylamine, ethylamine and the such as. Other representative organic amines useful for the formation of base addition salts include ethylenediamine, ethanolamine, diethanolamine, piperidine, and piperazine.

The term "pharmaceutically acceptable ester," as used herein, refers to esters of compounds of the application which hydrolyze in vivo and include those that break down readily in the human body to leave the parent compound or a salt thereof. Examples of pharmaceutically acceptable, non-toxic esters of the application include $C_1$-to-$C_6$ alkyl esters and $C_5$-to-$C_7$ cycloalkyl esters, although $C_1$-to-$C_4$ alkyl esters are preferred. Esters of the compounds of formula (I) can be prepared according to conventional methods. Pharmaceutically acceptable esters can be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, alkyl trifilate, for example with methyl iodide, benzyl iodide, cyclopentyl iodide. They also can be prepared by reaction of the compound with an acid such as hydrochloric acid and an alkylcarboxylic acid such as acetic acid, or with acid and an arylcarboxylic acid such as benzoic acid.

The term "pharmaceutically acceptable amide," as used herein, refers to non-toxic amides of the application derived from ammonia, primary $C_1$-to-$C_6$ alkyl amines and secondary $C_1$-to-$C_6$ dialkyl amines. In the case of secondary amines, the amine can also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula (I) can be prepared according to conventional methods. Pharmaceutically acceptable amides can be prepared from compounds containing primary or secondary amine groups by reaction of the compound that contains the amino group with an alkyl anhydride, aryl anhydride, acyl halide, or aroyl halide. In the case of compounds containing carboxylic acid groups, the pharmaceutically acceptable esters are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, piperidine. They also can be prepared by reaction of the compound with an acid such as sulfuric acid and an alkylcarboxylic acid such as acetic acid, or with acid and an arylcarboxylic acid such as benzoic acid under dehydrating conditions as with molecular sieves added. The composition can contain a compound of the application in the form of a pharmaceutically acceptable prodrug.

The term "pharmaceutically acceptable prodrug" or "prodrug," as used herein, represents those prodrugs of the compounds of the application which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the application can be rapidly transformed in vivo to a parent compound of formula (I), for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

The application contemplates pharmaceutically active compounds either chemically synthesized or formed by in vivo biotransformation to compounds of formula (I).

Biological Activity

In Vitro Data—Determination of Inhibition Potencies

Dulbecco's modified Eagle medium (D-MEM) (with 4.5 mg/mL glucose) and fetal bovine serum were obtained from Hyclone Laboratories, Inc. (Logan, Utah). Dulbecco's phosphate-buffered saline (D-PBS) (with 1 mg/mL glucose and 3.6 mg/l Na pyruvate) (without phenol red), L-glutamine, hygromycin B, and Lipofectamine™ were obtained from Life Technologies (Grand Island, N.Y.). G418 sulfate was obtained from Calbiochem-Novabiochem Corp. (San Diego, Calif.). Capsaicin (8-methyl-N-vanillyl-6-nonenamide) was obtained from Sigma-Aldrich, Co. (St. Louis, Mo.). Fluo-4 AM (N-[4-[6-[(acetyloxy)methoxy]-2,7-difluoro-3-oxo-3H-xanthen-9-yl]-2-[2-[2-[bis[2-[(acetyloxy)methoxy]-2-oxyethyl]amino]-5-methylphenoxy]ethoxy]phenyl]-N-[2-[(acetyloxy)methoxy]-2-oxyethyl]-glycine, (acetyloxy) methyl ester) was purchased from Molecular Probes (Eugene, Oreg.).

The cDNAs for the human TRPV1 receptor were isolated by reverse transcriptase-polymerase chain reaction (RT-PCR) from human small intestine poly A+RNA supplied by Clontech (Palo Alto, Calif.) using primers designed surrounding the initiation and termination codons identical to the published sequences (Hayes et al. Pain 88: 205-215, 2000). The resulting cDNA PCR products were subcloned into pClneo mammalian expression vector (Promega) and fully sequenced using fluorescent dye-terminator reagents (Prism, Perkin-Elmer Applied Biosystems Division) and a Perkin-Elmer Applied Biosystems Model 373 DNA sequencer or Model 310 genetic analyzer. Expression plasmids encoding the hTRPV1 cDNA were transfected individually into 1321N1 human astrocytoma cells using Lipofectamine™. Forty-eight hours after transfection, the neomycin-resistant cells were selected with growth medium containing 800 µg/mL Geneticin (Gibco BRL). Surviving individual colonies were isolated and screened for TRPV1 receptor activity. Cells expressing recombinant homomeric TRPV1 receptors were maintained at 37° C. in D-MEM containing 4 mM L-glutamine, 300 µg/mL G418 (Cal-biochem) and 10% fetal bovine serum under a humidified 5% $CO_2$ atmosphere.

The functional activity of compounds at the TRPV1 receptor was determined with a $Ca^{2+}$ influx assay and measurement of intracellular $Ca^{2+}$ levels ($[Ca^{2+}]i$). All compounds were tested over an 11-point half-log concentration range. Compound solutions were prepared in D-PBS (4× final concentration), and diluted serially across 96-well v-bottom tissue culture plates using a Biomek 2000 robotic automation workstation (Beckman-Coulter, Inc., Fullerton, Calif.). A 0.2 µM solution of the TRPV1 agonist capsaicin was also prepared in D-PBS. The fluorescent $Ca^{2+}$ chelating dye fluo-4 was used as an indicator of the relative levels of $[Ca^{2+}]i$ in a 96-well format using a Fluorescence Imaging Plate Reader (FLIPR) (Molecular Devices, Sunnyvale, Calif.). Cells were grown to confluency in 96-well black-walled tissue culture plates. Then, prior to the assay, the cells were loaded with 100 µL per well of fluo-4 AM (2 in D-PBS) for 1-2 hours at 23° C. Washing of the cells was performed to remove extracellular fluo-4 AM (2×1 mL D-PBS per well), and afterward, the cells were placed in the reading chamber of the FLIPR instrument. 50 µL of the compound solutions were added to the cells at the 10 second time mark of the experimental run. Then, after a 3 minute time delay, 50 µL of the capsaicin solution was added at the 190 second time mark (0.05 µM final concentration) (final volume=200 µL) to challenge the TRPV1 receptor. Time length of the experimental run was 240 seconds. Fluorescence readings were made at 1 to 5 second intervals over the course of the experimental run. The peak increase in relative fluorescence units (minus baseline) was calculated from the 190 second time mark to the end of the experimental run, and expressed as a percentage of the 0.05 µM capsaicin (control) response. Curve-fits of the data were solved using a four-parameter logistic Hill equation in GraphPad Prism® (GraphPad Software, Inc., San Diego, Calif.), and $IC_{50}$ values were calculated.

The compounds of the present application were found to be antagonists of the vanilloid receptor subtype 1 (TRPV1) receptor with $IC_{50s}$ lower than 12 preferably lower than 5 µM, more preferably less than 1 µM, and most preferably less than 0.1 µM.

In Vivo Data—Determination of Antinociceptive Effect

Experiments were performed on 400 adult male 129J mice (Jackson Laboratories, Bar Harbor, Me.), weighing 20-25 g. Mice were kept in a vivarium, maintained at 22° C., with a 12 hour alternating light-dark cycle with food and water available ad libitum. All experiments were performed during the light cycle. Animals were randomly divided into separate groups of 10 mice each. Each animal was used in one experiment only and was sacrificed immediately following the completion of the experiment. All animal handling and experimental procedures were approved by an IACUC Committee. The Complete Freund's Adjuvant-induced Thermal Hyperalgesia (CFA) assay described in Pircio et al., Eur J Pharmacol. Vol. 31(2), pages 207-215 (1975). Chronic inflammatory hyperalgesia was induced in one group of rats following the injection of complete Freund's adjuvant (CFA, 50%, 150 µL) into the plantar surface of the right hindpaw 48 hours prior to testing. Thermal nociceptive thresholds were measured in three different groups of rats. The $ED_{50s}$ were determined based on the oral administration.

The in vitro and in vivo data demonstrates that compounds of the present application antagonize the TRPV1 receptor and are useful for treating pain, bladder overactivity, and urinary incontinence.

Methods of Use

Compounds and compositions of the application are useful for ameliorating or preventing disorders involving TRPV1 receptor activation such as, but not limited to pain, nociceptive pain, neuropathic pain, migraine, ostheoarthritis pain, chronic lower pain, allodynia, pain associated with inflammation, bladder overactivity, and urinary incontinence as described by Nolano, M. et al., Pain, Vol. 81, pages 135-145, (1999); Caterina, M. J. and Julius, D., Annu Rev. Neurosci. Vol. 24, pages 487-517 (2001); Caterina, M. J. et al., Science Vol. 288 pages 306-313 (2000); Caterina, M. J. et al., Nature Vol. 389, pages 816-824 (1997); Fowler, C. Urology Vol. 55, pages 60-64 (2000); and Davis, J. et al., Nature Vol. 405, pages 183-187.

Compounds of the invention may be administered alone, or in combination with one or more other compounds of the invention, or in combination (i.e. co-administered) with one or more additional pharmaceutical agents. For example, a compound of formula (I) or a pharmaceutically acceptable salt or solvate thereof, may be administered in combination with one or more nonsteroidal anti-inflammatory drug (NSAID) such as, but not limited to, aspirin, acetaminophen, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac. Combination therapy includes administration of a single pharmaceutical dosage formulation containing one or more of the compounds of invention and one or more additional pharmaceutical agents, as well as administration of the compounds of the invention and each additional pharmaceutical agent, in its own separate pharmaceutical dosage formulation. For example, a compound of formula (I) and one or more additional pharmaceutical agents, may be administered to the patient together, in a single oral dosage composition having a fixed ratio of each active ingredient, such as a tablet or capsule; or each agent may be administered in separate oral dosage formulations.

Where separate dosage formulations are used, compounds of the invention and one or more additional pharmaceutical agents may be administered at essentially the same time (e.g., concurrently) or at separately staggered times (e.g., sequentially).

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

Compounds of the invention can also be administered as a pharmaceutical composition comprising the compounds of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

What is claimed is:

1. A compound of formula (I)

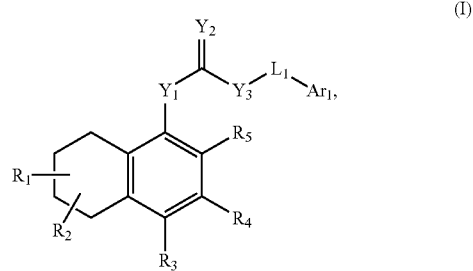

or a pharmaceutically acceptable salt thereof, wherein
$L_1$ is a bond;
$Y_1$ is —N($R_b$)—;
$Y_2$ is =O, =S or =N—CN;
$Y_3$ is —N($R_c$)—;
$Ar_1$ is 1,2,3,4-tetrahydro-quinolin-2-yl, 1,2,3,4-tetrahydro-quinolin-3-yl, or 1,2,3,4-tetrahydro-quinolin-4-yl;

wherein each $Ar_1$ is optionally substituted with 1, 2, 3, 4, or 5 substituents as represented by $R_w$, two $R_w$ that are attached to the same carbon atom of the monocyclic heterocycle, together with the carbon atom to which they are attached, optionally form a monocyclic cycloalkyl ring wherein said monocyclic cycloalkyl ring is optionally substituted with 1, 2, or 3 substituents selected from the group consisting of oxo, alkyl, and haloalkyl;

$R_1$ is hydrogen, hydroxy or alkoxy;

$R_w$, $R_2$, $R_3$, $R_4$, and $R_5$, are each independently hydrogen, alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylthio, alkynyl, carboxy, carboxyalkyl, cyano, cyanoalkyl, cycloalkyl, cycloalkylalkyl, formyl, formylalkyl, haloalkoxy, haloalkyl, haloalkylthio, halogen, hydroxy, hydroxyalkyl, nitro, $R_eOS(O)_2$—, $R_fR_gN$—, $(R_fR_gN)$alkyl, $(R_fR_gN)$carbonyl, $(R_jR_kN)$carbonylalkyl or $(R_jR_kN)$sulfonyl;

$R_b$ and $R_c$ are each independently hydrogen or alkyl;

$R_e$ is alkyl, haloalkyl, aryl, or arylalkyl;

$R_f$ and $R_g$, at each occurrence, are each independently hydrogen, alkenyl, alkoxyalkyl, alkoxycarbonyl, alkoxycarbonylalkyl, alkyl, alkylcarbonyl, alkylcarbonylalkyl, arylalkyl, arylcarbonyl, carboxyalkyl, cycloalkylalkyl, haloalkyl, heteroarylalkyl, or heteroarylcarbonyl; or $R_f$ and $R_g$ taken together with the nitrogen atom to which they are attached form a heterocyclic ring; and $R_j$ and $R_k$, at each occurrence, are each independently hydrogen, alkenyl, alkoxyalkyl, alkoxycarbonylalkyl, alkyl, alkylcarbonylalkyl, carboxyalkyl, cycloalkylalkyl, haloalkyl, or hydroxyalkyl.

2. The compound, or pharmaceutically acceptable salt thereof, according to claim 1 wherein
$Y_2$ is =O.

3. The compound, or pharmaceutically acceptable salt thereof, according to claim 2, wherein
$R_1$ is hydroxy; and
$R_2$ is hydrogen.

4. The compound, or pharmaceutically acceptable salt thereof, according to claim 2 wherein
$R_1$ is hydroxy; and
$R_2$, $R_3$, $R_4$, and $R_5$ are hydrogen.

5. The compound, or pharmaceutically acceptable salt thereof, according to claim 2, wherein
$R_1$ is hydroxy;
$R_2$ is hydrogen; and
$Ar_1$ is 1,2,3,4-tetrahydroquinolin-4-yl.

6. The compound, or pharmaceutically acceptable salt thereof, according to claim 5 wherein $Ar_1$ is optionally substituted with 1, 2, 3, 4, or 5 substituents as represented by $R_w$, and each $R_w$ is independently alkoxy, alkyl, arylalkyl, halogen, haloalkyl, or $R_fR_gN$— wherein $R_f$ and $R_g$ are each independently hydrogen, alkyl, or haloalkyl.

7. The compound, or pharmaceutically acceptable salt thereof, according to claim 2, wherein
$R_1$ is hydroxy;
$R_2$ is hydrogen; and
$Ar_1$ is 1,2,3,4-tetrahydroquinolin-3-yl.

8. The compound, or pharmaceutically acceptable salt thereof, according to claim 7 wherein $Ar_1$ is optionally substituted with 1, 2, 3, 4, or 5 substituents as represented by $R_w$, and each $R_w$ is independently alkoxy, alkyl, arylalkyl, halogen, haloalkyl, or $R_fR_gN$— wherein $R_f$ and $R_g$ are each independently hydrogen, alkyl, or haloalkyl.

9. The compound, or pharmaceutically acceptable salt thereof, according to claim 2, wherein
$R_1$ is hydroxy;
$R_2$ is hydrogen; and
$Ar_1$ is 1,2,3,4-tetrahydroquinolin-2-yl.

10. The compound, or pharmaceutically acceptable salt thereof, according to claim 4, wherein
$Ar_1$ is 1,2,3,4-tetrahydroquinolin-4-yl.

11. The compound, or pharmaceutically acceptable salt thereof, according to claim 10 wherein $Ar_1$ is optionally substituted with 1, 2, 3, 4, or 5 substituents as represented by $R_w$, and each $R_w$ is independently alkoxy, alkyl, arylalkyl, halogen, haloalkyl, or $R_fR_gN$— wherein $R_f$ and $R_g$ are each independently hydrogen, alkyl, or haloalkyl.

12. The compound according to claim 4, wherein
$Ar_1$ is 1,2,3,4-tetrahydro-quinolin-3-yl.

13. The compound, or pharmaceutically acceptable salt thereof, according to claim 12 wherein $Ar_1$ is optionally substituted with 1, 2, 3, 4, or 5 substituents as represented by $R_w$, and each $R_w$ is independently alkoxy, alkyl, arylalkyl, halogen, haloalkyl, or $R_fR_gN$— wherein $R_f$ and $R_g$ are each independently hydrogen, alkyl, or haloalkyl.

14. The compound, or pharmaceutically acceptable salt thereof, according to claim 1 selected from the group consisting of:

N-(8-tert-butyl-1-methyl-1,2,3,4-tetrahydroquinolin-4-yl)-N'-(7-hydroxy-5,6,7,8-tetrahydronaphthalen-1-yl)urea;

N-(1-benzyl-1,2,3,4-tetrahydroquinolin-3-yl)-N'-(7-hydroxy-5,6,7,8-tetrahydronaphthalen-1-yl)urea;

N-[1-benzyl-7-(trifluoromethyl)-1,2,3,4-tetrahydroquinolin-3-yl]-N'-(7-hydroxy-5,6,7,8-tetrahydronaphthalen-1-yl)urea;

N-(7-hydroxy-5,6,7,8-tetrahydronaphthalen-1-yl)-N'-(1-methyl-1,2,3,4-tetrahydroquinolin-4-yl)urea;

N-(7-hydroxy-5,6,7,8-tetrahydronaphthalen-1-yl)-N'-[1-methyl-7-(trifluoromethyl)-1,2,3,4-tetrahydroquinolin-4-yl]urea;

N-(1-benzyl-1,2,3,4-tetrahydroquinolin-3-yl)-N'-(7-hydroxy-5,6,7,8-tetrahydronaphthalen-1-yl)urea;

N-[1-benzyl-7-(trifluoromethyl)-1,2,3,4-tetrahydroquinolin-3-yl]-N'-(7-hydroxy-5,6,7,8-tetrahydronaphthalen-1-yl)urea;

N-(7-hydroxy-5,6,7,8-tetrahydronaphthalen-1-yl)-N'-(1-methyl-1,2,3,4-tetrahydroquinolin-3-yl)urea;

N-(7-hydroxy-5,6,7,8-tetrahydronaphthalen-1-yl)-N'-[1-methyl-7-(trifluoromethyl)-1,2,3,4-tetrahydroquinolin-3-yl]urea; and pharmaceutically acceptable salts thereof.

15. A pharmaceutical composition comprising a therapeutically effective amount of a compound of formula (I), or pharmaceutically acceptable salt thereof, according to claim 1.

16. The pharmaceutical composition according to claim 15 further including a non-toxic pharmaceutically acceptable carrier and diluent.

* * * * *